(12) United States Patent
Heilman et al.

(10) Patent No.: US 9,707,327 B2
(45) Date of Patent: Jul. 18, 2017

(54) THORACIC AORTA VENTRICULAR ASSIST SYSTEM

(71) Applicant: VASCOR, INC., Pittsburgh, PA (US)

(72) Inventors: Marlin S. Heilman, Saver, PA (US); Charles R. Kohler, Cheswick, PA (US); David M. Reilly, Pittsburgh, PA (US); Jon D. Wagner, Pittsburgh, PA (US); Kurt D. Badstibner, North Versailles, PA (US); Richard A. Bates, Allison Park, PA (US); Jonathan R. Speicher, Pittsburgh, PA (US); Joseph F. Russial, Pittsburgh, PA (US)

(73) Assignee: VASCOR, INC., Pittsburgh, PA (US)

( * ) Notice: Subject to any disclaimer, the term of this patent is extended or adjusted under 35 U.S.C. 154(b) by 0 days.

(21) Appl. No.: 14/776,927

(22) PCT Filed: Mar. 17, 2014

(86) PCT No.: PCT/US2014/030472
§ 371 (c)(1),
(2) Date: Sep. 15, 2015

(87) PCT Pub. No.: WO2014/145667
PCT Pub. Date: Sep. 18, 2014

(65) Prior Publication Data
US 2016/0022888 A1   Jan. 28, 2016

Related U.S. Application Data

(60) Provisional application No. 61/788,030, filed on Mar. 15, 2013.

(51) Int. Cl.
*A61M 1/10*   (2006.01)
*A61M 1/12*   (2006.01)

(52) U.S. Cl.
CPC .......... *A61M 1/1049* (2014.02); *A61M 1/107* (2013.01); *A61M 1/1051* (2014.02);
(Continued)

(58) Field of Classification Search
CPC ..... A61B 5/0205; A61B 5/026; A61B 5/0215; A61B 5/029; A61B 5/0484; A61B 5/72;
(Continued)

(56) References Cited

U.S. PATENT DOCUMENTS 3,553,736 A   1/1971 Kantrowitz
3,857,382 A   12/1974 Williams
(Continued)

FOREIGN PATENT DOCUMENTS

EP           1466635 A1    10/2004
WO      WO2014145667       9/2014

*Primary Examiner* — Deborah Malamud
(74) *Attorney, Agent, or Firm* — Bartony & Associates, LLC

(57) ABSTRACT

An implantable heart assist system, includes a pumping chamber formed of a flexible material and being adapted to be placed in fluid connection with the aorta and a pump system comprising a first rigid member and a spaced apart second rigid member so that at least a portion of the pumping chamber may be positioned therebetween, a drive system comprising a motor. The motor is adapted to cause the second rigid member to move toward the first rigid member to compress the pumping chamber or away from the first rigid member to expand the pumping chamber. A controller is in operative connection with the drive system and controlling the motor.

22 Claims, 32 Drawing Sheets

(52) U.S. Cl.
CPC .......... *A61M 1/1086* (2013.01); *A61M 1/122* (2014.02); *A61M 2230/005* (2013.01); *A61M 2230/04* (2013.01)

(58) Field of Classification Search
CPC ....... A61B 5/6876; A61B 5/0245; A61B 5/04; A61M 1/122; A61M 1/1087; A61M 1/10; A61M 1/1037; A61M 1/1068; A61M 1/1086; A61M 1/127; A61M 1/101; A61M 1/1046; A61M 1/1049; A61M 1/12; A61M 1/125; A61M 1/1041; A61M 1/1053; A61M 2230/005; A61M 2230/04; A61N 1/05; A61N 1/303; Y10S 623/904
See application file for complete search history.

(56) References Cited

U.S. PATENT DOCUMENTS

| | | | |
|---|---|---|---|
| 4,014,318 A | 3/1977 | Dockum | |
| 4,077,394 A | 3/1978 | McCurdy | |
| 4,583,523 A | 4/1986 | Kleinke | |
| 4,979,936 A | 12/1990 | Stepherson | |
| 5,290,227 A * | 3/1994 | Pasque | A61M 1/101 417/356 |
| 5,647,380 A | 7/1997 | Campbell | |
| 5,980,448 A | 11/1999 | Heilman | |
| 6,030,336 A | 2/2000 | Franchi | |
| 6,471,633 B1 | 10/2002 | Freed | |
| 7,347,811 B2 | 3/2008 | Peters | |
| 7,357,771 B2 | 4/2008 | Peters | |
| 7,494,459 B2 * | 2/2009 | Anstadt | A61M 1/1068 600/17 |
| 7,765,003 B2 | 7/2010 | Peters | |
| 2006/0014999 A1 | 1/2006 | Heilman | |
| 2011/0071337 A1 | 3/2011 | Thompson | |
| 2012/0220816 A1 | 8/2012 | Peters | |
| 2013/0041204 A1 | 2/2013 | Heilman | |
| 2013/0289334 A1 | 10/2013 | Badstibner | |

* cited by examiner

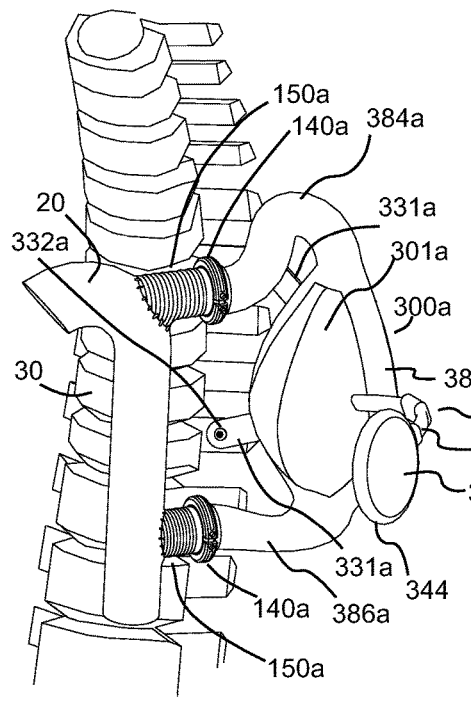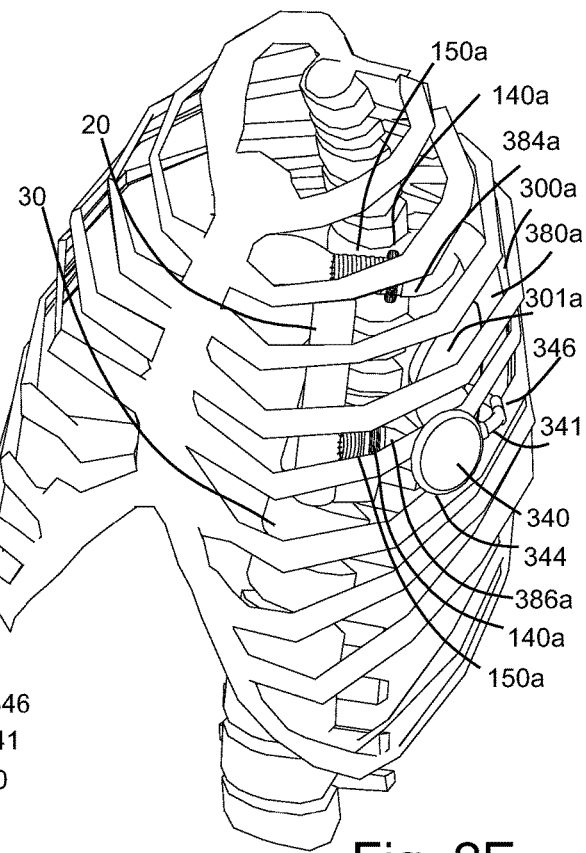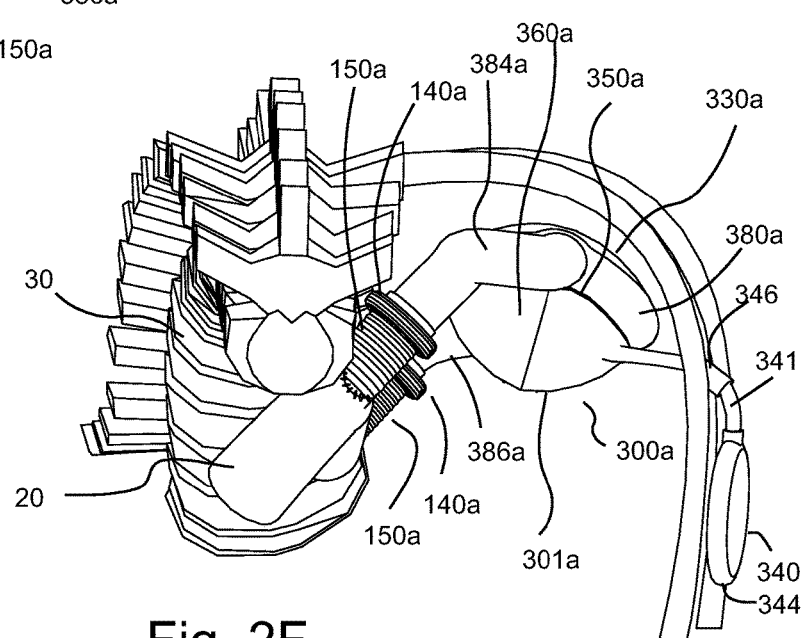

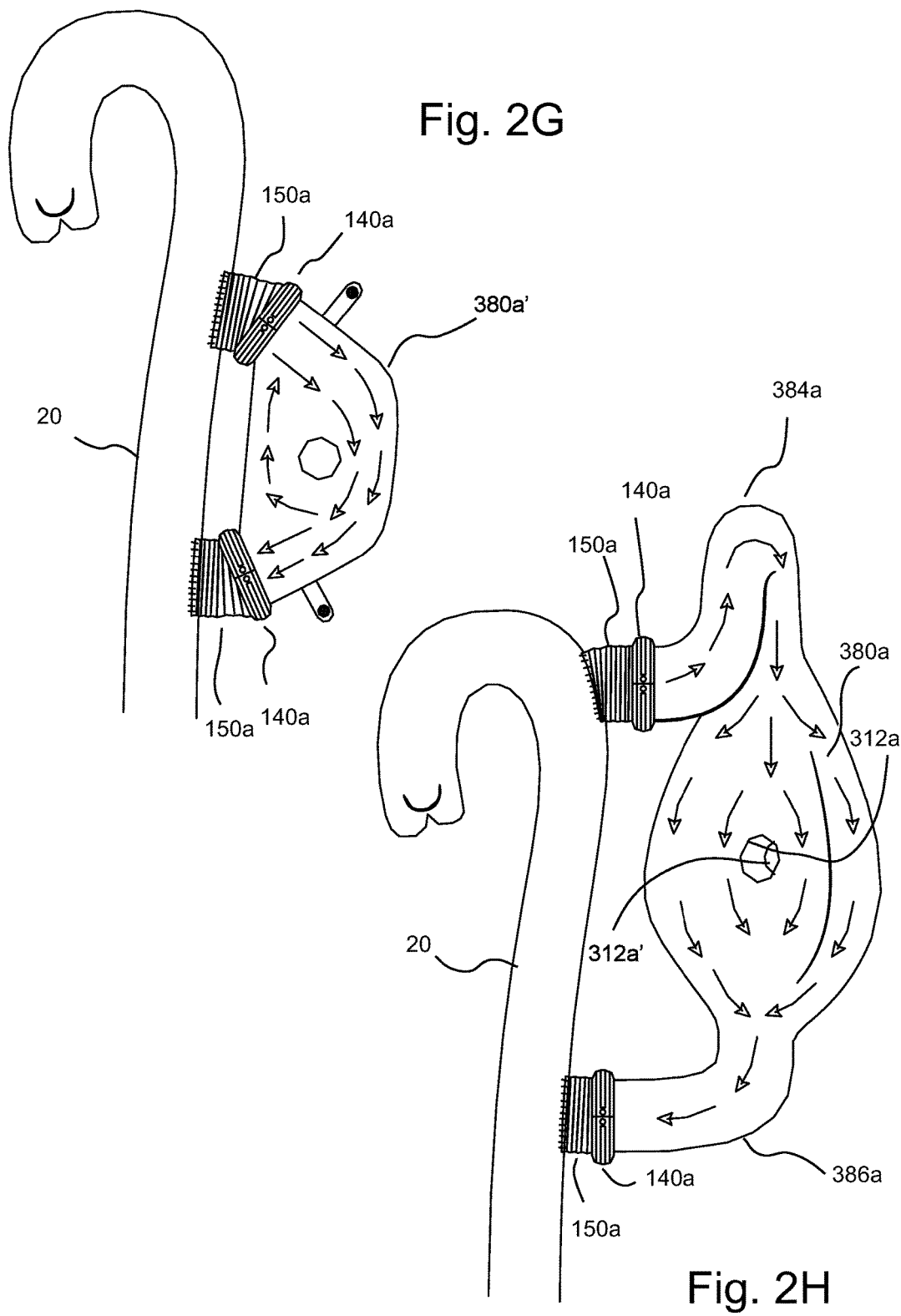

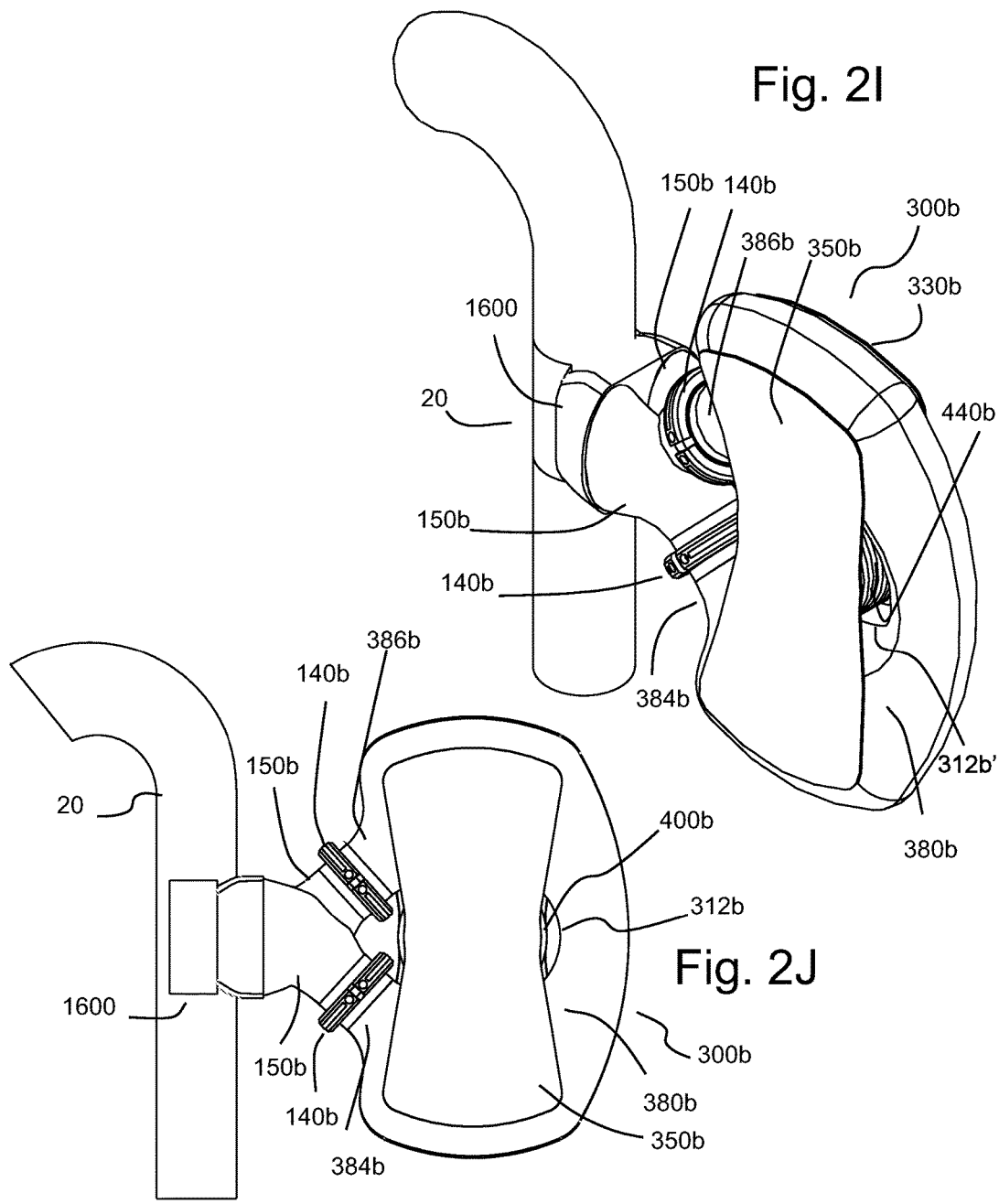
Fig. 2I
Fig. 2J
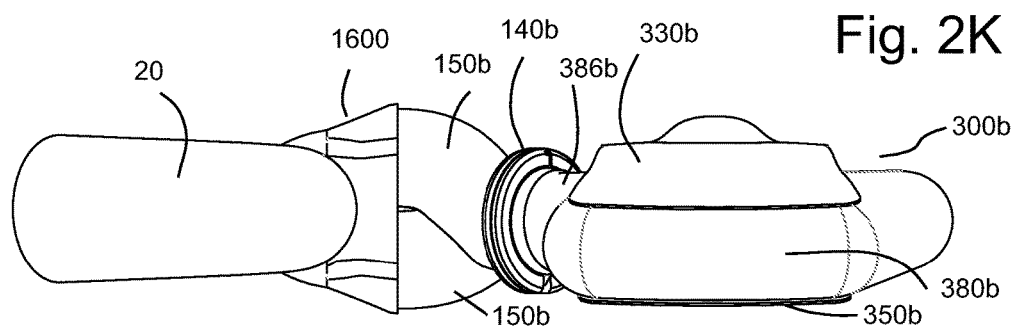
Fig. 2K

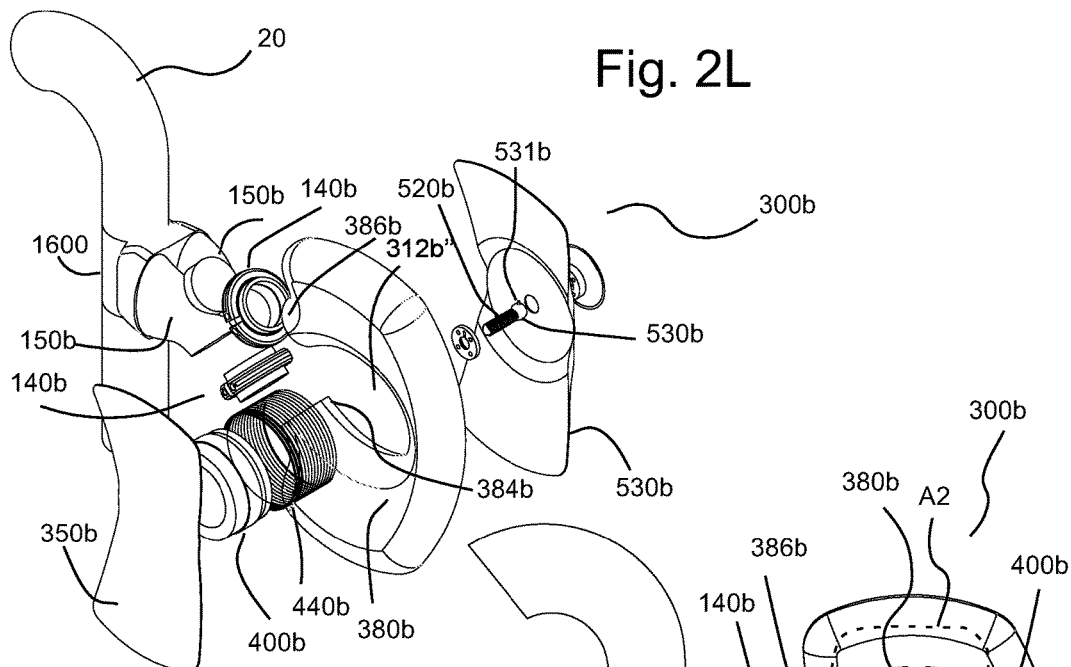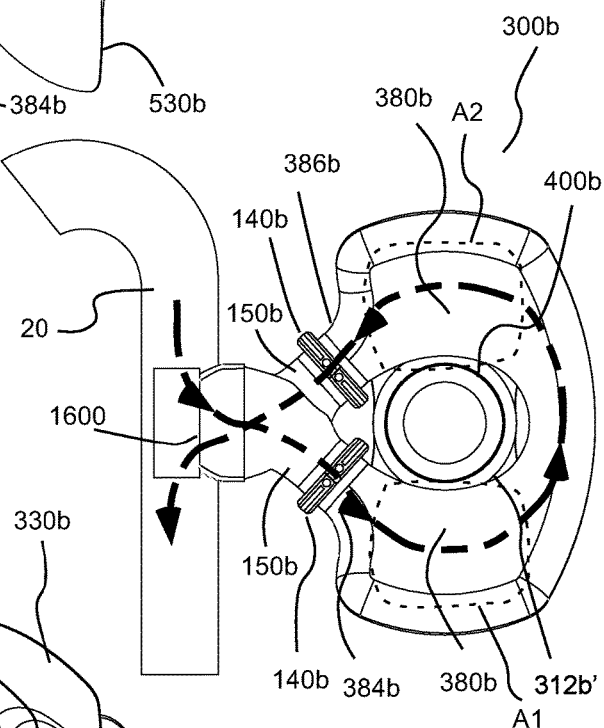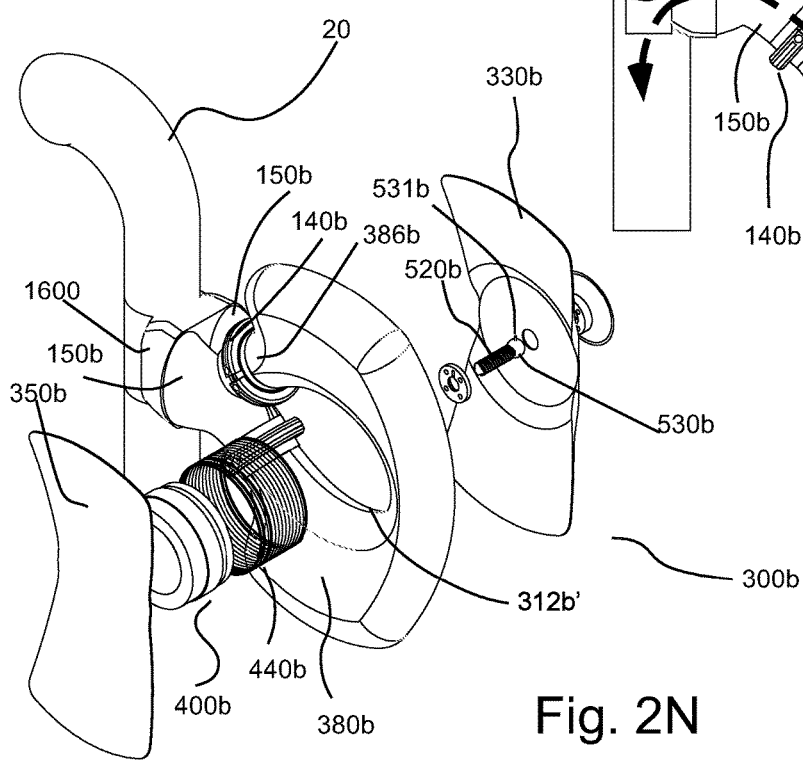

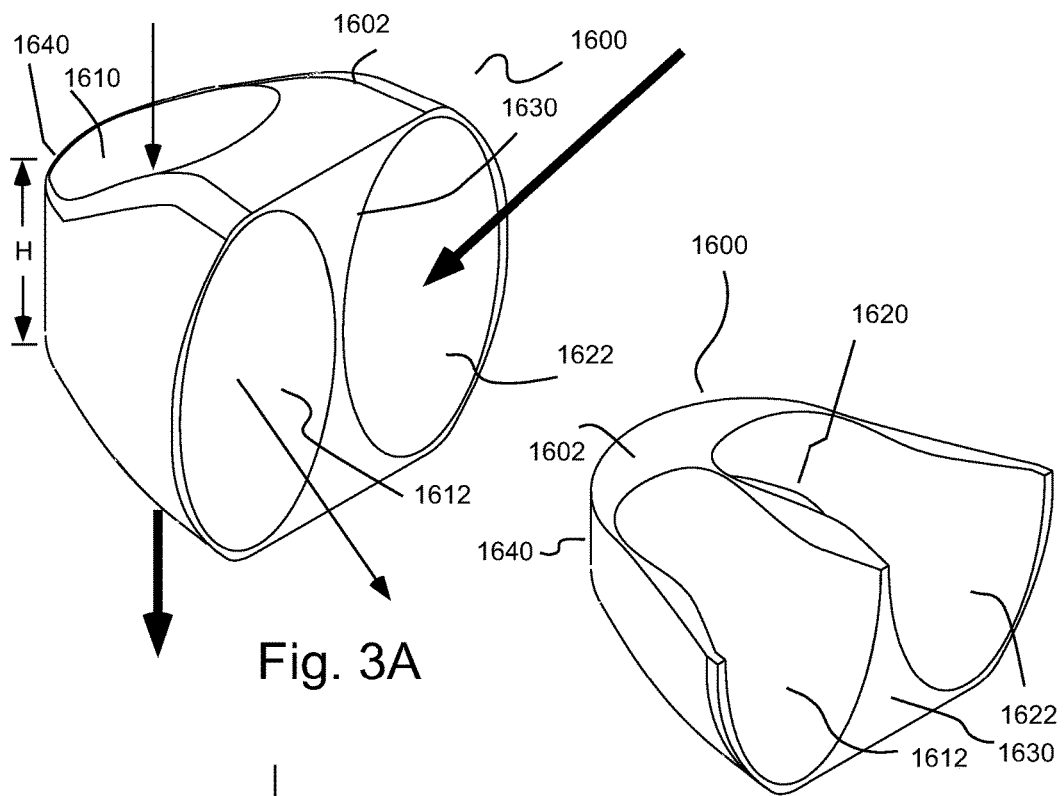
Fig. 3A
Fig. 3B
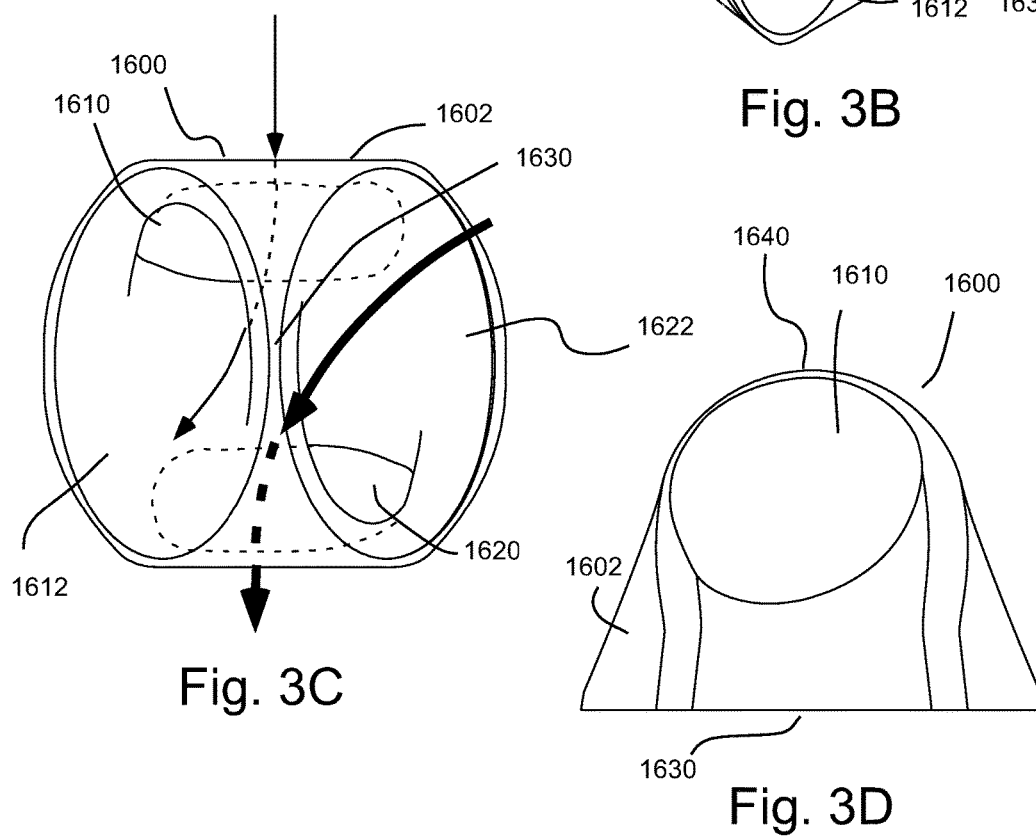
Fig. 3C
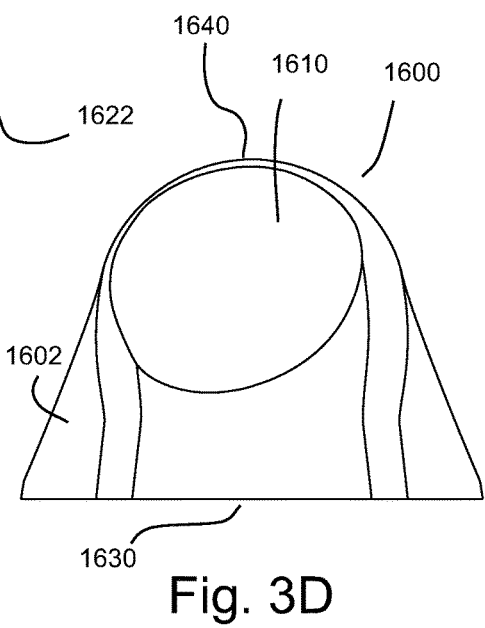
Fig. 3D

Fig. 5C
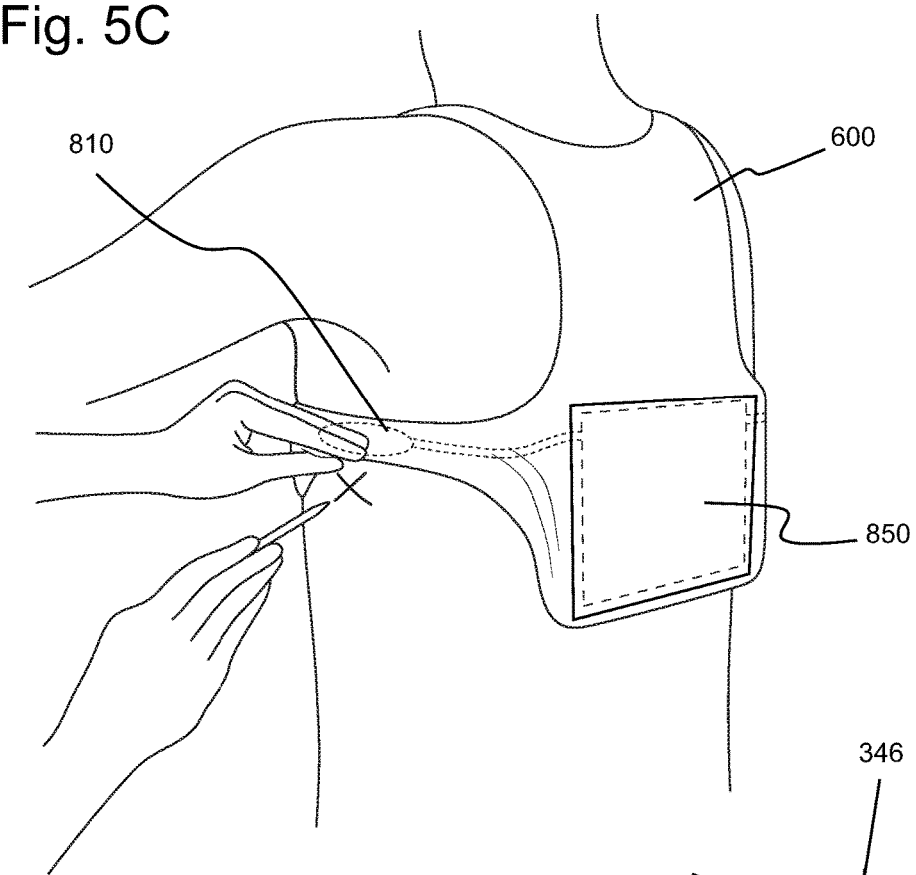
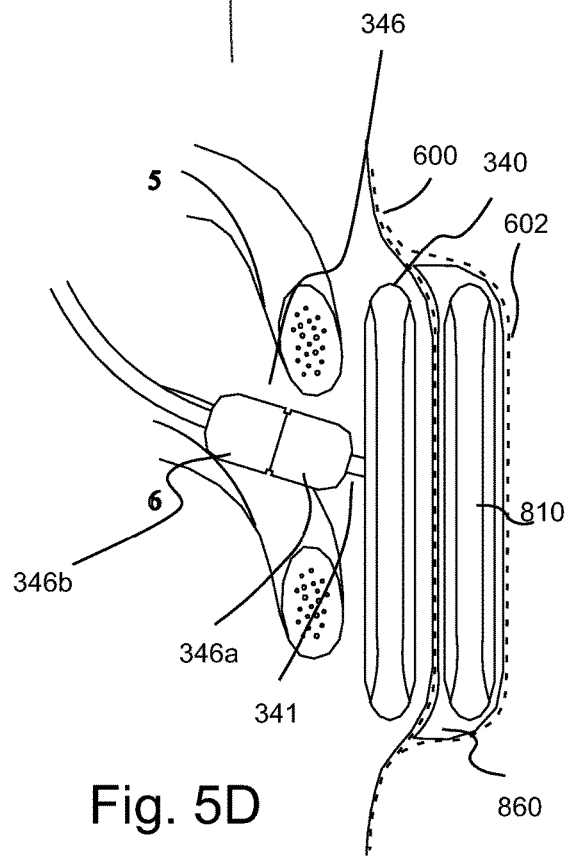
Fig. 5D

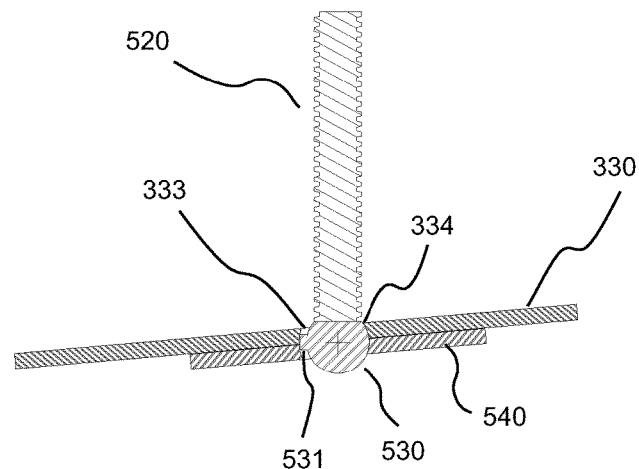
Fig. 9B
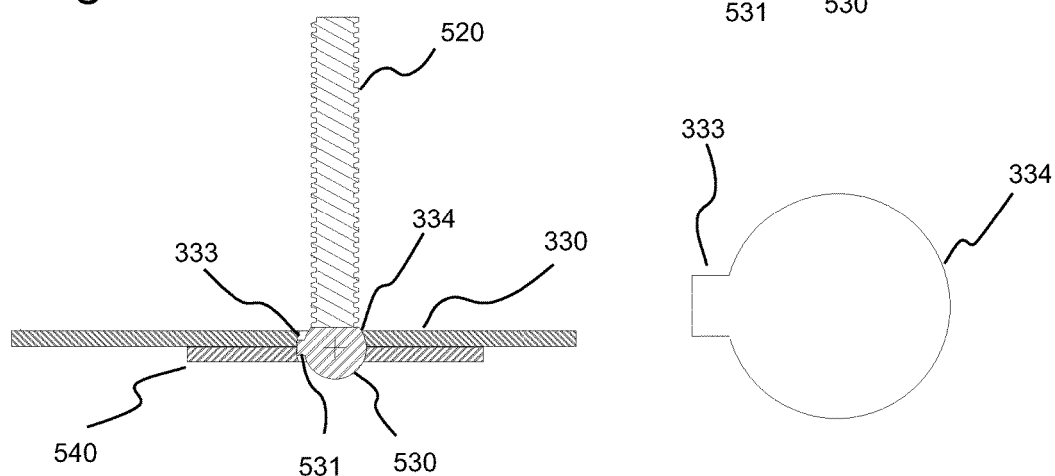
Fig. 9A
Fig. 9C
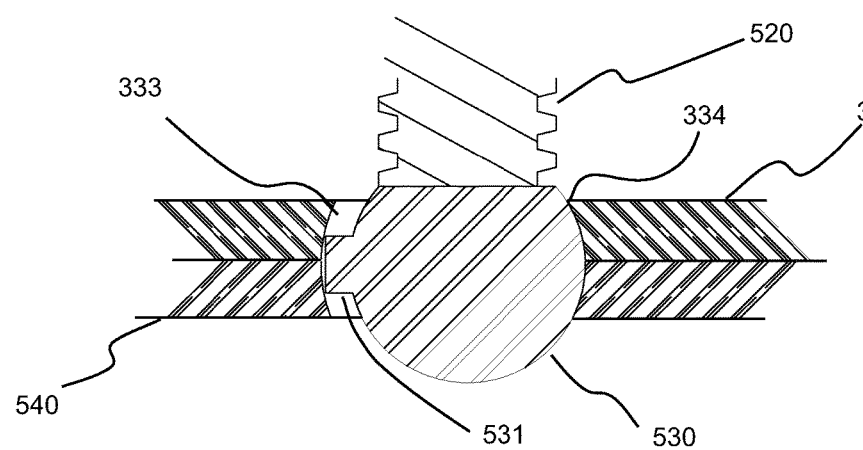
Fig. 9D

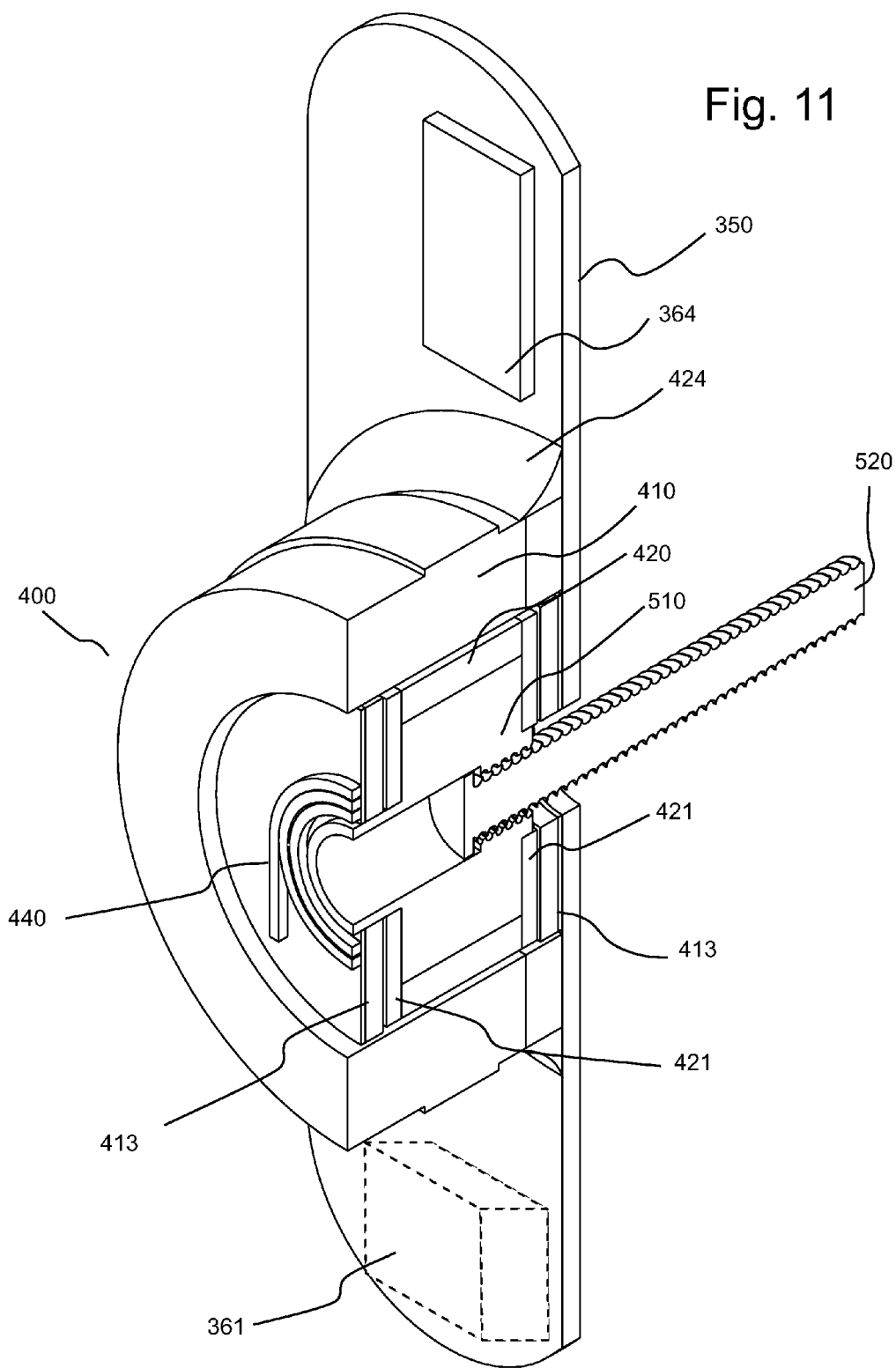

Fig. 15A
Fig. 15B
Fig. 16A
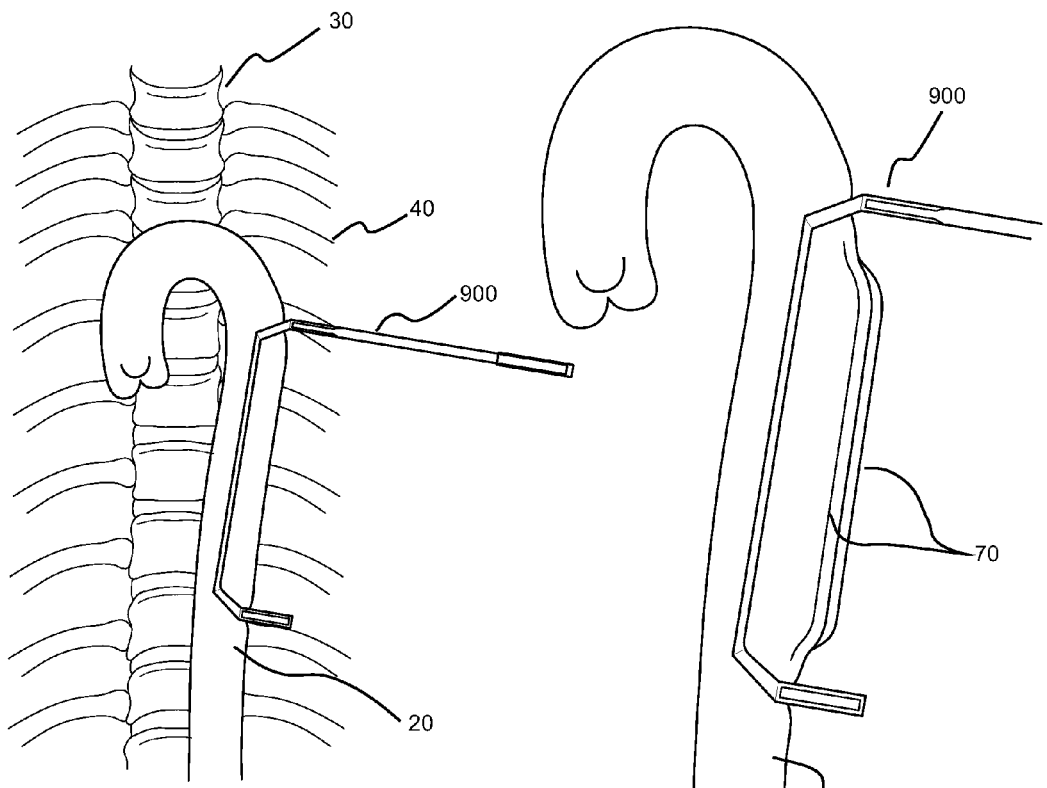
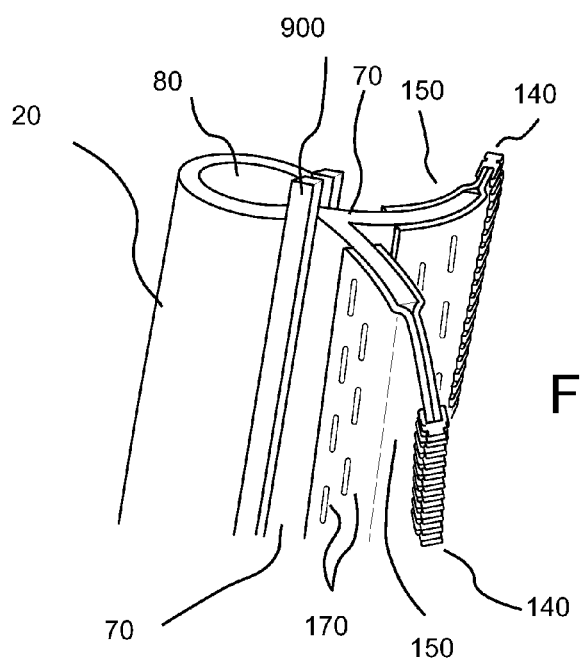

Fig. 16F
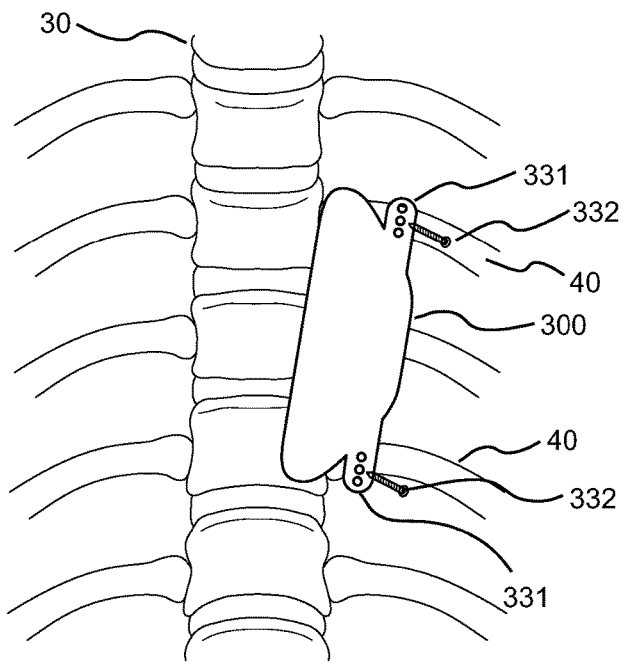
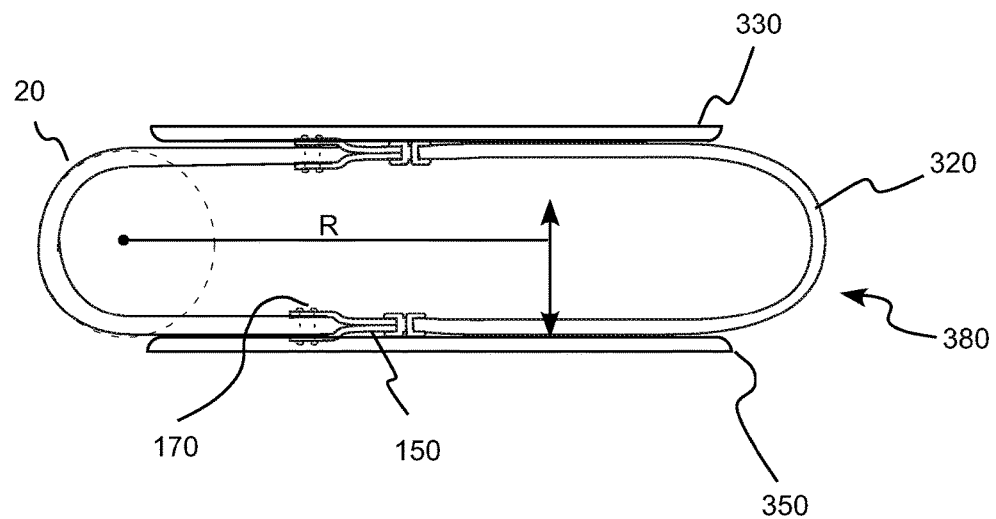
Fig. 17

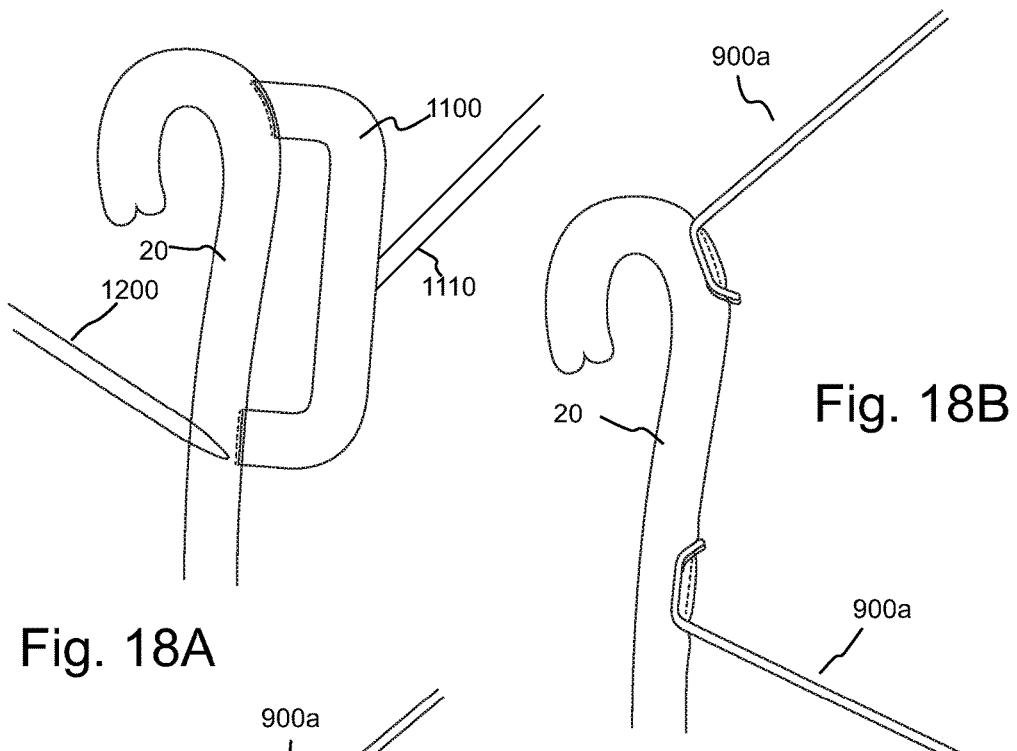
Fig. 18A
Fig. 18B
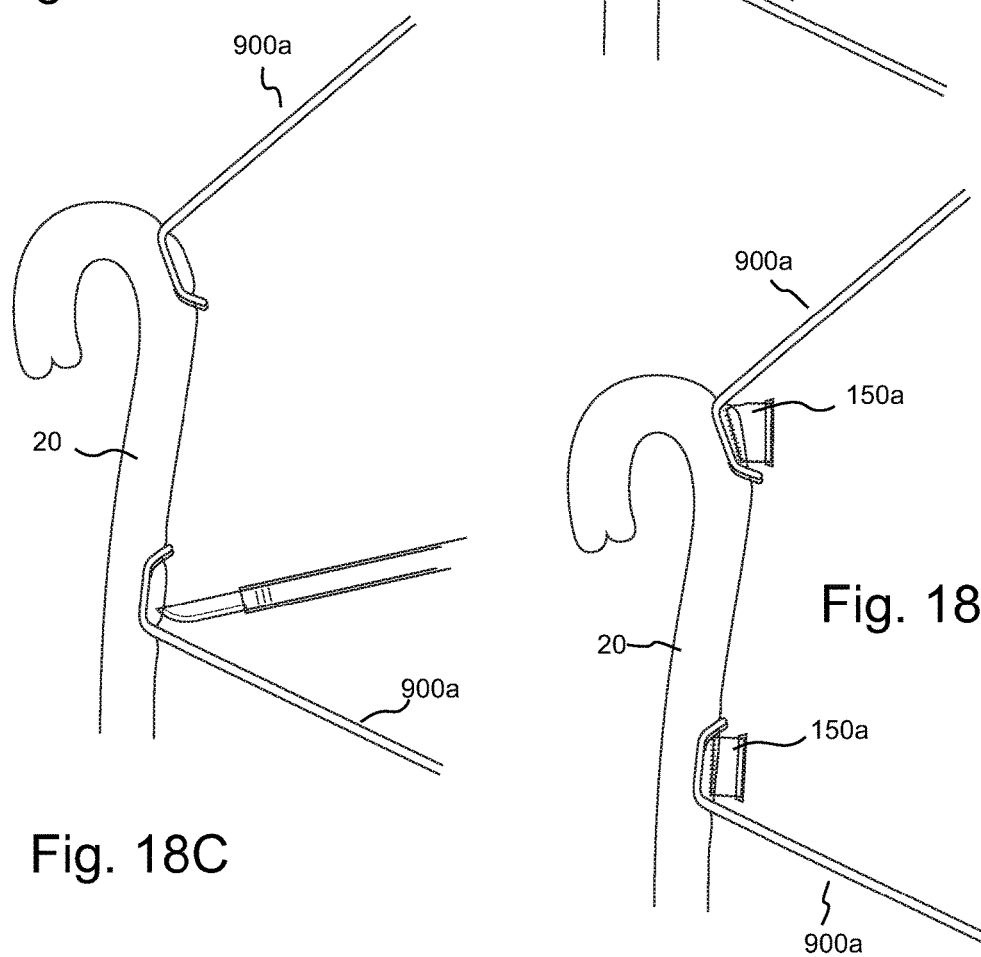
Fig. 18C
Fig. 18D

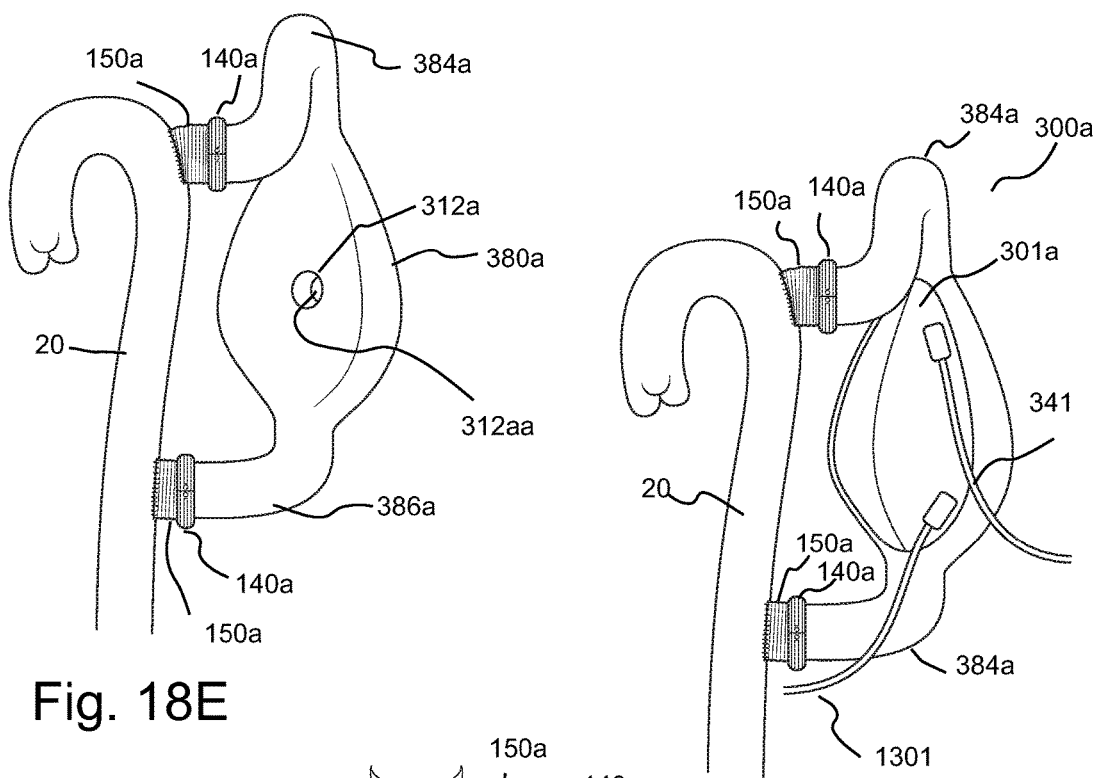
Fig. 18E
Fig. 18F
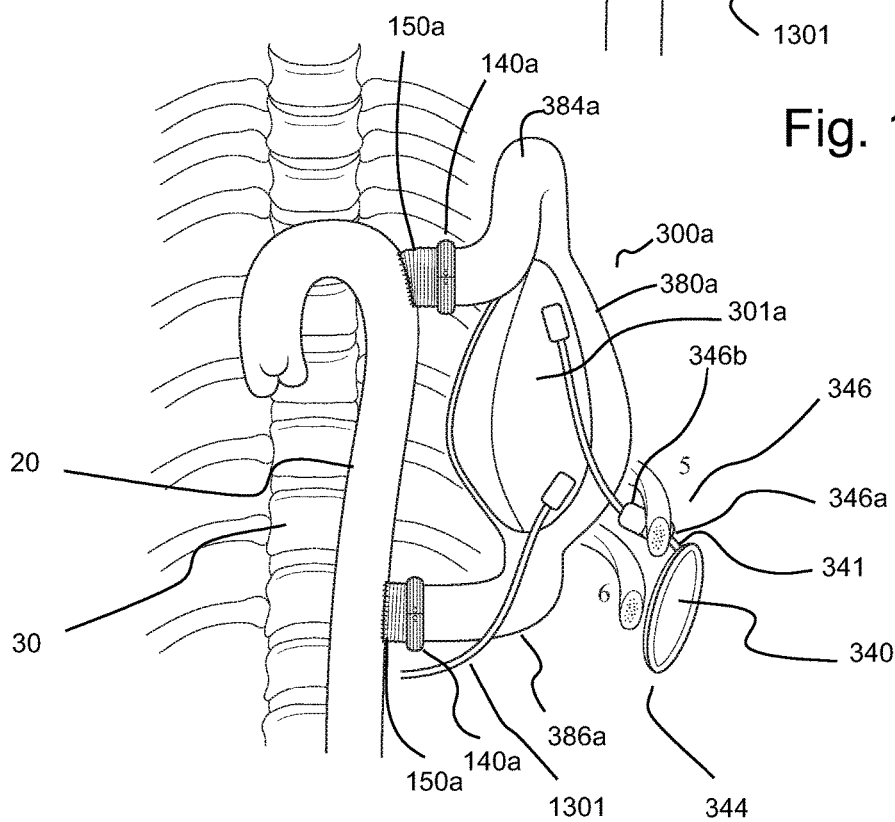
Fig. 18G

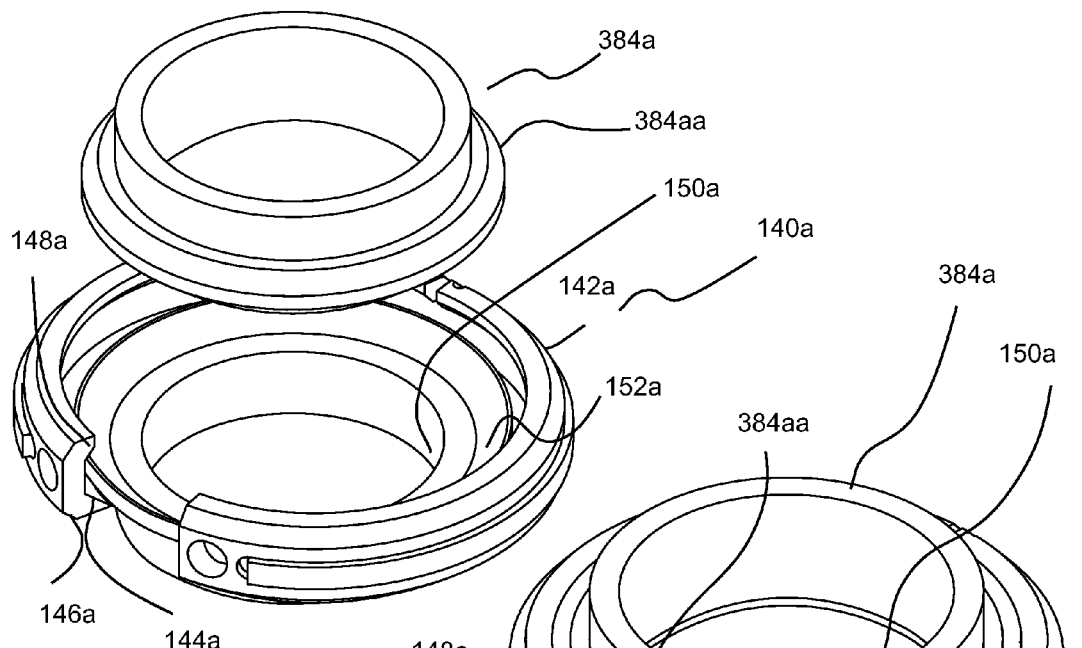
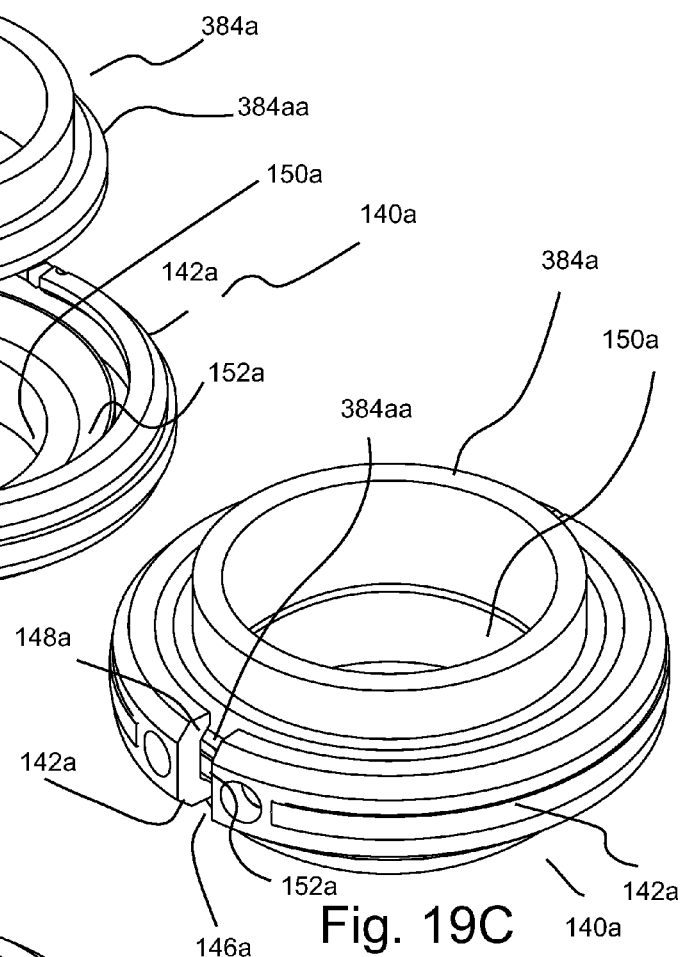
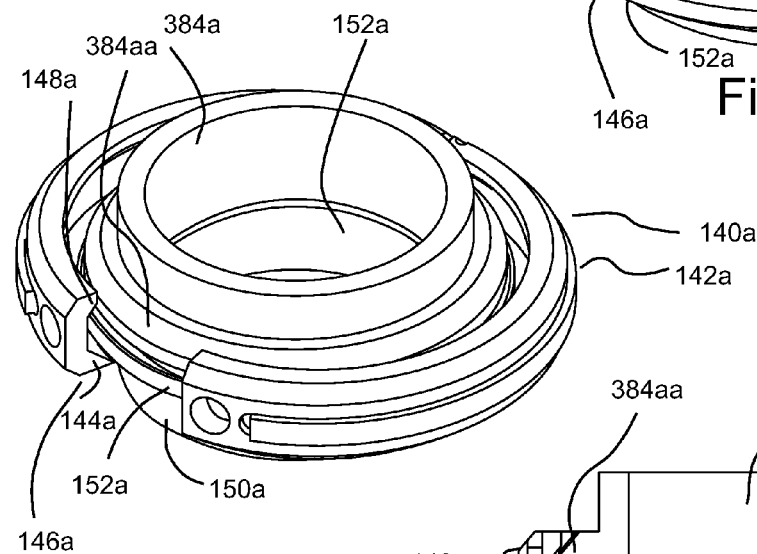
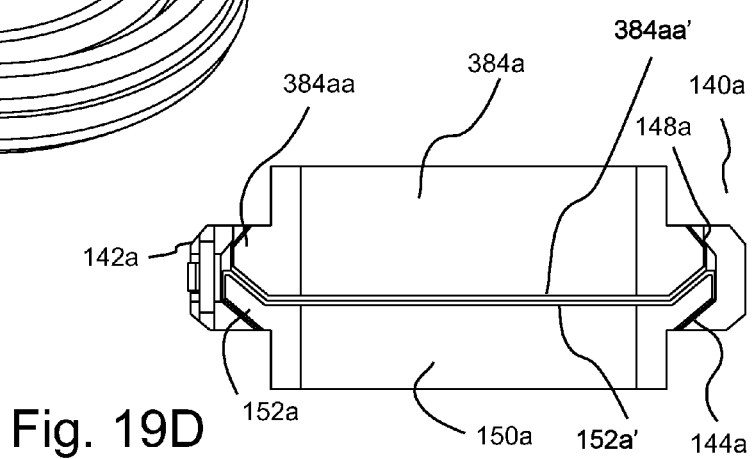
Fig. 19A
Fig. 19B
Fig. 19C
Fig. 19D

THORACIC AORTA VENTRICULAR ASSIST SYSTEM

CROSS-REFERENCE TO RELATED APPLICATION

This application is a national phase filing of PCT International Patent Application No. PCT/US2014/030472, filed Mar. 17, 2014, which claims benefit of U.S. Provisional Patent Application Ser. No. 61/788,030, filed Mar. 15, 2013, the disclosures of which is are incorporated herein by reference.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Congestive heart failure or CHF affects an estimated 5.7 million persons in the United States alone. Increasingly, heart assist devices are being implanted in a patient's body to assist the patient's weak heart, by increasing the blood flow to the body. Such increased blood flow alleviates the symptoms of congestive heart failure, and returns the patient to a normal or near normal state of health.

As used herein, the term "powered" generally refers to the use of electrical power. As used herein, the term "implanted" refers to a medical device either partially or completely inserted into the body of a patient, for example, a human patient. The term "thoracic aorta" or "TA" refers to the descending thoracic aorta. Commonly, the term ventricular assist device or VAD is used to describe pumps that help the heart deliver more blood to the body. For simplification, the term "VAD", as used herein, describes any device or system that mechanically helps the heart pump more blood. VADs traditionally have used positive displacement collapsing pumping chambers having inlet and outlet valves to force forward blood flow in a pulsing manner. Such positive-displacement, pulsing VADs have been physically too large for use in small patients. State-of-the-art VADs have rotating impeller pumps that slice and push blood forward and are significantly smaller the older VADs to fit in any sized adult patients. However, state-of-the-art rotating impeller VADs have a number of serious drawbacks, including, blood damage, infection risk and the fact that they are not failsafe. The impeller blades of such VADs operate at high speeds (for example, 3,000 to 8,000 revolutions per minute) and impart high shear stress to the blood components including red blood cells, platelets and a high molecular weight protein called the von Willibrand factor. Also, in some cases, rotating VADs use the blood itself as a bearing material, which is a source of substantial shear. Because of shear related blood damage, patients with implanted rotary VADs often experience excessive bleeding and clotting, leading to brain damage, strokes and/or the need for blood transfusions. Additionally, because rotary VADs are placed in parallel with the heart's left ventricle, the loss of pump power may be fatal in an estimated 40 percent of the patients. This risk arises with loss of power because the non-rotating impeller pump, which is placed in parallel with the left ventricle, becomes a shunt path for high pressure arterial blood to flow backward into the weak low pressure left ventricle, overloading it into a severe state of failure.

A number of VADs have used the principle of counter pulsation to boost blood flow from the left ventricle to the body. For example, a hot-dog shaped intra-aortic balloon may be inserted into the thoracic aorta or TA through a minimally invasive femoral artery incision and pulsed with gas pressure and vacuum to alternately inflate and deflate the balloon. The balloon inflation is timed to occur early in diastole, pushing blood to the body during the heart's resting and filling time period, and to deflate late in diastole or early systole, making it easier for the heart to empty its blood into the aorta.

In other words, intra-aortic balloon counter pulsation works by adding energy and blood flow to the circulation during the balloon inflation time and by lowering the impedance against which the heart pumps during balloon deflation. Balloon deflation removes volume from the aorta just as the left ventricle begins pumping, and an incremental amount of blood is ejected from the left ventricle because of the reduced aortic impedance.

The pioneering cardiovascular surgeon Adrian Kantrowitz devised a permanently implanted counter pulsation system using an intra-aortic balloon equivalent, surgically attached to the descending thoracic aorta or TA. Kantrowitz described his device as an auxiliary mechanical ventricle or AMV. The Kantrowitz device includes a chamber having a flexible membrane that is sewn into the front wall of the TA. A gas conduit traverses the patient's skin to inflate and deflate the TA-appended chamber, producing a beneficial counter pulsation effect.

U.S. Pat. No. 7,347,811 describes a fluid chamber appended to the outside wall of the ascending aorta and having a flexible membrane that, when energized by high pressure fluid, invaginates a portion of the ascending aorta, effectively adding pumped volume to the aorta during diastole. Subsequently, the fluid is withdrawn during early systole to lower the impedance seen by the blood ejecting left ventricle. This counter pulsation device has volume changes in the 20 to 30 milliliter range.

Such counter pulsation devices use electric motors as a first mechanical energy source to pressurize an intermediate fluid that, in turn, pumps blood in the intra-aortic device or the appended fluid chamber. Such expansion drives blood in the aorta through the small vessels of the body.

SUMMARY

In one aspect, an implantable heart assist system, includes a pumping chamber formed of a flexible material and being adapted to be placed in fluid connection with the aorta and a pump system comprising a first rigid member, a second rigid member spaced from the first rigid member so that at least a portion of the pumping chamber may be positioned between the first rigid member and the second rigid member, a drive system comprising a motor, an extending member comprising a threaded section operatively connecting the first rigid member and the second rigid member and a nut in operative connection with the threaded section. The motor is adapted to rotate either the extending member or the nut relative to the other to convert rotary motion of the motor to linear motion to cause the second rigid member to move toward the first rigid member or away from the first rigid member. The heart assist system further includes a controller or a control system in operative connection with the drive system and controlling the motor. Movement of the second rigid member toward the first rigid member results in compression of the pumping chamber, and movement of the second rigid member away from the first rigid member causes expansion of the pumping chamber. The heart assist system may further comprise at least one heart function sensor in operative connection with the controller.

In a number of embodiments, the first rigid member is adapted to be positioned adjacent the chest wall posterior to the thoracic aorta and the second rigid member is adapted to be positioned adjacent the surface of the left lung. The second rigid member may, for example, be adapted to displace a portion of a volume normally occupied by the left lung.

In a number of embodiments, the nut is in operative connection with a rotor of the motor. The extending member may, for example, be connected to the first rigid member in a manner that the orientation of a longitudinal axis of the extending member can change but that the extending member cannot rotate about its longitudinal axis relative to the second rigid member. The motor may, for example, be connected to and move with the second rigid member. In a number of embodiments, a plurality of sliding bearings for the rotor have a hardness of at least Moh's scale 8, and a contact surface of the nut and a surface of the threaded section of the extending member each have a hardness of at least Moh's scale 8. A surface of each of the plurality of sliding bearings may, for example, comprise a diamond material.

A surface of each of the plurality of sliding bearing for the rotor, the contact surface of the nut and the contact surface of the threaded section may, for example, be bathed in an aqueous fluid which is substantially isotonic to blood. The aqueous fluid may comprise a polymer such as a polysaccharide to increase viscosity.

In a number of embodiments, the extending member passes through an open section in the pumping chamber. In a number of embodiments, the drive system is positioned between the first rigid member and the second rigid member within an open area formed in the pumping chamber. In a number of embodiments, the pumping chamber comprises an inlet conduit and an outlet conduit, and the heart assist system further comprises a connector adapted to be placed in fluid connection with the aorta. The connector may, for example, comprise an inlet adapted to be placed in fluid connection with the aorta, a first port in fluid connection with the inlet via a first curved conduit, an outlet adapted to be placed in fluid connection with the aorta, and a second port in fluid connection with the outlet via a second curved conduit. The first port is adapted to be placed in fluid connection with the inlet conduit of the pumping chamber, and the second port is adapted to be placed in fluid connection with the outlet conduit of the pumping chamber. The inlet of the connector and the outlet of the connector may, for example, be positioned such that the connector is adapted to be slid into a lumen of the thoracic aorta between two adjacent sets of inter-costal arteries so that the inlet of the connector and the outlet of the connector occupy a volume occupied by the thoracic aorta before placing the connector in fluid connection with the thoracic aorta. In a number of embodiments, a rearward side of the connector, which is adapted to face a rearward side of the thoracic aorta upon placing the connector in fluid connection with the thoracic aorta, is no greater than 0.0191 meters in height. The inlet of the connector and the outlet of the connector may, for example, be placed in fluid connection only via the pumping chamber upon fluid connection of the first port and the inlet conduit and fluid connection of the second port and the outlet conduit.

A biocompatible gel material may, for example, be interposed between the first rigid member and the chest wall such that deformation of the biocompatible gel material accommodates surface form differences between the pump system and the chest wall, thereby minimizing creation of air spaces at a time of implant of the pump system. A lung contacting surface of the second rigid member may, for example, comprises a lubricious coating disposed thereon. The lung contacting surface of the coating may comprise a fluoropolymer.

The heart assist system may further comprise an energy storage system to at least partially offset force on the second rigid member from blood pressure acting on the second rigid member. The energy storage system may, for example, comprise at least one spring. In a number of embodiments, the motor is positioned between the first rigid member and the second rigid member, and the spring encompasses the motor and extends between the first rigid member and the second rigid member. The spring may, for example, be inverted from original conformation to pre-tension the spring to at least partially offset force on the second rigid member from blood pressure acting on the second rigid member.

In a number of embodiments, a stroke volume of the pump system can be varied by the controller by controlling the number of rotations of a rotor of the motor. In a number of embodiments, a full range of motion of the second rigid member toward the first rigid member and a full range of motion of the second rigid member away from the first rigid member are each effected by 2 to 6 rotations of a rotor of the motor.

The heart assist system may further comprise a first mechanical stop mechanism to limit the motion of the second rigid member toward the first rigid member and a second mechanical stop mechanism to limit motion of the second rigid member away from the first rigid member. The first mechanical stop mechanism and the second mechanical stop mechanism may comprise an elastomeric material to absorb energy.

In a number of embodiments, the pumping chamber is adapted to be placed in connection with the thoracic aorta, and the thoracic aorta forms a portion of the pumping chamber. The pumping chamber may, for example, comprise a chamber section attached to the thoracic aorta which extends radially outward beyond a radial position of a native thoracic aorta wall to which it is attached.

In a number of embodiments, the pumping chamber comprises an inlet conduit adapted to be placed in fluid connection with the thoracic aorta at a first position and an outlet conduit adapted to be placed in fluid connection with the thoracic aorta at a second position which is below the first position.

In a number of embodiments, movement of the second rigid member relative to the first rigid member is controlled such that the volume within the pumping chamber is decreased early in diastole and the volume within the pumping chamber is increased in at least one of late in diastole or early in systole.

In a number of embodiments, the pumping chamber is attached to the first rigid member on a first side of the pumping chamber and the pumping chamber is attached to the second rigid member on a second side of the pumping chamber. The pumping chamber in any embodiment hereof may, for example, comprise a biocompatible, flexible polymer.

In another aspect, a method of assisting a patient's heart, comprises implanting a heart assist system by placing a pumping chamber thereof which is formed of a flexible material in fluid connection with the aorta. The heart assist system further comprises a pump system comprising a first rigid member, a second rigid member spaced from the first rigid member so that at least a portion of the pumping chamber may be positioned between the first rigid member and the second rigid member, a drive system comprising a motor, an extending member including a threaded section connecting the first rigid member to the second rigid member, and a nut in operative connection with the threaded section, the motor being adapted to rotate one of the extending member or the nut relative to the other to convert rotary motion of the motor to linear motion to cause the second rigid member to move toward the first rigid member or away from the first rigid member, and a controller in operative connection of the drive system and controlling the motor, wherein movement of the second rigid member toward the first rigid member results in compression of the pumping chamber and movement of the second rigid member away from the first rigid member causes expansion of the pumping chamber. The method further comprises controlling the motor via the controller to move the second rigid member toward and away from the first rigid member.

In another aspect, a method of placing an implantable heart assist device in operative connection with the aorta without placing a patient on cardiopulmonary bypass during implantation comprises using a template to mark a first area of the aorta for incision; clamping a first longitudinally extending section of the aorta to encompass the marked first area of the aorta in a manner to provide blood flow through an adjacent extending section of the aorta after clamping; forming a first incision in the aortic wall of the clamped first longitudinally extending section of the aorta; connecting a first connective conduit to the first incision; and connecting a pumping chamber of a heart assist device in fluid connection with the first connective conduit. The method may further comprise using the template to mark a second area of the aorta for incision; clamping a second longitudinally extending section of the aorta to encompass the marked second area of the aorta in a manner to provide blood flow through an adjacent extending section of the aorta after clamping; forming a second incision in the aortic wall of the second clamped longitudinally section of the aorta; connecting a second connective conduit to the second incision; and placing the pumping chamber of the heart assist device in fluid connection with the second connective conduit. The first clamped longitudinally extending section of the aorta may, for example, be a longitudinally extending section of the thoracic aorta.

In another aspect, an implantable heart assist system comprises a variable volume pumping chamber for pumping blood in blood sealing attachment to the aorta, at least one movable member which is substantially rigid to expand and contract the pumping chamber, an electrically powered rotary motor comprising a rotor, a mechanical linkage connected between the rotor and the at least one movable member, wherein a first direction of rotor rotation drives the at least one movable member to compress the pumping chamber and a second direction of rotor rotation, opposite the first direction of rotor rotation, expands the pumping chamber, and at least one heart function sensor to sense timing indicia of a heart blood-filling phase or diastole and timing indicia a heart blood-ejection phase or systole. In a number of embodiments, a sensed beginning of heart diastole is used to time pumping chamber compression and a sensed beginning of heart systole is used to time pumping chamber expansion.

In another aspect, an implantable heart assist system comprises a variable volume, flexible pumping chamber for pumping blood adapted to be placed in blood sealing attachment with the aorta, and a pump system comprising a first rigid member, a second rigid member spaced from the first rigid member so that at least a portion of the pumping chamber may be positioned between the first rigid member and the second rigid member, a drive system comprising a motor, an extending member including a threaded section connecting the first rigid member to the second rigid member, and a nut in operative connection with the threaded section. The motor is adapted to rotate either the extending member or the nut relative to the other to convert rotary motion of the motor to linear motion to cause the second rigid member to move toward the first rigid member or away from the first rigid member, a controller in operative connection of the drive system and controlling the motor. Movement of the second rigid member toward the first rigid member results in compression of the pumping chamber and movement of the second rigid member away from the first rigid member causes expansion of the pumping chamber. The implantable heart assist system may further include an energy storage system to at least partially offset force on the second rigid member from blood pressure acting on the second rigid member.

In another aspect, a system for use with an implantable heart assist system including an internal coil, comprises a wearable external system comprising an external coil adapted to transmit energy to the internal coil inductively and an external controller comprising a power source and a control system, the external controller being in wired connection with the external coil; and an elastic vest adapted to be worn by a patient and to removably support the external system so that the external coil is aligned with the internal coil. The elastic vest may, for example, include a controller pocket in the back thereof to removably support the external controller generally centrally on the patient's back and an external coil pocket to removably support the external coil so that the external coil is aligned with the internal coil. In a number of embodiments, the external system further comprises a patient interface comprising a display in wired connection with the external controller, and the elastic vest further comprises a patient interface pocket to removably support the patient interface. The external wearable system in a number of embodiments weighs no more than 3 pounds. The external controller may, for example, be no more than 1 inch thick at any point. In a number of embodiments, the vest is adjustable to alter a position of the external coil relative to the internal coil.

In another aspect, a system for use with an implantable heart assist system comprising an internal coil comprises a plurality wearable external systems, each wearable external system comprising an external coil adapted to transmit energy to the internal coil inductively and an external controller comprising a rechargeable battery system, a wireless communication system and a control system, the rechargeable battery system, the wireless communication system and the control system being integrated within an external controller housing, the external controller being in wired connection with the external coil; and a patient base station comprising a patient base station control system, a patient base station communication system and at least a first patient base station coil adapted to transmit energy to the external coil of any one of the plurality of wearable external system to recharge the rechargeable battery system thereof. The patient base station may, for example, comprise a second patient base station coil adapted to transmit energy to the external coil of any one of the plurality of wearable external system to recharge the rechargeable battery system thereof. In a number of embodiments, the patient base station comprises a first seating to seat any one of the plurality wearable external systems such that the external coil thereof is aligned with the at least a first patient base station coil and a second seating to seat any one of the wearable external systems such that the external coil thereof is aligned with at least a first patient base station coil. In a number of embodiments, the patient base station comprises a first seating to seat any one of the plurality wearable external systems such that the external coil thereof is aligned with the at least a first patient base station coil and a second seating to seat any one of the wearable external systems such that the external coil thereof is aligned with the second patient base station coil.

In a number of embodiments, the system comprises at least three wearable external systems. The patient base station may, for example, be adapted to seat two of the plurality of wearable external systems simultaneously. In a number of embodiments, a wireless communication between the patient base station and the plurality of external wearable systems is used to control charging. Each of the plurality of wearable systems may further comprise a patient interface comprising a display. In a number of embodiments, communication between a worn one of the plurality of wearable external systems and the patient base station is used to provide information to the patient regarding exchange of the worn one of the plurality of wearable external systems with another one of the plurality of wearable external systems.

The system may further comprise a portable case in which the patient base station and two of the plurality of wearable external systems are housable. The portable case may, for example, have dimensions no great than 56 cm by 35 cm by 23 cm. In a number of embodiments, the patient base station is integral to the portable case. In a number of embodiments, the portable case comprises compartment to house other accessories for the system.

The system may further comprise a plurality of elastic vests adapted to be worn by a patient and to removably support one of the plurality of external systems so that the external coil thereof is aligned with the internal coil. In a number of embodiments, each of the plurality of the elastic vests includes a controller pocket in the back thereof to removably support the external controller of a worn one of the plurality of wearable external systems generally centrally on the patient's back and an external coil pocket to removably support the external coil of the worn one of the plurality of wearable external systems so that the external coil of the worn one of the plurality of wearable external systems is aligned with the internal coil.

The implantable heart assist system may, for example, further comprise an internal communication system and the communication system of each of the wearable external systems may be adapted to communicate wirelessly with the internal communication system and wirelessly with the patient bases station communication system. The patient base station communication system may, for example, be adapted to communicate wirelessly with the internal communication system. In a number of embodiments, the patient base station communication system is adapted to communicate with at least one of a physical interface or a manufacturer interface. In a number of embodiments, the patient base station further comprises a memory system in operative connection with the control system to store data regarding the at least one of the implantable heart assist system of the plurality of wearable external systems.

In a number of embodiments, the external controller and the external coil of each of the wearable external systems are in wired connection without any intervening electrical connector that is disconnectable by the patient. Moreover, no wired connection may be required between the patient base station and each of the plurality of wearable external systems in a number of embodiments.

In another aspect, an external wearable system for use in connection with an implanted ventricular assist system including an internal coil and an internal communication system comprises an external coil adapted to transmit energy to the internal coil inductively and an external controller comprising a rechargeable battery system, a wireless communication system and a control system, the rechargeable battery system, the wireless communication system and the control system being integrated within an external controller housing, the external controller being in wired connection with the external coil without any intervening electrical connector that is disconnectable by the patient, and the rechargeable battery system being rechargeable inductively via the external coil.

In another aspect, a patient base station is provided for use with an implantable heart assist system including an internal coil, and internal control system and an internal communication system, and a plurality wearable external systems wherein each wearable external systems includes an external coil adapted to transmit energy to the internal coil inductively and an external controller comprising a rechargeable battery system, a wireless communication system and a control system, the rechargeable battery system, the wireless communication system and the control system being integrated within an external controller housing, the external controller being in wired connection with the external coil. The patient base station comprises a patient base station control system, a patient base station communication system and at least a first patient base station coil adapted to transmit energy to the external coil of any one of the plurality of wearable external system to recharge the rechargeable battery system thereof.

In another aspect, an implantable heart assist system, comprises a pumping chamber formed of a flexible material, the pumping chamber comprising an inlet conduit adapted to be placed in fluid connection with the aorta and an outlet conduit adapted to be placed in fluid connection with the aorta; and a pump system comprising a first rigid member, and a second rigid member spaced from the first rigid member so that at least a portion of the pumping chamber may be positioned between the first rigid member and the second rigid member, a drive system comprising a motor, the motor being positioned between the first rigid member and the second rigid member. The pumping chamber is formed to extend around at least a portion of the motor. The implantable heart assist system, further comprises an extending member including a threaded section operatively connecting the first rigid member and the second rigid member, and a nut in operative connection with the threaded section. The motor is adapted to rotate either the extending member or the nut relative to the other to convert rotary motion of the motor to linear motion to cause the second rigid member to move toward the first rigid member or away from the first rigid member. The implantable heart assist system further comprises a controller in operative connection with the drive system and controlling the motor. Movement of the second rigid member toward the first rigid member results in compression of at least a portion of the pumping chamber and movement of the second rigid member away from the first rigid member causes expansion of the at least a portion of the pumping chamber.

The heart assist system may further comprise a connector adapted to be placed in fluid connection with the aorta and comprising an inlet adapted to be placed in fluid connection with the aorta, a first port in fluid connection with the inlet via a first curved conduit, an outlet adapted to be placed in fluid connection with the aorta, and a second port in fluid connection with the outlet via a second curved conduit. The first port is adapted to be placed in fluid connection with the inlet conduit of the pumping chamber, and the second port being is to be placed in fluid connection with the outlet conduit of the pumping chamber.

In another aspect, an implantable heart assist system comprises a pumping chamber formed of a flexible material, the pumping chamber comprising an inlet conduit adapted to be placed in fluid connection with the aorta and an outlet conduit adapted to be placed in fluid connection with the aorta, and a connector adapted to be placed in fluid connection with the aorta. The connector comprises an inlet adapted to be placed in fluid connection with the aorta, a first port in fluid connection with the inlet via a first curved conduit, an outlet adapted to be placed in fluid connection with the aorta, and a second port in fluid connection with the outlet via a second curved conduit. The first port is in fluid connection with the inlet conduit of the pumping chamber, and the second port is in fluid connection with the outlet conduit of the pumping chamber.

The heart assist system may further comprise a pump system comprising a first rigid member, a second rigid member spaced from the first rigid member so that at least a portion of the pumping chamber may be positioned between the first rigid member and the second rigid member, a drive system comprising a motor, the motor being positioned between the first rigid member and the second rigid member, the pumping chamber being formed to extend around at least a portion of the motor, an extending member including a threaded section operatively connecting the first rigid member and the second rigid member, and a nut in operative connection with the threaded section, the motor being adapted to rotate either the extending member or the nut relative to the other to convert rotary motion of the motor to linear motion to cause the second rigid member to move toward the first rigid member or away from the first rigid member, and a controller in operative connection with the drive system and controlling the motor, wherein movement of the second rigid member toward the first rigid member results in compression of at least a portion of the pumping chamber and movement of the second rigid member away from the first rigid member causes expansion of the at least a portion of the pumping chamber. The second rigid member may, for example, be adapted to compress the pumping chamber in a first section thereof and a second section thereof, the first section and the second section being adjacent opposing sides of the motor.

In another aspect, a method of placing an implantable heart assist device in operative connection with the aorta without placing a patient on cardiopulmonary bypass during implantation, the implantable heart assist device including a pumping chamber, the pumping chamber including an inlet conduit and an outlet conduit, comprises: clamping a first longitudinally extending section of the aorta; forming an incision in the aortic wall of the clamped first longitudinally extending section of the aorta; connecting a connector to the incision, the connector comprising an inlet adapted to be placed in fluid connection with the aorta, a first port in fluid connection with the inlet via a first curved conduit, an outlet adapted to be placed in fluid connection with the aorta, and a second port in fluid connection with the outlet via a second curved conduit, the first port being in fluid connection with the inlet conduit of the pumping chamber and the second port being in fluid connection with the outlet conduit of the pumping chamber; and sliding the connector into a lumen of the aorta to place the inlet of the connector and the outlet of the connect into fluid connection with the aorta. In a number of embodiments, the implantable heart assist device is placed in operative connection with the thoracic aorta and the connector is slid into the lumen of the thoracic aorta between two sets of inter-costal arteries. In a number of embodiments, the inlet of the connector and the outlet of the connector are positioned such that the connector is adapted to be slid into a lumen of the thoracic aorta between two adjacent sets of inter-costal arteries so that the inlet of the connector and the outlet of the connector occupy a volume occupied by the thoracic aorta before placing the connector in fluid connection with the thoracic aorta.

In another aspect, a surgically implantable connector system comprises a first conduit section comprising a flange extending radially outward from a first end thereof, a second conduit section comprising a flange extending radially outward from a first end thereof and an expandable ring adapted to seat the flange of the first conduit section and the flange of the second conduit section therein to form a sealed engagement therebetween. The flange of the first conduit section and the flange of the second conduit section may, for example, be beveled. In a number of embodiments, the expandable ring comprises an angled groove within which the flange of the first conduit section and the flange of the second conduit section are captured.

In another aspect, a method of positioning an implanted internal coil of an implanted heart assist system within a patient comprises having a patient don a garment adapted to support and position an external coil adapted to transmit energy inductively to the internal coil, the external coil being supported by the garment; marking the position of the external coil as supported by the garment on the patient skin; and implanting the internal coil to align with the marked position of the external coil. The approximate center of the external coil as supported by the garment may, for example, be marked.

In a number of embodiments hereof, external coils for use in connection with implanted internal coils comprise a seating formed in the shape of a raised area in the skin of the patient resulting from the internal coil such that the seating cooperates with the raised area to align the external coil with the internal coil.

In another aspect, an implantable heart assist device includes a chamber section formed of a flexible material and having an opening. The opening of the chamber section is adapted to be placed in fluid connection with the aorta via a blood tight seal to form a pumping chamber through which blood flows. The heart assist device further includes a pump or pump system comprising a first rigid member, a second rigid member spaced from the first rigid member, and a drive system operatively connected to move at least one of the first rigid member or the second rigid member toward the other and to move at least one of the first rigid member or the second rigid member away from the other. The heart assist device further includes a controller in operative connection of the drive system. The controller (that is, an implantable or internal controller) controls motion of at least one of the first rigid member and the second rigid member relative to the other. The second rigid member is spaced from the first rigid member such that the pumping chamber may be positioned between the first rigid member and the second rigid member. Movement of at least one of the first rigid member or the second rigid member toward the other results in compression of the pumping chamber, and movement of at least one of the first rigid member or the second rigid member away from the other causes expansion of the pumping chamber. In a number of embodiments, the drive system includes a motor. The heart assist device may, for example, further include a heart function sensor in operative connection with the controller. The controller may, for example, include circuitry and/or one or more processors (for example, microprocessors).

In another aspect, a method of providing pump assist to the heart, includes: placing a chamber section in blood tight, sealing connection with the aorta to form a pumping chamber through which blood flows; providing a pump system in operative connection with the pumping chamber, the pump system including a first rigid member, a second rigid member spaced from the first rigid member, and a drive system operatively connected to move at least one of the first rigid member or the second rigid member toward the other and to move at least one of the first rigid member or the second rigid member away from the other; and a controller in operative connection of the drive system and controlling motion of at least one of the first rigid member and the second rigid member relative to the other, wherein the pumping chamber is positioned between the first rigid member and the second rigid member, moving at least one of the first rigid member or the second rigid member toward the other to compress the pumping chamber; and moving at least one of the first rigid member or the second rigid member away from the other to expand the pumping chamber.

In another aspect, a method of placing an implantable heart assist device in operative connection with the aorta without placing a patient on cardiopulmonary bypass during implantation, includes: clamping a longitudinally extending section of the aorta in a manner to provide blood flow through an adjacent extending section of the aorta after clamping; forming an incision in the aortic wall of the clamped section of the aorta; connecting a first edge of an intermediate section to incised aortic wall, the intermediate section including a second edge to which a sealing connector is attached; connecting a chamber section to the sealing connector via a cooperating sealing connector attached to an opening of the chamber section, wherein the aorta, the intermediate section and the chamber section form a blood tight pumping chamber through which blood flows; and placing a pump system in operative connection with the chamber section such that the pump system is operable to or adapted to compress and expand the pumping chamber. In a number of embodiments, the clamped section of the aorta is a longitudinally extending section of the thoracic aorta.

In another aspect, an implantable heart assist device includes a variable volume pumping chamber for pumping blood in blood sealing attachment to the aorta, at least one movable member which is substantially rigid to provide for expansion and contraction of the pumping chamber, an electrically powered rotary motor including a rotor, and a mechanical linkage connected between the rotor and the movable member. A first direction of rotor rotation drives the movable member to compress the pumping chamber (reducing its volume). A second direction of rotor rotation, opposite the first direction of rotor rotation, expands the pumping chamber (increasing its volume). The device further includes least one heart function sensor to sense timing indicia of a heart blood-filling phase or diastole and timing indicia a heart blood-ejection phase or systole. The pumping chamber may, for example, be placed in fluid connection with the descending thoracic aorta. A sensed beginning of heart diastole may, for example, be used to time pumping chamber compression and a sensed beginning of heart systole may, for example, be used to time pumping chamber expansion.

In another aspect, a heart assist device includes a variable volume pumping chamber for pumping blood which is adapted to be surgically constructed from a combination of thoracic aortic wall on one lateral side and from an attached chamber section on an opposite lateral side such that, when the chamber section is attached to the thoracic aortic wall, the thoracic aorta wall and the chamber section form a blood-tight seal. The pumping chamber has an entrance lumen formed by the proximal thoracic aortic lumen and an exit lumen formed by the distal thoracic aortic lumen. The device further includes stationary back-side structure positioned against the inner chest wall. The back side structure includes a generally flat and stationary plate in operative connection with the pumping chamber. The device further includes a front-side, movable plate that is generally flat. At least a portion of the pumping chamber is positioned between the stationary plate and the movable plate. When the movable plate is moved toward the stationary plate, the volume of the pumping chamber decreases (via compression). When the movable plate is moved away from the stationary plate, the volume of the pumping chamber increases (via expansion).

In another aspect, an implantable heart assist device includes a variable volume pumping chamber for pumping blood which is adapted to be surgically constructed from the combination of thoracic aortic wall on one lateral side, an intermediate connector section attached to the thoracic aortic wall on a first edge and including connector section on a second edge, and a chamber section including a cooperating connector section on an open edge thereof. When the cooperating connector section of the chamber section is connected to the connector section of intermediate section, the thoracic aorta wall, the intermediate section and the chamber section form a blood-tight pumping chamber for pumping blood. The pumping chamber has an entrance lumen formed by the proximal thoracic aortic lumen and an exit lumen formed by the distal thoracic aortic lumen. The connector section and the cooperating connector section may, for example, form a removable or releasable connection.

In another aspect, an implantable heart assist device for use in connection with an aortic artery of a patient includes a pumping chamber adapted to be placed in fluid connection with the aortic artery to occupy a native position of the aorta and extending radially outward from the native position of the aorta and a pump system in operative connection with the auxiliary pumping chamber. The pump system includes a first rigid member on a first side of the auxiliary pumping chamber, a second rigid member, spaced from the first rigid member on a second side of the auxiliary pumping chamber, and a drive system operatively connected to move at least one of the first rigid member or the second rigid member toward the other to decrease a volume within the pumping chamber and to move at least one of the first rigid member or the second rigid member away from the other to increase the volume within the pumping chamber. The pump system further includes a controller in operative connection of the drive system and being adapted to control motion of at least one of the first rigid member and the second rigid member relative to the other such that the volume within the auxiliary chamber is decreased early in diastole and the volume within the pumping chamber is increased late in diastole and/or early in systole. The pumping chamber may, for example, be formed from a combination of a native thoracic aortic wall and flexible chamber section suitable for blood contact, wherein the native thoracic aortic wall and the flexible chamber section are joined by a blood tight connection.

In another aspect, a ventricular assist system for use in connection with a patient includes an implantable ventricular assist device; an implantable first coil in operative connection with the ventricular assist device; an external second coil adapted to transmit energy to the first coil inductively; an external controller including a power source in operative connection with the second coil; and an elastic vest adapted to position the second coil in operative connection with the first coil when the elastic vest is worn by the patient, the elastic vest further housing the external controller.

In another aspect, a ventricular assist system for use in connection with a patient includes an implantable ventricular assist device; an implantable first coil operative connection with the ventricular assist device; an external second coil adapted to transmit energy to the first coil inductively; an external controller comprising a power source in operative connection with the second coil; and a patient interface adapted to communicate with the external controller wirelessly. The patient interface may, for example, include a display. In a number of embodiments, the patient interface includes a display, a processor and an input system. The patient interface may, for example, include a cellular phone or a smartphone.

In another aspect, a ventricular assist system for use in connection with a patient includes an implantable ventricular assist device; an implantable first coil in operative connection with the ventricular assist device; an external second coil adapted to transmit energy to the first coil inductively; and at least one external controller including at least one battery as a power source in operative connection with the second coil, wherein the at least one battery may be charged inductively. The at least one battery may, for example, be non-removably or non-replaceably enclosed within a housing of the at least one external controller. The at least one battery may, for example, be charged inductively via the second coil. The at least one battery may, for example, be charged inductively via a third coil within a housing of the at least one external controller. In a number of embodiments, the system includes at least three external controllers which may, for example, be interchangeable. The external controllers may, for example, be manufactured to be generally the same or identical.

In a further aspect, a method of placing an implantable heart assist device in operative connection with the aorta without placing a patient on cardiopulmonary bypass during implantation, includes: clamping a longitudinally extending section of the aorta in a manner to provide blood flow through an adjacent extending section of the aorta after clamping and forming incision in the aortic wall of the clamped section of the aorta. The method may, for example, further include attaching a pumping chamber to be in fluid connection with the aorta via the incision. In a number of embodiments, the pumping chamber is surgically created by attaching a chamber section to the incised aortic wall. In a number of other embodiments, a pumping chamber is, for example, placed in fluid connection with the aorta via conduits attached to the aorta via the incision and a second incision therein. In a number of embodiments, a template device may be used to mark the location of the incision(s) on the aortic wall.

In a number of aspects, methods of assisting the heart are provided which include use of any of the heart assist devices or systems hereof or the VAD systems hereof in connection with, for example, the aorta (for example, in connection with the descending thoracic aorta).

The present devices, systems, and methods, along with the attributes and attendant advantages thereof, will best be appreciated and understood in view of the following detailed description taken in conjunction with the accompanying drawings.

BRIEF DESCRIPTION OF THE DRAWINGS

FIG. 2D illustrates a left anterior oblique perspective view of another embodiment of a TA pump hereof attached to a patient's ribs and including a pumping chamber that is placed in parallel with the TA, referred to as a parallel or in-parallel TA pump herein.

FIG. 2E is a perspective view of the TA pump of FIG. 2D and an embodiment of an internal TETS coil located on the left lateral chest wall.

FIG. 2F illustrates a cranial or top perspective view of the TA pump of FIG. 2D.

FIG. 2G illustrates a flow study within a TA pump similar to that of FIG. 2D but without a looped upper conduit in fluid connection with the thoracic aorta and the associated blood recirculation in the pumping chamber with the TA pump in an off state.

FIG. 2H illustrates a flow study of the TA pump of FIG. 2D, including the looped upper conduit, and the associated reduction of blood recirculation in the pumping chamber with the TA pump in an off state.

FIG. 2I illustrates a perspective view of another embodiment of a TA pump, referred to as a circular TA pump, herein attached to the descending thoracic aorta and including a pumping chamber providing for generally circular flow therethrough see FIG. 2M.

FIG. 2J illustrates a front view of the TA pump of FIG. 2I.

FIG. 2K illustrates a cranial or top perspective view of the TA pump of FIG. 2I.

FIG. 2L illustrates an exploded perspective view of the TA pump of FIG. 2I.

FIG. 2M illustrates another front view of the TA pump of FIG. 2I with the front rigid plate removed therefrom.

FIG. 2N illustrates a partially exploded perspective view of the TA pump of FIG. 2I wherein the pumping chamber is in fluid connection with the descending thoracic aorta.

FIG. 3A illustrates a perspective view for a connector for use in connection with the TA pump of FIG. 2I to connect the TA pump to the thoracic aorta.

FIG. 3B illustrates a perspective cutaway view of the connector of FIG. 3A.

FIG. 3C illustrates a front view of the connector of FIG. 3A.

FIG. 3D illustrates a top view of the connector of FIG. 3A.

FIG. 5C illustrates a methodology for identifying the proper location for a surgeon to place the implanted/internal TETS coil to be opposite the location of the external TETS coil as positioned by the elastic vest of FIG. 4.

FIG. 5D illustrates a cross-sectional view of a skin bulge created by the internal TETS coil under the patient's skin and the use of a mechanical "skirt" to assist in maintaining alignment of the external TETS coil with the internal TETS coil.

FIG. 9A illustrates a side cross-sectional view of an embodiment of a swiveling screw connection for an embodiment of a screw-nut actuator hereof, wherein the screw and the back plate of the pump are in a first state or relative position.

FIG. 9B illustrates another side cross-sectional view of the swiveling screw connection of FIG. 9A, wherein the screw and the back plate of the pump are in a second state or relative position, different from the first state of FIG. 9A.

FIG. 9C illustrates an enlarged side, cross-sectional view of a ball socket including a keyway formed in the rear or back rigid plate of a TA pump hereof and a retainer plate.

FIG. 9D illustrates an enlarged side, cross-sectional view of the swivel ball of the swiveling of screw connection of FIG. 9A positioned within the ball socket of the back plate and the retainer plate.

FIG. 11 illustrates a perspective view of an embodiment of a motor and an energy storage mechanism of the TA pump of FIG. 2A in operative connection with the motor.

FIG. 15A illustrates a perspective view of the location of a modified Satinsky clamp in place on the aorta before incision of the aorta in constructing a pumping chamber of the TA pump of FIG. 2A.

FIG. 15B illustrates a perspective view of the location of an aortic incision in the thoracic aorta with the modified Satinsky clamp in place during construction of a pumping chamber of the TA pump of FIG. 2A.

FIG. 16A illustrates an embodiment of a removable or releasable attachment mechanism for the connection of an integral pumping chamber section of the TA pump of FIG. 2A.

FIG. 16F illustrates a perspective view of the mechanical grounding of the pump's back plate extensions for attachment to the ribs using, for example, bone screws.

FIG. 17 illustrates a side cross-sectional view of the pumping chamber and the rigid members or plates of the TA pump of FIG. 1 in operative connection therewith, illustrating the general direction of relative movement between the plates as being generally perpendicular to a radial line extending from the descending thoracic aorta.

FIG. 18A illustrates an embodiment of a methodology using a mechanical template to locate and mark two incisions on the thoracic aortic or TA wall as well as screw holes for attachment of the TA pump of FIG. 2D.

FIG. 18B illustrates the application of two separate Satinsky clamps on the TA for connection purposes of the two conduits of the TA pump of FIG. 2D.

FIG. 18C illustrates aortic incisions having been made after application of the Satinsky clamps as illustrated in FIG. 18B.

FIG. 18D illustrates the sutured attachment of connective conduits, for example, DACRON® conduits, to the TA and, with a "quick" connector hereof attached to each of the connective conduits.

FIG. 18E illustrates the connection of the pumping chamber of the TA pump of FIG. 2D to the TA via the connectors attached to the connective conduits.

FIG. 18F illustrates the connection of the rigid plates and pump motor to the pumping chamber with leads extending to a pacemaker and the internal TETS coil.

FIG. 18G illustrates the assembled TA pump in fluid connection with the thoracic aorta and connection of the TETS lead to the internal TETS coil.

FIG. 19A illustrates a perspective view of an embodiment of a "quick" coupler or connector hereof for effecting relatively quick connection of conduits in which one conduit end is seated within the connector. another conduit end is in alignment for seating in the connector and a connector is in an open or expanded state.

FIG. 19B illustrates a perspective view of the connector of FIG. 19A with both conduit ends seated within the connector and the connector in an open or extended state.

FIG. 19C illustrates a perspective view of the connector of FIG. 19A with both conduit ends seated within the connector and the connector is in a closed or relaxed state to retain the conduit ends in sealed connection.

FIG. 19D illustrates a cross-sectional view of the connector of FIG. 19A with both conduit ends seated within the connector and the connector in a closed or relaxed state to retain the conduit ends in sealed connection.

DETAILED DESCRIPTION

Figure 1A:
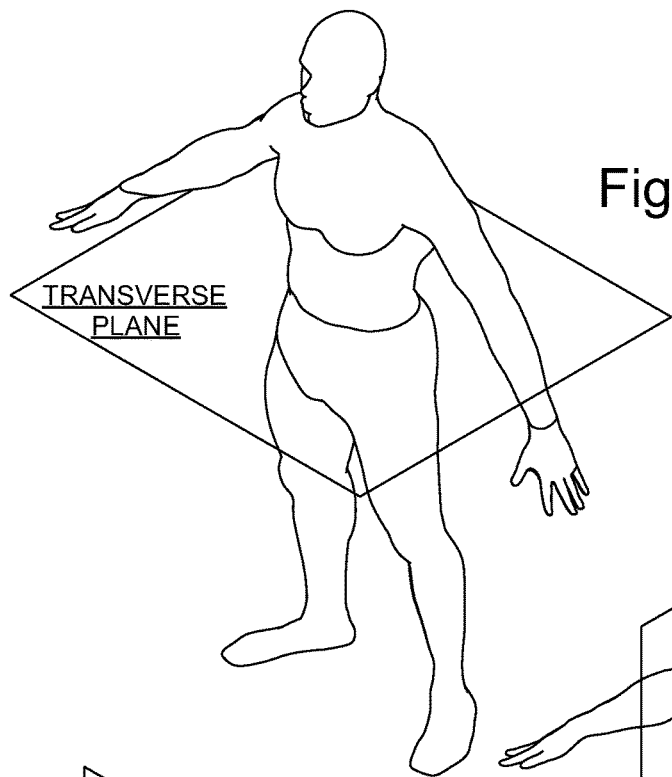
FIG. 1A illustrates a perspective view of a patient showing a representation of the transverse plane.

It will be readily understood that the components of the embodiments, as generally described and illustrated in the figures herein, may be arranged and designed in a wide variety of different configurations in addition to the described representative embodiments. Thus, the following more detailed description of embodiments hereof, as represented in the figures, is not intended to limit the scope of the embodiments, as claimed, but is merely illustrative of representative embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a pumping chamber" includes a plurality of such pumping chamber and equivalents thereof known to those skilled in the art, and so forth, and reference to "the pumping chamber" is a reference to one or more such pumping chamber and equivalents thereof known to those skilled in the art, and so forth. Recitation of ranges of values herein are merely intended to serve as a shorthand method of referring individually to each separate value falling within the range. Unless otherwise indicated herein, and each separate value, as well as intermediate ranges, are incorporated into the specification as if individually recited herein. All methods described herein can be performed in any suitable order unless otherwise indicated herein or otherwise clearly contraindicated by the text.

A number of representative embodiments heart assist devices, systems or pumps are described herein. In a number of embodiments, the heart assist devices, systems or pumps hereof include a variable volume, flexible pumping chamber and a pump system to vary the volume of the pumping chamber to assist in blood flow. The pumping chambers hereof are placed in fluid connection with a blood vessel such as the aorta. In a number of embodiments, the pumping chambers are place in fluid connection with the thoracic aorta or TA and the pumps hereof are sometimes referred to as thoracic aorta pumps or TA pumps. Thus, the term "TA pump" as used herein describes representative embodiments a pump portion of a heart assist ventricular assist device (VAD) or system operatively connected to the descending thoracic aorta. However, pumps or VADs hereof may be positioned elsewhere (for example, in fluid connection with the ascending aorta). Surgery to place the pumps or pump system hereof in connection with, for example, the ascending aorta may be more invasive than in connection with the TA.

In a number representative embodiments, a pumping chamber of a TA pump hereof is constructed (by the implanting surgeon) from an integral combination of aortic wall and synthetic materials. TA pumps including such an integral pumping chamber are sometimes referred to herein as integral TA pumps.

Figure 1B:
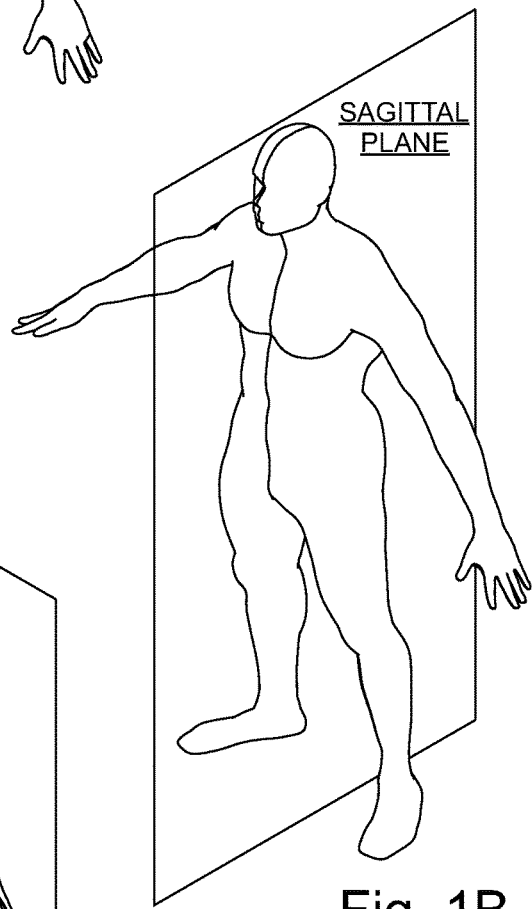
FIG. 1B illustrates a perspective view of a patient showing a representation of the sagittal plane.
Figure 1C:
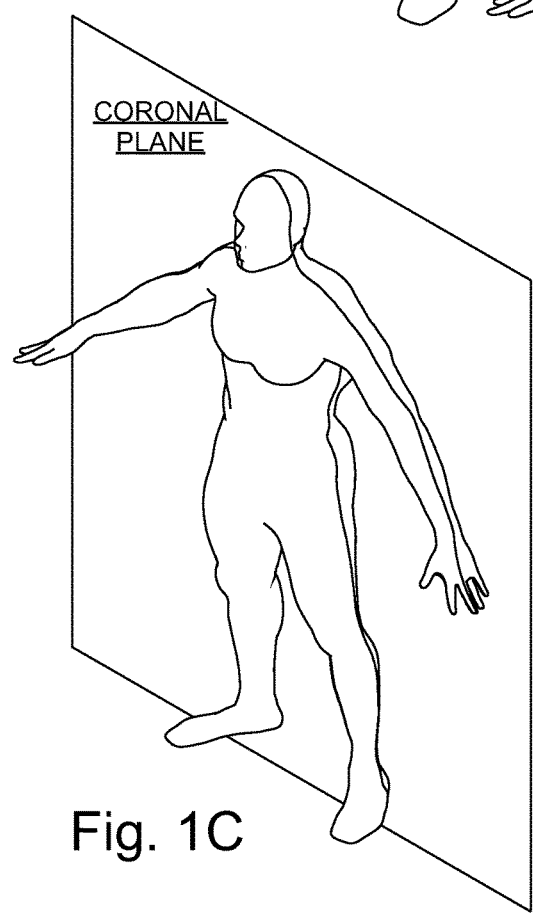
FIG. 1C illustrates a perspective view of a patient showing a representation of the coronal plane.

In other representative embodiments, the pumping chamber of the TA pump is entirely synthetic/In a number of such embodiments, the TA pump is placed in-parallel fluid connection with the thoracic aorta or TA via two conduits. TA pumps including such a pumping chamber placed in parallel with the TA and having fluid connections with the TA are sometimes referred to herein as parallel or in-parallel TA pumps. In a number of embodiments, one of the two conduits of such in-parallel TA pumps connect the TA pump with the thoracic aorta, at level of the aortic arch, while the other conduit connects to the TA at a level just above the diaphragm. Because a description of the placement of the TA pumps hereof in the patient's body involves reference to a number of anatomical terms of the human body related to position and/or orientation, FIGS. 1A, 1B, and 1C, respectively, illustrate the transverse, sagittal and coronal planes of the human body.

In still other representative embodiments, the pumping chamber of the TA pump is entirely synthetic and is placed in series fluid connection with the thoracic aorta or TA via two conduits. In a number of such embodiment, the blood flow from the thoracic aorta, through the pumping chamber, and back to the thoracic aorta is generally circular, and such TA pumps are sometimes referred to herein as circular TA pumps.

The human descending thoracic aorta or TA is a relatively straight blood conduit having a typical diameter of about one inch and a wall thickness of about 2.5 millimeters. The TA runs along the left side of the body and slightly in front of the vertebral column. Immediately behind the TA and slightly toward the left and toward the patient's back is a 1.5 to 3 inch wide lung space that is limited by the inner chest wall. As described above, in a number of representative embodiments, pumps hereof are placed in operative connection with the descending thoracic aorta or TA.

In a number of embodiments of integral TA pump systems described herein, the pump system uses the lung space described above to extend the interior blood volume of the thoracic aorta backwards and slightly to the left, thereby creating an enlarged pumping chamber of the TA pump. By using this combined thoracic aortic and lung space, the exchangeable volume of a number of embodiment of integral TA pumps hereof may, for example, range between approximately 35 and 70 cc (cubic centimeters) depending on the size of the patient. The exchangeable volumes of a number of embodiments of parallel TA pumps hereof are similar to or greater than those described above for integral TA pump.

To help the patient's weak left ventricle pump more blood, the pumping chambers hereof may be alternatively mechanically collapsed and then expanded by the movement of a substantially rigid front plate pressing against the pumping chamber. As used herein, the term plate refers to a substantially rigid member which retains its shape under the forces of use thereof. In a number of representative embodiments, plates or rigid members hereof are generally flat or slightly curved throughout the stroke, movement thereof, at least on the side thereof in operative connection the pumping chamber. The TA pumps hereof cause compression of the pumping chamber during the heart's filling time or diastole and cause expansion of the pumping chamber during ventricular contraction time or systole. During diastolic heart filling, the TA pumps hereof increase the aortic pressure, which drives more blood to the body. During systolic ventricular contraction, the expansion of the pumping chambers of the TA pumps hereof lowers aortic pressure, making it easier for the ventricle to eject blood. This form of heart assist is termed counter pulsation, because the level of the usual pressure pulses are reversed.

In a number of embodiments, the TA pump includes electrocardiograph (ECG) and/or heart sound sensing capabilities to time its collapsing and expanding volumetric changes. In a number of embodiments, the volume change of the TA pump requires no compliance chamber because the lung tissue fills any vacated space created by the front plate moving against and into the TA pump's pumping chamber space.

In a number of embodiments, systems hereof include a number of devices that cooperatively function as a counter pulsation assist systems. In a number of embodiments, in addition to the TA pump, other components of the assist system may, for example, include an implanted electronic "internal control unit" or controller, a combination of an implanted coil and an external coil which form a "transcutaneous electrical transmission subsystem" or "TETS", and an "external controller". The external controller or controller may, for example, include a plurality of batteries. The system may, for example, include a handheld patient interface/display, and an external controller recharging and storage unit, sometimes referred to herein as a base unit or patient base station.

Pumps hereof reduce or eliminate a number of risks associated with previous VADs. For example, shear-related blood damage, with resulting strokes and bleeding, is reduced or eliminated because the TA pumps hereof push blood as opposed to the shear inducing, blood slicing motion of the impeller blades of rotary VADs. Moreover, the risk of infection, is greatly reduced by using a TETS, thereby eliminating any driveline that punctures the skin and provides a path for invading micro-organisms. Instead, the TETS uses a pair of coils, one outside the skin and one inside the skin that are inductively coupled without puncturing the skin. The TETS provides the electrical energy for driving, for example, a DC torque motor of the TA pump. U.S. Patent Publication No. 2013/0289334, the disclosure of which is incorporated herein by reference, describes the use of TETS and control protocols for the use of TETS which may readily be adapted for use herein. Further, the pumps hereof are failsafe and will not risk patient death in the event of power loss. In that regard, the pumps hereof are placed in series with the heart rather than being placed in parallel with the heart. Without power, the pumps hereof become a passive pathway for blood travelling from the heart to the body. The pumps hereof may thus have a "normally open state" wherein the pump provides an open fluid path through which blood can freely travel even without powering the pump. With power loss, and barring unforeseen risks, the patient will be at no greater risk than if the pump was not present.

All blood contacting surfaces of the TA pumps hereof may, for example, be coated with a material to improve blood compatibility such as a 2-methacryloyloxyethyl phosphorylcholine MPCP polymer material such as, for example, available from the NOF America Corporation of White Plains, N.Y. MPC is a naturally occurring chemical found on the surface of human cells and is very resistant to protein adherence and clot formation.

The interface between the rigid members or plates and the flexible membrane of the chamber section and/or aortic wall of the blood pumping chamber may, for example, be adhesively connected, connected by one or more connectors or left unconnected. In cases wherein the pumping chamber is left unconnected to the rigid member or plates, the blood pressure of blood within the pumping chamber, which is always greater inside the pumping chamber than outside the chamber, will continuously force the flexible membrane or aortic wall against, directly or indirectly into operative connection with the rigid members or plates.

In a number of embodiments, the method by which a TA pump hereof contracts and expands its associated pumping chamber volume is by reciprocal linear movement of the pump's movable front plate toward and then away from the stationary back plate. Alternatively, the back plate could be moved relative to a stationary front plate or both plates could be moved. In a number of such embodiments, a compliance volume may be required.

In a number of embodiments of TA pumps hereof, the actuator for relatively movement of one or more rigid plates is the motor's rotor in combination with a screw-nut actuator mechanism operatively connecting the rigid plates. The motor's rotor may, for example, be connected to a nut which acts on an extending member including a threaded section (sometimes referred to herein as a screw) that is mechanically grounded to the back plate. Rotary motion of the rotor is thereby converted into linear motion of the front plate. Thus, rotation of the rotor in one direction closes the space between the plates, and rotation of the rotor in the opposite direction opens the space between the plates. Examples of screw-nut actuator combinations are, for example, available from Thomson Industries, Inc. of Radford, Va.

The size and weight of the torque motor may, for example, be desirably minimized by using the mechanical advantage of the screw. For example, 2 to 6 rotations of the rotor may be used to move the outside (lung side) plate one half inch toward the stationary plate in a closing or pumping direction. If the pitch of the screw is 0.125 inches, a one half inch closing motion will be effected by four turns of the rotor. With a small patient, the effective surface area of the moving plate may, for example, be 35 $cm^2$ or 5.4 $in^2$. The blood work performed with a one half inch stroke is equal to the force multiplied by the distance of travel. If the average aortic blood pressure is 2.5 pounds per square inch (PSI) or 130 mmHg during the early diastolic pumping stroke, the force will be equal to 2.5 $lb/in^2 \times 5.4$ $in^2$ or 13.6 pounds force. Thus, the work is 13.6 pounds force times 0.5 in or 6.8 pound-inches of work. The motor's rotor will have rotated 6.28 radians per revolution, and four revolutions will yield 4 times 6.28 or 25.1 radians of rotation. Converting 6.8 pound-inches to ounce-inches yields 109 ounce-inches. Dividing this value by 25.1 radians yields the required rotor torque of 4.34 ounce-inches for plate closing movement, neglecting friction. The volume of blood pumped per stroke may, for example, be increased or decreased (that is, be controlled) through, for example, software control of the number of motor rotor rotations. Closed loop control of assist volumes may, for example, be implemented. For example, higher pump stroke volumes could be linked to higher natural heart rates.

In a number of embodiments, the screw connection to the back plate is such that the screw can swivel, that is, the longitudinal axis thereof may change its orientation about the point of connection—similar to precession, but the screw cannot rotate about its longitudinal axis relative to the back plate. The screw's inability to rotate enables the rotating nut to force the front plate toward and away from the stationary back plate. The screw's ability to swivel relieves potential torsion forces on the nut-screw joint that would otherwise occur if the screw were unable to swivel.

An embodiment of a balanced mechanical arrangement for activating the front VAD plate to move toward and away from the back plate is to have the screw and nut combination hereof located generally at approximately the center of mass of the plates. For example, the longitudinal axis of the screw can be within 15%, 10%, 5% or even less of the center of mass or centroid of each plate. An alternative actuating mechanism may, for example, include one or more actuating devices that are positioned around the outside edges of the pumping chamber which force the plates together and allow the blood pressure to push them apart. However, this arrangement is more complicated and bulky than using a centralized or approximately centralized screw-nut mechanism.

As the actuating mechanism is centralized of approximately centralized, in a number of embodiments the pumping chamber hereof, which are positioned between the rigid plates of the TA pumps hereof, are formed with, or around, an open section or void volume though which an actuating mechanism such as the extending threaded member/screw of a screw-nut mechanism passes to operatively connect the rigid plates. In a number of embodiments, the pumping chamber is formed with an interior hole, similar to a hole in a torus or a doughnut hole, though which the extending threaded member of a screw-nut mechanism passes. The pumping chambers hereof are not necessarily circular in shape, however. A bellows may, for example, be formed in the wall of the pumping chamber surrounding the extending threaded member. A bellows such as a biocompatible, polyurethane bellows is well suited to protect the actuating mechanism from blood contact and withstand repeated cyclic compression/expansion over extended periods of time. In other embodiments hereof, a pumping chamber may be shaped to have a flow path that is generally open O-shaped, U-shaped or horseshow shaped, with extending inlet and outlet conduits and a compression/expansion volume. The actuating mechanism passes through the interior open section or void volume of the pumping chamber. In a number of such embodiment, the motor and the actuating mechanism may be positioned within the interior open section or void volume and between the rigid plates.

The size of the pump's blood or pumping chamber and its pumping volume may, for example, vary according to pump sizes designed for various patient body sizes. The pumping volume may also be varied by the distanced traveled by the front plate relative to the back plate. That distance may, for example, be determined by software controlling the number of rotor/nut rotations. In a number of embodiments, the pumping chamber includes a generally flat or modestly curved front plate, and a generally flat or modestly curved back plate.

In a number of embodiments, the surface of the pump facing the lung may be coated with lubricious material, for example, a perfluoropolymer such a polytetrafluoroethylene. In that regard, during breathing, the lung surface should easily slide across the pump's lung side surface. The backside of the pump may, for example, be formed from a rigid material such as a titanium sheet or plate, which adds structure to the pump's back side, which faces the rear chest wall. A compliant material such as a silicone gel as well as a small compliance chamber for intrabellow fluid exchange may, for example, be also used to fill any space between the chest wall and the pump's back plate.

It is well known that rolling element steel bearings such as ball bearings are very energy efficient. However, such bearings cause various amounts of noise and vibration. If implanted, rolling element steel bearings could be undesirably sensed by the patient. There are a number of ways to provide a bearing function while minimizing or eliminating such noise and vibration. For example, polymeric races may be used in rolling element bearings. Examples of suitable polymeric materials include, but are not limited to poly (ether ketone) (PEEK) polymers or hard polyurethanes. However, such materials may have a limited life. Alternatively, the thrust and radial bearings of the rotor may include sliding surfaces without intermediate rolling elements. To minimize wear and friction, these bearing surfaces may, for example, be constructed from very hard materials. Such material may, for example, exhibit a Moh's scale hardness of 8 or higher. One of the hardest possible sliding bearing material surface is a diamond-coated surface such as diamond-coated titanium or diamond-coated silicon carbide, which may, for example, have a hardness of 10 on the Moh's scale. A surface such as ultra-nano-crystalline diamond or UNCD, available, for example, from Advanced Diamond Technologies of Romeoville, Ill. or Vista Engineering of Birmingham, Ala., may be vapor deposited on titanium to construct rotor washer-shaped thrust bearings. A smooth diamond surface sliding on diamond or smooth silicon carbide surface may, for example, exhibit a coefficient of friction or COF below 0.1 Experimental studies have shown that hand polishing with rouge on a high speed buffing wheel can result in an average surface roughness/smoothness of approximately 11 micro-inches (0.275 micro-meters) compared with 20 to 30 micro-inches (0.5 to 0.75 micro-meters) achieved with electro or chemical polishing. As a rule, the more smooth a surface is, the lower the COF. If the pump bearing surfaces become hydrodynamic, essentially no wear will occur, and the COF can be below 0.01. Since a gaseous fluid in the body is unstable over time as a result of diffusion, a liquid fluid may be used to bath the thrust bearings and the nut screw bearing.

Pumping Chambers

Figure 2A:
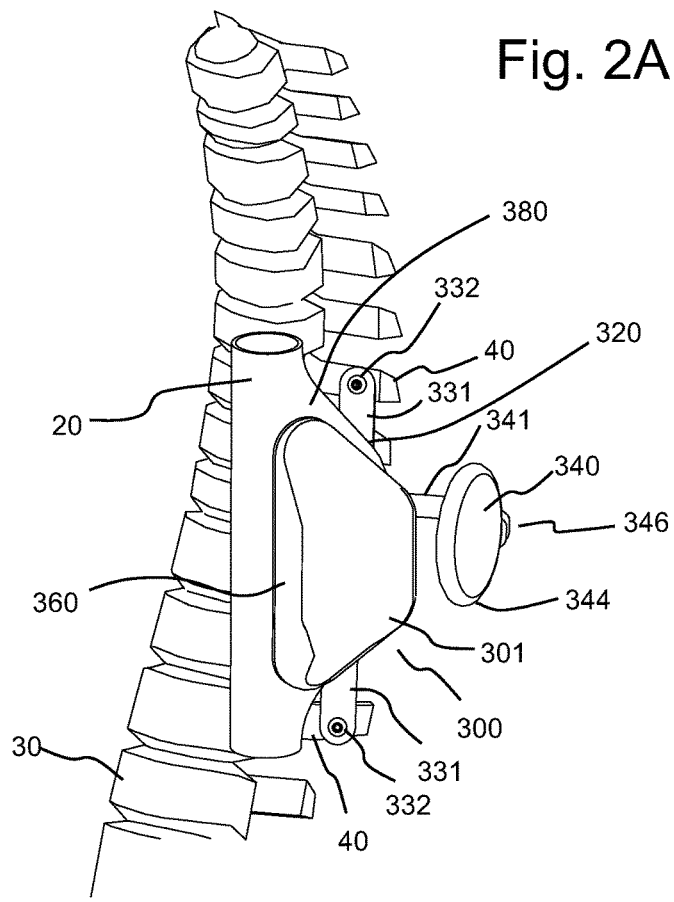
FIG. 2A illustrates a left anterior oblique perspective view of an embodiment of a thoracic aorta pump or TA pump hereof attached to a patient's ribs and including a pumping chamber that is integral with the thoracic aorta, referred to herein as an integral TA pump.
Figure 2B:
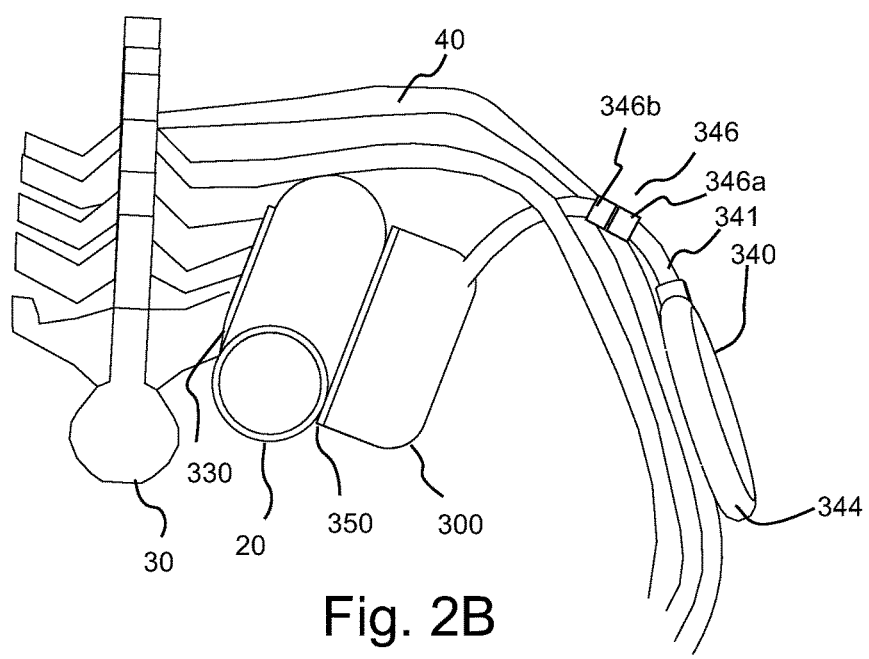
FIG. 2B illustrates a cranial or top perspective view of the TA pump of FIG. 1.
Figure 2C:
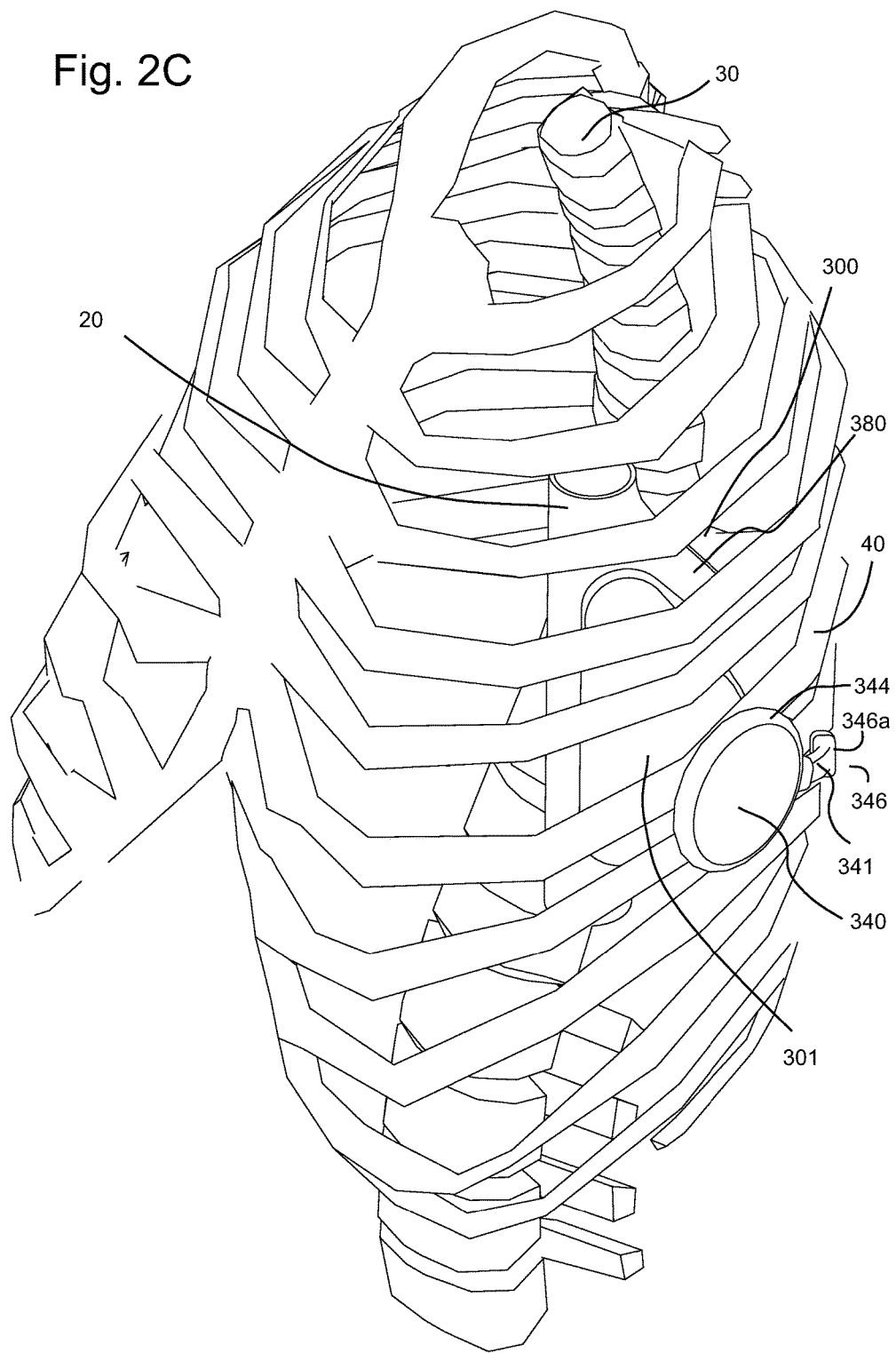
FIG. 2C is a perspective view of an embodiment of an internal TETS coil located on the left lateral chest wall under the skin.

FIGS. 2A through 2C illustrate the location of an embodiment of an integral TA pump 300 in the body. Integral pumping or blood chamber 380 FIG. 16 is formed from a combination of the thoracic aorta lumen, front and back intermediate sections 150, and the additional volume within an appended, membranous chamber section 320, which may, for example, be formed from a biocompatible polymer such as a polyurethane. The normal diameter of the thoracic aorta 20 is approximately one inch and the cross sectional area is therefore approximately 5 cm$^2$. When integral pumping chamber 380 of the TA pump 300 is formed by the added chamber section or bag structure 320, the pumping chamber cross sectional area may, for example, be increased to a range of 12 to 20 cm$^2$, depending, for example, on the size of TA pump 300 chosen for a particular patient size. Chamber section 320 includes a passage or hole 312' (see FIG. 16D) formed therein with a bellows 312 formed in the wall thereof through which an extending threaded member 520 of the actuating mechanism passes.

Figure 16B:
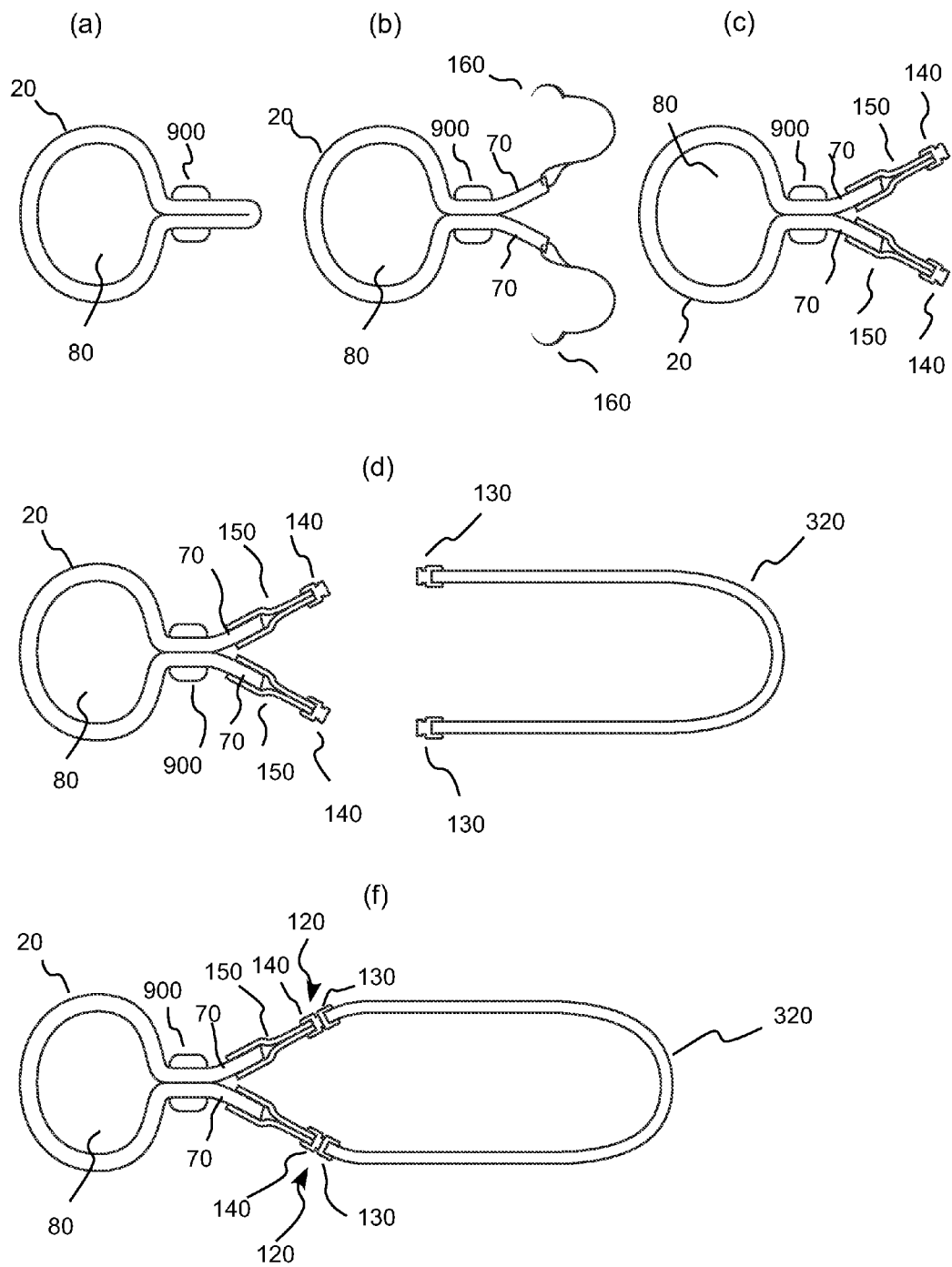
FIG. 16B illustrates a side view of several stages or actions of an embodiment of a procedure for attachment of an intermediate connector section including a releasable attachment mechanism on one edge and a connector section to the incised lips of the thoracic aorta on the other edge and for the subsequent attachment of a chamber section of the TA pump of FIG. 2A thereto to form the pumping chamber of the TA pump.
Figure 16C:
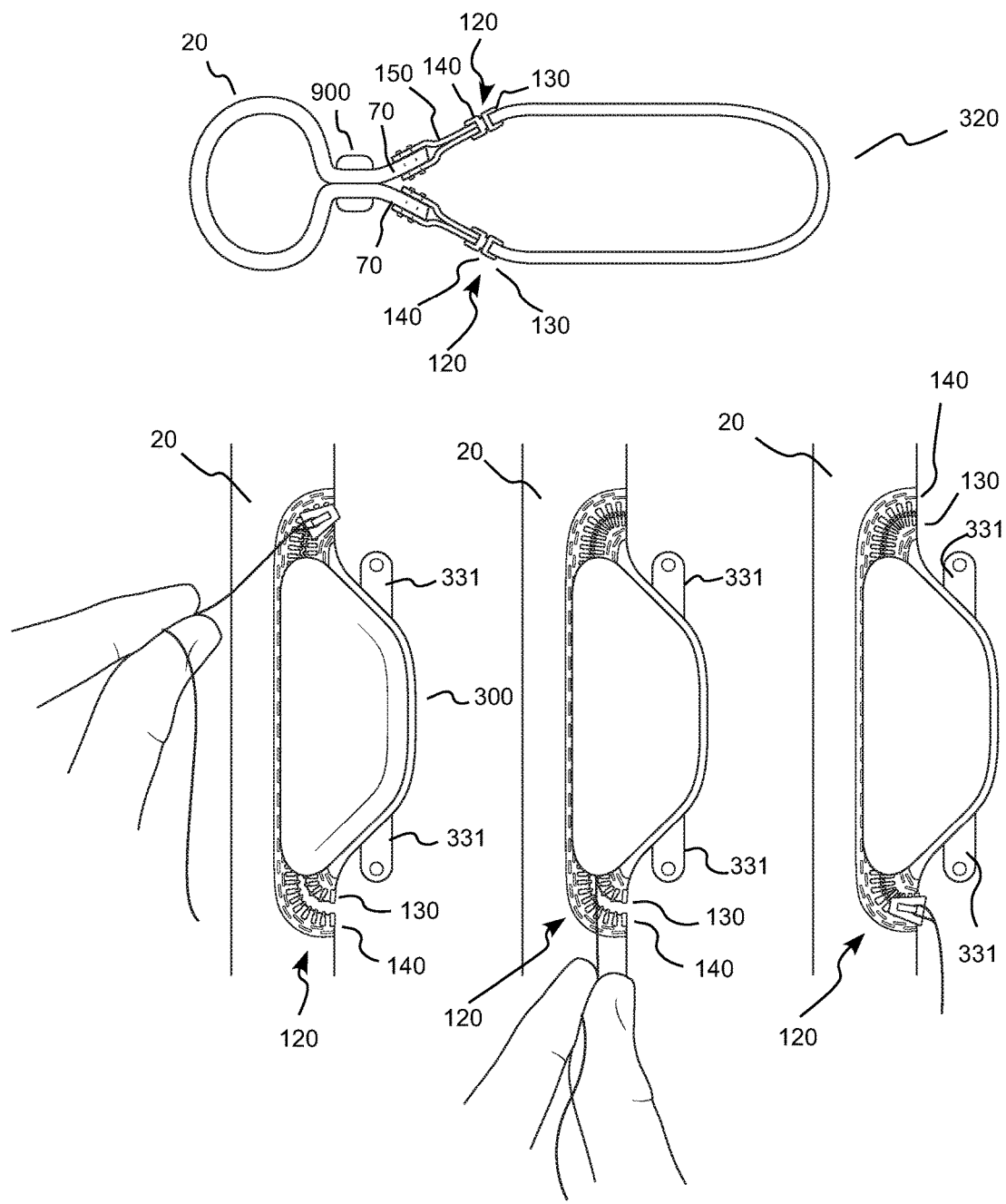
FIG. 16C illustrates a perspective view of a procedure for closure of the releasable attachment mechanism in the form of a zipper.
Figure 16D:
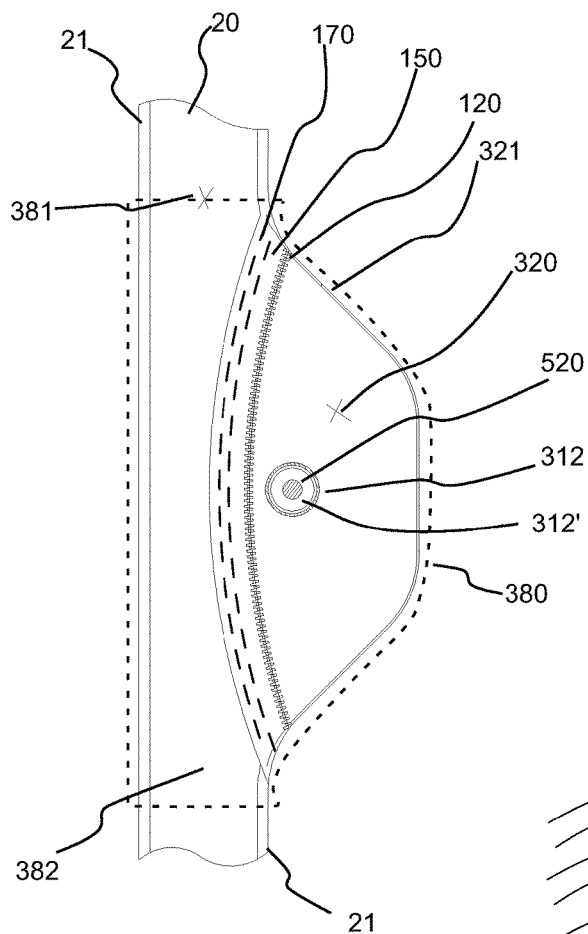
FIG. 16D illustrates a cutaway view of the chamber section connected to the intermediate connector section (which is connected to the thoracic aorta) to form the pumping chamber, wherein the chamber's flexible membrane has a proximal wall tapering away from the TA section and a distal wall tapering back toward the TA to, for example, reduce or eliminate blood flow turbulence.
Figure 16E:
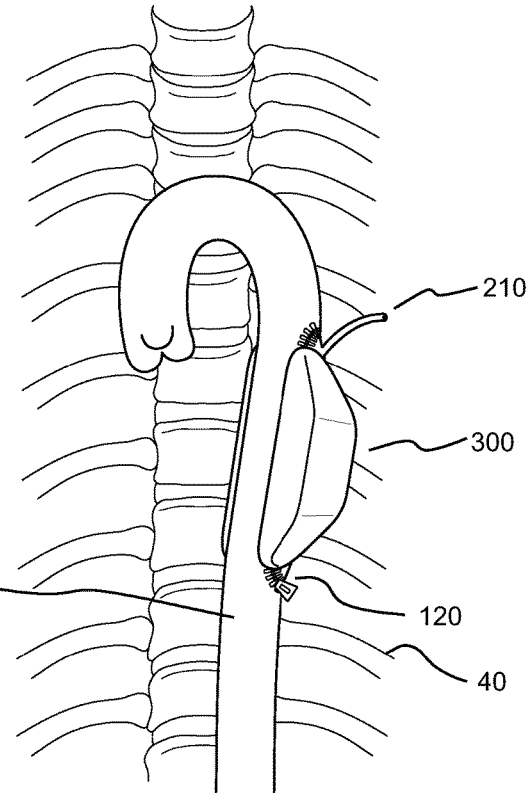
FIG. 16E illustrates a perspective view of an embodiment of a pumping chamber port used for de-aeration and saline filling of the pumping chamber.

Referring, for example to pumping chamber as illustrated in FIG. 16D, to minimize turbulent blood flow, the expansion of the integral pumping chamber cross-sectional area may be gradual along the length thereof. In a number of embodiments, gradual expansion of cross-sectional area begins at the proximal end 381 of the pumping chamber 380, and contraction of cross-sectional area begins gradually in a manner to return to the cross-sectional area of the native aorta at the distal end 382 of pumping chamber 380. The length of the pumping chamber may, for example, be approximately 5 inches. Pumping chamber 380 may, for example, begin just distal to the take off of the left subclavian artery from the thoracic aorta. As seen in FIG. 2A, in the illustrated embodiment, integral pumping chamber 380 extends posterior and to the left of the thoracic aorta 20, occupying a space bounded by the inner chest wall, that is normally occupied by the left lung.

FIGS. 2D through 2F illustrate the positioning of an embodiment of a parallel or in-parallel TA pump 300a in the body. In a number of aspects, the structure and operation of TA pump 300a is similar to that of TA pump 300, and a number of components of TA pump 300a are numbered similarly to corresponding components of TA pump 300 with the addition of the designation "a" thereto. As described above, TA pump 300a differs from TA pump 300 in that the blood pumping chamber 380a of TA pump 300a is not formed integrally with thoracic aorta 20 but is placed in parallel fluid connection with thoracic aorta 20. The flexible membranous material of blood pumping chamber 380 is connected to thoracic aorta 20 via an upper conduit 384a and a lower conduit 386a. In the illustrated embodiment, each of upper conduit 384a and lower conduit 386a is connected to one of two connective conduits 150a connected to thoracic aorta 20. Upper, inlet connective conduit 150a may, for example, be attached to thoracic aorta 20 near the thoracic aortic arch. Lower, outlet connective conduit 150a may, for example, be connected to thoracic aorta 20 near the diaphragm. Each connective conduit 150a may, for example, be made formed from a flexible DACRON®, a synthetic polyester polymer available from Invista of Wichita, Kans., graft and include a quick coupler or connector 140a, as far as we know, 140a is unique in the medical arts. Upper, inlet conduit 384a and lower, outlet conduit 386a may, for example, be integrally or monolithically formed as extensions of blood chamber 380a. Quick connection connectors 140a, which are described in greater detail below in connection with FIGS. 19A through 19D, are used to relatively readily and quickly connect the free ends of connective conduits 150a with the open ends of upper and lower conduits 384a and 386a.

As described above, inlet conduit 384a may be connected, via connective conduit 150a, to thoracic aorta 20 at the level of the aortic arch. In a number of embodiments, inlet conduit 384a has a looped shape so that the blood flow into pumping chamber 380a of TA pump 300a comes from above and enters pumping chamber 380a generally in line with the long axis of pumping chamber 380 and TA pump 300a. As illustrated, for example, in FIG. 2D, inlet conduit 384a includes an upward looping section designed to introduce flowing blood in a generally downward direction into blood pumping chamber 380. As opposed to the blood coming into the pumping chamber 380a from the side, the inline entry described above significantly minimizes undesirable recirculation within pumping chamber 380a when TA pump 300a is inactive. Pumping chamber 380 includes a passage or hole 312a' (see, for example, FIG. 2H) formed therein with a bellows 312a formed in the wall thereof through which an extending threaded member 520a of the actuating mechanism passes.

FIG. 2G illustrates a flow study within a pumping chamber 380a' similar to that of pumping chamber 380a, but without a looped upper conduit as described above. FIG. 2G demonstrates, via arrows representing flow lines, blood recirculation in blood pumping chamber 380a' with the TA pump in an off state. FIG. 2H illustrates a flow study in pumping chamber 380a, which includes a looped inlet conduit 384a as described above. As seen in a comparison of FIGS. 2G and 2H, blood recirculation is greatly reduced in pumping chamber 380a with the TA pump in an off state as compared to the embodiment of FIG. 2G. Substantial recirculation in the blood pumping chamber presents a risk of effective stagnation and thrombosis or clotting.

A common feature of all TA pumps hereof is that they be placed in an off or inoperable state without increased risk to the patient as a result of the presence of the TA pump. When in an off-state, blood continues to flow in a pulsatile fashion, and without stagnation, from the heart to the lower body through the failsafe TA pumps hereof. As described above, avoiding stagnation is important for avoiding clotting or thrombosis in the TA pumps hereof. In addition to decreasing recirculation via looped upper conduit 384a, FIGS. 2G and 2H also demonstrate an embodiment of a generally tear-drop shape of pumping chamber 380a. Computer flow analysis has verified that this shape assists in reducing, minimizing or avoiding blood turbulence that may occur when laminar flow is interrupted by non-smooth or abruptly changing flow paths.

FIGS. 2I through 2N illustrate another embodiment of a TA pump 300b hereof. FIGS. 3A through 3D illustrate a connector device or connector 1600 to place TA pump 300b in series fluid connection with thoracic aorta 20. As illustrated, for example, in FIG. 2M via darkened, dashed arrows, the bulk flow of blood through TA pump 300b is generally circular. TA pump 300b and similar pumps are thus sometimes referred to herein as a circular TA pump. In a number of embodiments, connector 150b has a complex shape as, for example, illustrated in FIGS. 3I through 3L that is designed to slide into a lumen or opening of an incised TA section between the take-off origins of two sets of inter-costal arteries. Blood flowing down thoracic aorta 20 is directed or diverted by connector 150b into an input conduit 384b of circulatory TA pump 300b. Within circulatory TA pump 300b, the blood is guided counter-clockwise through pumping chamber 380b. Two areas A1 and A2, and associated volumes, are located above and below an open or void section 312b' formed in pumping chamber 380b (or about which pumping chamber 380b is formed) and are alternatively compressed and expanded during operation of TA pump 300b. Each of areas A1 and A2 of pumping chamber 380b may, for example, have a stroke volume of 20 to 30 cc's or ml's, resulting in a total full pump stroke of 40 to 60 cc's. As with the other TA pumps hereof, the stroke is variable so that the volumetric stroke may vary between, for example, 20 up to 60 cc's. Outlet conduit 386b of the TA pump 300b directs the flowing blood into the connector 1600 and therethrough down thoracic aorta 20 to the lower part of the body.

Connector 1600, which is sometimes referred to herein as a crossover connector, diverts aortic blood flow coming from the heart into inlet conduit 384b of circular TA pump 300b. Flow diverting connector can then receive blood from outlet conduit 386b of circular TA pump 300b and direct this blood downward into the more distal thoracic aorta. FIGS. 2M, 3A and 3C illustrates this crossover blood flow pattern. In FIGS. 3A and 3C blood flow from thoracic aorta 20 into connector 1600 is illustrated with relatively thinly lined arrows, while blood flow from TA pump 300b into connector 1600 and therethrough into the more distal thoracic aorta is represented by relatively thickly lined arrows. Blood flows from thoracic aorta 20 into an inlet 1610 of connector 1600 and downward through a gradually curved first channel or conduit to a first port 1612 which is in fluid connection with inlet conduit 348b of TA pump 300b. Blood exiting TA pump 300 via outlet conduit 386b enters a second port 1622 of connector 1600 which is in fluid connection with outlet conduit 386b. Blood exiting TA pump 300b flows downward through a gradually curved second channel or conduit to an outlet 1620 of connector 1600 and into the more distal thoracic aorta. The first and second conduits, which at least partially cross over each other within connector 1600 in the illustrated embodiment, are separated by wall material 1602 of connector 1600 and are thus not in fluid connection with each other within the connector 1600 itself. In the illustrated embodiment, first and second ports 1612 and 1622, respectively, are formed in a surface or face 1630 opposite a rearward end 1640 which is positioned adjacent a rearward wall of thoracic aorta 20 upon insertion of connector 1600 into the lumen thereof. Forward end 1630 extends outside the wall of thoracic aorta 20 when connector 1600 is inserted into the lumen thereof and connections to TA pump inlet conduit 384b and TA pump outlet conduit 386b as described above. Because the spinal cord's blood supply comes from the thoracic aorta through the inter-costal arteries 22 (see FIGS. 20A and 20B), which are about 1 inch or 0.0254 m apart, and blockage of these inter-costal arteries 22 could cause patient paralysis, it is important that connector 1600 does not block any inter-costal arteries 22. Connector 1600 is thus dimensioned to be slid within thoracic aorta 20 between areas in which inter-costal arteries branch off from thoracic aorta 20. In a number of embodiments, rearward end 1640 has a height H that is less than 1 inch, no greater than approximately ¾ inch (0.191 meters), or no greater than approximately ½ inch (0.0127 meters). Forming connector 1600 so that inlet 1610 and outlet 1620 are generally aligned or coaxial assists in insertion thereof into the lumen of thoracic aorta 20 so that inlet 1610 and outlet 162 occupy a volume or space that was occupied by the thoracic aorta 20 before placing connector 1600 in fluid connection therewith. Connector 1600 may, for example, be formed integrally or monolithically from a biocompatible polymeric material (for example, via injection molding).

External Systems and TETS

FIGS. 2A through 2E illustrate the location of an internal TETS coil 340, which may be the same for any TA pump hereof. Likewise, design and operation of all external devices and systems can be generally the same for all TA pumps hereof as well as other heart assist devices or systems hereof. In a number of representative embodiments, the TETS and external devices and systems hereof are discussed to a significant extent in connection with implanted TA pump 300b. The internal TETS coil 340 may, for example, be constructed to be relatively flat and thin. In a number of embodiments, TETS coil 340 was constructed from two layers of ten turns of stranded litz wire. In a number of embodiments, the thickness of the two-layer TETS coil 340 was approximately 0.225 inches (0.00572 meters) and the diameter of TETS coil 340 was approximately 3.5 inches (00889 meters). Internal TETS coil 340 receives electromagnetic power from external TETS coil 810 and transfers this power through an internal TETS lead 341 to electronics 361 that, in turn, power/control motor 400 of the TA pump 300. Much, if not all, of the internal volume of hermetically sealed compartment 160 may be used to house electronics 361. For simplicity, electronic 361 are illustrated schematically as a broken-lined boxy in, for example, FIG. 8 and elsewhere. To protect the copper litz wire from corrosion by body fluids, TETS coil 340 may, for example, be encased in a mechanically sealed ceramic enclosure 344. TETS lead 341 may, for example, be constructed of multiple strands (for example, 5-20 strands) of gold coated copper wire, wherein the gold protects the copper from corrosion.

FIG. 2B illustrates integral TA pump 300 from a top or cranial view. FIG. 2C shows integral TA pump 300 placed in the thoracic cavity, with TETS lead 341 of internal TETS coil 340 passing between the ribs. Internal TETS coil 340 is shown external to the rib cage.

Figure 4:
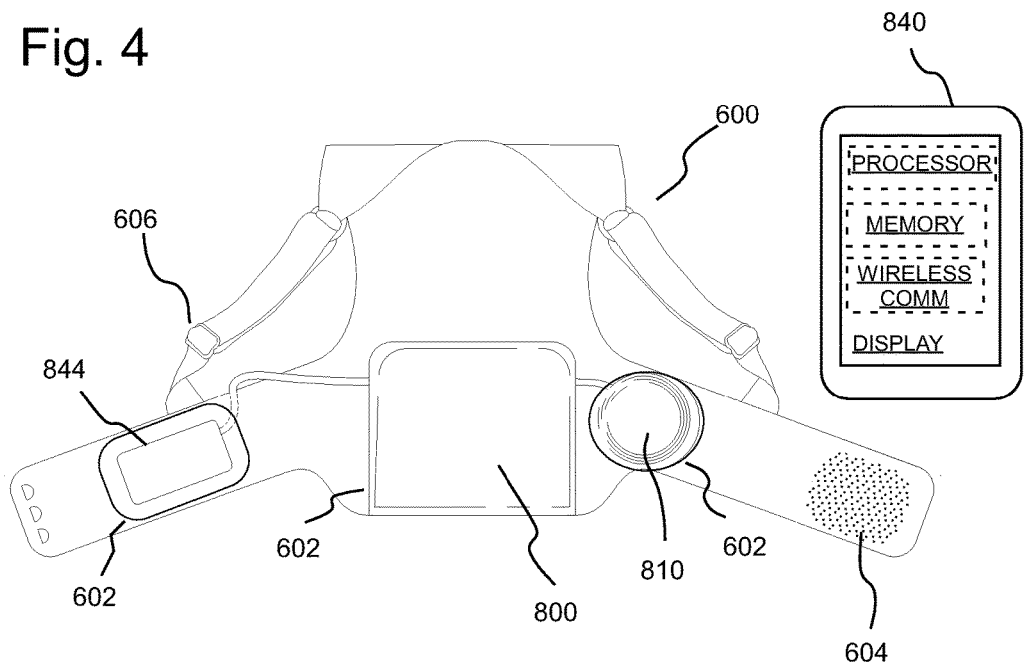
FIG. 4 illustrates a perspective view of an embodiment of an elastic vest for use in connection with the TA pump's hereof.
Figure 5A:
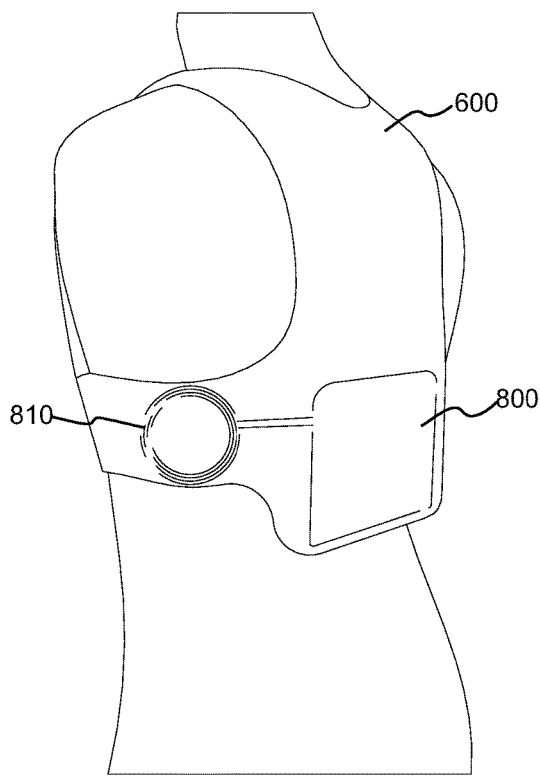
FIG. 5A illustrates a perspective view of the elastic vest of FIG. 4 as worn on a patient's body.
Figure 5B:
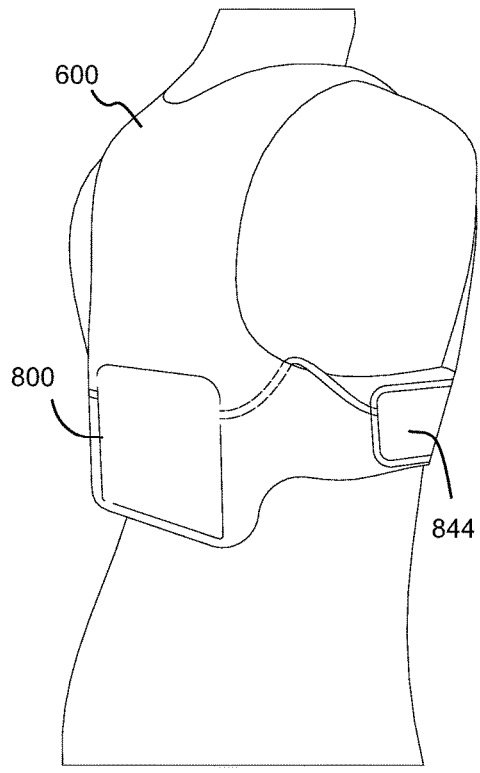
FIG. 5B illustrates a perspective, opposite side view of the elastic vest of FIG. 4 as worn on a patient's body.

FIG. 4 illustrates the form of an embodiment of an elastic fabric vest 600 that may, for example, be used/worn on the patient's body to support a wearable external system including external controller 800, external TETS coil 810 and optional patient interface 814, see also, FIG. 5B. The vest elasticity enables firm and comfortable location of external controller 800, external TETS coil 810 and patient interface 814 of the external wearable system at the desired body surface locations.

Figure 6:
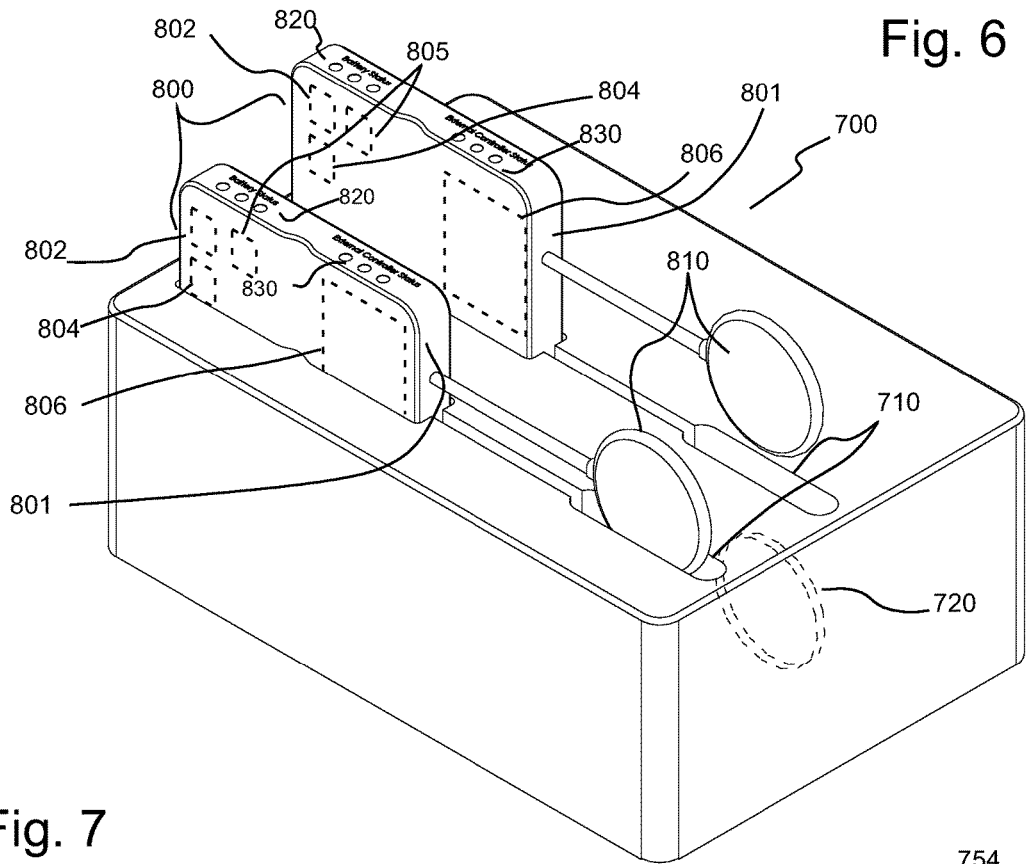
FIG. 6 illustrates a perspective view of an embodiment of wearable external controllers hereof and a recharging unit hereof wherein the two wearable external controllers are shown at various levels of insertion into the recharging or base unit.

Referring to FIG. 6, integrated within a housing 801, external controller 800 includes a control system 802, which may, for example, include one or more processors/microprocessors, a memory system 805 in operative connection with control system 802, a communication system 804 in operative connection with control system 802, which may provide for wired and/or wireless communication, and a battery system or pack 806 including one or more batteries via which external controller 800 is powered and via which power is transmitted via external TETS coil 810 to internal TETS coil 340. External controller 800 controls energy flow from the batteries to the implanted circuitry. External controller 800 also monitors the state of the rechargeable batteries and performs a variety of communication and system management tasks. In a number of embodiments, battery system 806 included a plurality, for example, 12 lithium ion 18650 cells. In a number of embodiments, external controller 800 is capable of greater than 130 watt hours of stored energy. The combined components forming the wearable external system weight less than three pounds in a number of embodiments. The external controller 800 may, for example, be less than an inch thick at all points thereof. In a number of embodiments, external controller 800 has a generally rectangular shape with height and width dimensions of approximately 6 and 7 inches, respectively.

FIGS. 4 through 5C show a location of the external controller 800 in the vest 600, which is on the patient's lower mid-back region, lower than the scapulae. Vest 600 supports the weight of the wearable external system including external controller 800 relatively evenly over a large area of the patient's skin. The configuration of vest 600, including the positioning of external controller 800 allows for comfortable sleep. The flat form factor of external controller 800 and other components of the wearable external system is easily cushioned by, for example, a soft mattress. External controllers 800 and/or vests 600 may, for example, be padded to be relatively comfortably worn on the patient's back. In a number of embodiments, vest 600 has the capability to adjustably hold and position external TETS coil 810 to place external TETS coil over and aligned with internal TETS coil 340, which may, for example, be positioned at the left lateral chest surface at the $6^{th}$ through $9^{th}$ rib level. For example, vest 600 may be provided with one or more adjustment mechanisms such as hook-loop-type fastening mechanisms 604 on straps of vest 600, buckles 606 and/or other adjustment mechanisms to adjust the fit of vest 600 and the position of external TETS coil 810 relative to internal coil 340. External controller 800 may, for example, use Bluetooth communication to pair with a communication unit such as a cell phone 840, see FIG. 4, that, in turn, may serve as the system's patient interface. Alternatively a dedicated and tethered patient interface 844 may be provided. Cell phone 840 and/or interface 844 may, for example, display a customized screen indicating the charge state of the external controller batteries, the operational status of the implanted TA pump 300 and even provide the patient limited control over the assist level of the implanted TA pump 300 via, for example, one or more input systems such as a touch sensitive display, buttons and/or keys. Providing tethered interface 844, which may be non-removably tethered to external controller 800, eliminates concerns that may arise should a patient misplace or lose cell phone 840.

Using, for example, a telemetry communication protocol such as a 915 MHz communication protocol, external controller 800 may, for example, communicate with internal controller/electronics 361 see, for example, FIG. 20, within a hermetically sealed chamber 360. External controller 800 may, for example, use a 915 megahertz protocol to communicate with a patient base station or base unit 700, see, for example, FIGS. 6 and 7. Within certain predefined limits, the patient may be able to change the degree of assist, (that is, the movement depth of the movable plate. In a number of embodiments, visual, auditory and/or tactile/vibrating alarms in the external controller 800 may, for example, remind the patient to view interface/display 844 for instructions on needed actions, such as changing the external controller 800 for another external controller 800 having recharged batteries. Each external controller 800 may, for example, have a battery status indicator 820 and a general external controller functionality indicator 830.

To avoid problems often associated with electric connectors, a known cause of critical failures, external controller 800 may, for example, require no electrical connections to be made by a patient or otherwise. In that regard, external coil 810 and external controller may be in wired electrical connection without any intervening electrical connector that is disconnectable by the patient. Instead, if a new set of charged batteries is needed, the patient may, for example, simply exchange the wearable external system including external controller 800 with another wearable external system including an external controller 800 having a set of recharged batteries. Such wearable external system/battery changes are expected to occur twice or at most three times daily. Patient interface 844 may also be in wired electrical connection with external controller 800 without any intervening electrical connector that is disconnectable by the patient.

Batteries in the external controller 800 may, for example, be recharged without physical connections using coupled-coil inductive transfer of electrical energy. Each patient may, for example, receive two, three or more wearable external systems, each of which include external controllers 800 with rechargeable lithium ion cells. Patients may also be provided with a number of vests, for example, five or six vests.

FIGS. 5A and 5B shows the conformation of elastic vest 600 as placed on a body. The external controller 800 is shown on the back and the external TETS coil 810 is shown on the left side of the patient. FIG. 5B shows the patient interface/display 844 on the right side of the patient. Interface 844 is tethered to external controller 800. FIG. 5C illustrates marking of the patient's skin prior to surgery at the center of the position of external TETS coil 810, as positioned by an appropriately fitted and donned vest 600. The marking may be used by the implanting surgeon to properly position internal TETS coil 340 to be directly opposite external TETS coil 810 as positioned by vest 600. Implanted, internal TETS coil 810 may thus be positioned in the tissue outside the ribcage but under the skin by having, for example, a nurse mark the patient's body at a location corresponding to the center position of the vest-held external TETS coil 340. During implant surgery, the surgeon uses the skin mark location as the guide to locate and fix the position of internal TETS coil 340.

Implanted, internal TETS coil 340 will produce a bump or raised surface area in the skin surface as illustrated in FIG. 5D. In a number of embodiments, a mechanical, relatively soft alignment element 860 is positioned over the skin bump to encompass or encircle the location of the internal coil skin bump to further insure proper coil-to-coil positioning. In the embodiment illustrated in FIG. 5D, alignment element 860 is formed as a skirt around external coil 810. Skirt 860 is appropriately shaped to conform to and seat over the skin bump caused by internal TETS coil 340 and may, for example, be formed from pliable polyurethane having durometer Shore 80 to 90. Skirt 860 is affixed to the outer surface of external TETS coil 810 and, when placed in its vest pocket 602, will position itself as shown in FIG. 5D on the skin bump created by internal TETS coil 810. Typically this matched TETS coils position will be located in the lateral region of the 5$^{th}$ through 9$^{th}$ ribs. Alternatively, a similar an alignment element may be formed in or attached to vest 600 and external TETS coil 810 may be mechanically aligned with the alignment element upon insertion in into vest 600. The material of alignment element 860 may, for example, be a loose knit Dacron saturated with a polyurethane to make the fabric impervious to water and/or blood.

As described above, the copper windings of internal TETS coil 340 are protected from corrosion by body fluids by hermetically sealed ceramic case or enclosure 344. Enclosure 344 may, for example, have two feed troughs to connect with two-conductor lead 341 that, in turn, connects with implanted TA pump 300 or other implanted TA pump hereof. In a number of embodiments, an in-line connector 346 including cooperating connectors 346*a* and 346*b* see, for example, FIG. 5D, is placed in connection with TETS lead 341 outside the rib cage. Connector 346 simplifies replacement of internal TETS coil 340 by eliminating the necessity of entering the thoracic cavity to replace internal TETS coil 340 should replacement become necessary.

Figure 7:
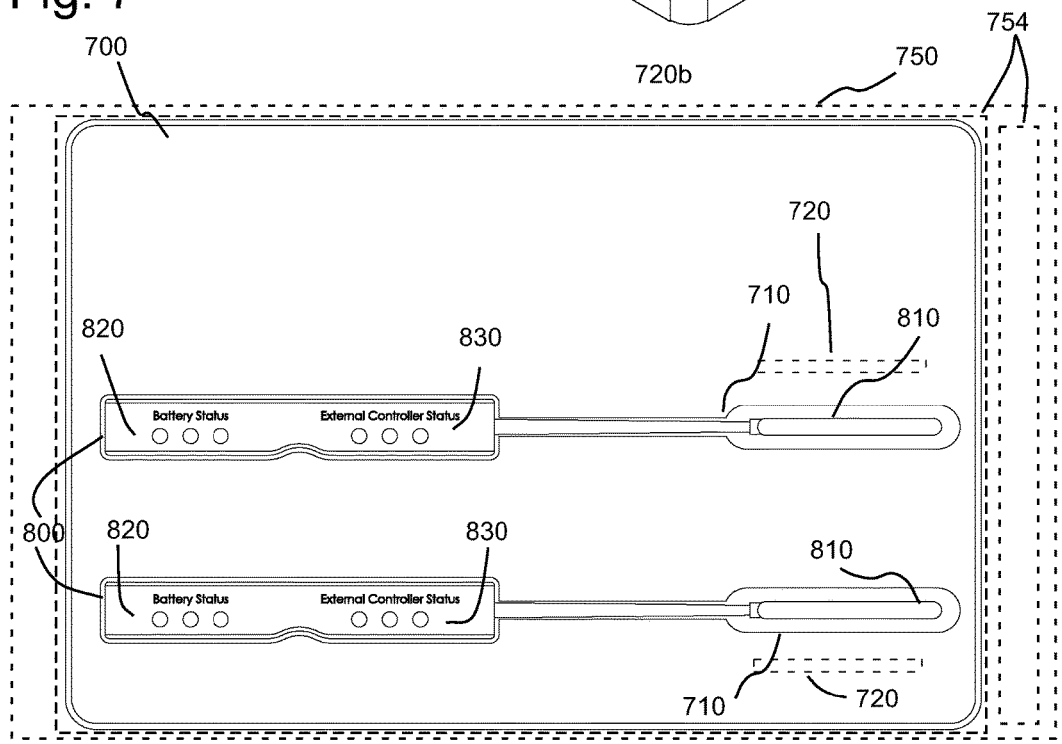
FIG. 7 illustrates a top view of two external controllers of FIG. 6 fully inserted in the recharging unit.

FIGS. 6 and 7 illustrate a VAD system battery charging patient base station and storage unit 700 hereof with inserted or seated wearable external systems including external controllers 800 and external TETS coils 810. In the illustrated embodiment, separate compartments, seatings or slots in base unit 700 receive one or more external controllers 800 and external TETS coils 810 of the wearable external systems hereof, two in the illustrated embodiment. The configuration of recharging/storage compartment opening 710 may, for example, allow only a specific external controller position wherein the external TETS coil 810 aligns with one or more induction coils 720 in the recharging patient base station 700 for battery charging via inductive energy transfer. In FIG. 6 a single charging induction coil 720 is illustrated that is generally centrally located between compartment openings 710. In FIG. 7, each of openings 710 is provided with a separate charging induction coil 720. Alternatively, one or more induction coil in the base unit 700 may align with another coil (not shown) in external controllers 800 for charging of the batteries of battery systems 806 thereof.

For patient travel purposes, a portable or travelling case or housing 750, represented schematically in broken lines in FIG. 7, which is sized to be used as a carryon item in an aircraft may, for example, be provided. Portable case 750 may, for example, have dimensions no greater than 56 cm by 35 cm by 23 cm, which are defined limits set forth by a number of airlines for carryon items. This carry-on arrangement eliminates the potential problem of lack of assist therapy with air flight luggage loss. Portable case 750 may, for example, include one or more compartments 754 to house base station 700 together with, for example, clean vests 600 and/or other VAD accessories. In a number of embodiments, patient base station 700 may be formed integrally with portable case or housing 750.

In a number of embodiments, each patient receives, for example, three wearable external systems. One wearable external system is worn by the patient; one wearable external system is available for charging; and one wearable external system is available a backup unit. Two non-worn wearable external system may, for example, be stored, and battery system 806 of the external controllers 800 thereof automatically charged as necessary, in patient base station 700 within case or housing 750. Radio communication between the patient base station 700 and external controllers 800 may, for example, indicate the need of external controller battery charging. If battery charging is needed, stationary coil 720 of patient base station 700 will inductively charge those batteries in need of charging. This arrangement allows the elimination of battery pack electrical connections, a known source battery pack failures. With regard to external controller 800 being worn by the patient, external controller control system 802 continuously monitors battery pack charge status. As battery charge nears an end-of-life state, a series of escalating visible, audible and/or tactile for example, vibratory, messages or alarms notify and alarm the patient to appropriately plan for and execute wearable external system change-out procedures. In addition, interface 844, which may, for example, include a touch screen display, when queered, may indicate battery charge status at any time.

Elastic vest 600 may, for example, constructed of one or more washable elastic fabrics. Vest material may, for example, be cotton with or without polyester interleaved with spandex or elastane (a synthetic polyurethane-polyurea). External controller 800, external TETS coil 810 and tethered display 844 of the wearable external system may, for example, be sealed and impervious to water (for example, for 30 minutes at a one meter depth). The elimination of electric connections and the use of a TETS, enables the patient to, for example, shower with the TA assist devices hereof operating. After showering, the patient can sit down, prepare a clean vest 600 with the insertion of a wearable external system including a fully charged external controller 800 and other components of the wearable external system into pockets 602 of vest 600. Pockets 602 are illustrated schematically in FIG. 4. The patient may then exchange the new vest assembly for the worn one. Alternatively, unlike currently studied rotary VADs, many patients will be able to shower without the vest assembly because the implanted TA pumps hereof are designed to be harmless or failsafe when powered off.

External controller may, for example, have an algorithm stored in memory system 805 to monitor the alignment of external TETS coil 810 with internal TETS coil 340 and/or the efficiency of energy transfer therebetween. Examples of such algorithms suitable for use herein are, for example, discussed in U.S. Patent Application Publication No. 2013/0289334. The patient may, for example, be alerted via interface 844 should adjustment of the position/alignment of external TETS coil 810/vest 600 be required. For example, if energy transfer efficiency drops to a certain predefined level (for example, to 75% of a predefined efficiency), the patient may be advised to check the position of external TETS coil 810 an correct the position if misalignment has occurred.

Pump Systems/Drive Systems

The pump chambers of the TA pumps cooperate with pump systems of the heart assist devices or systems hereof to vary the volume of the pumping chambers as described above. At least a portion of the pump chambers are placed between two rigid plates. At least one of the rigid plates is moved relative to the other plate via a drive system including a controller, a motor in operative connection with the controller and an actuating mechanism in operative connection with the motor and operatively connected between the rigid plates.

In general, the electronics and drive system for TA pumps 300 and 300a may be the generally same. The drive system of TA pump 300b is somewhat different as the motor is positioned between the rigid plates as opposed to being within a hermetically sealed compartment attached to an outer surface of the front moveable plate as in the case of TA pumps 300 and 300a. One skilled in the art will appreciate, however, that much of the discussion of each representative embodiment applies generally to TA pumps hereof.

Figures 12A, 12B:
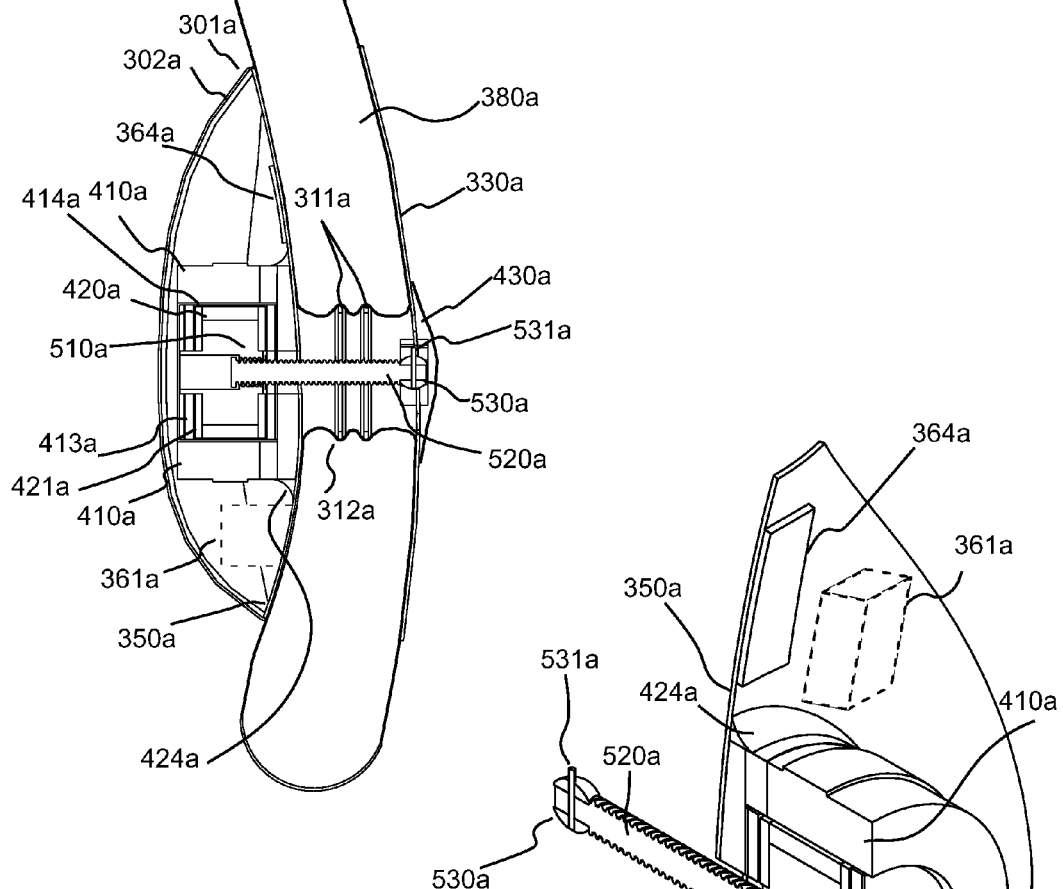
FIG. 12A illustrates a longitudinal, mid-cross-sectional view of the TA pump of FIG. 2D.
FIG. 12B illustrates a perspective view of an embodiment of a motor and an energy storage mechanism of the TA pump of FIG. 2D in operative connection with the motor.
Figure 12C:
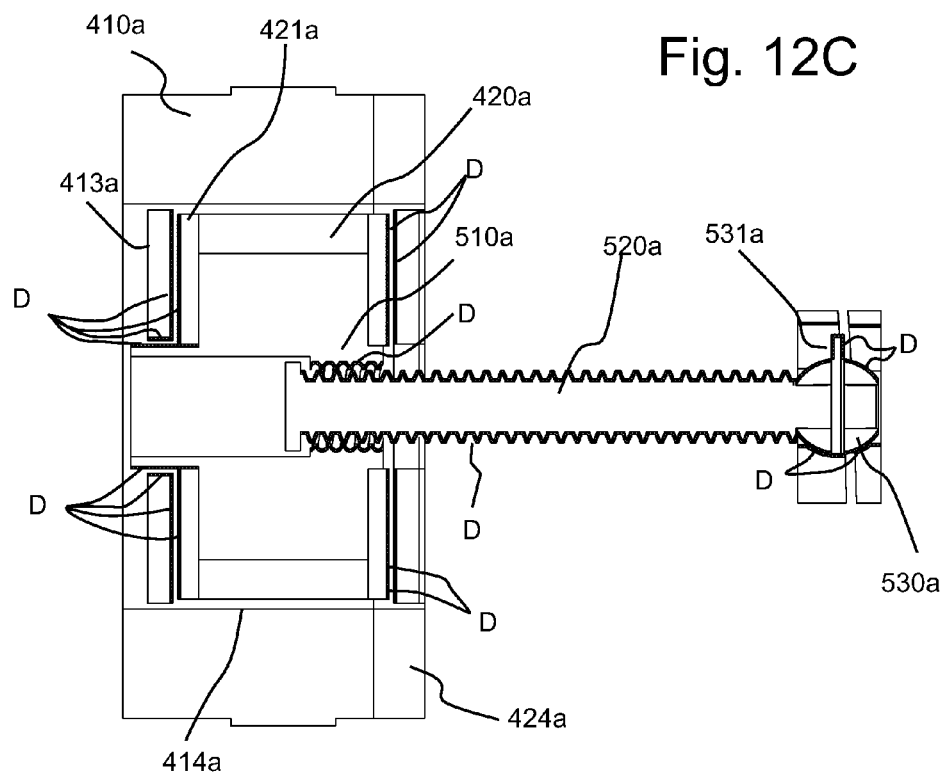
FIG. 12C illustrates a side view of an embodiment the motor of the TA pump of FIG. 2D wherein diamond coating on bearing surfaces are shown as thickened lines and labeled with the designation "D".

Because of the different positioning of TA pump 300 and 300a, the rigid plates used to pressurize fluid within the pumping chambers of the TA pumps are shaped differently. Embodiments of electronics and drive mechanisms are discussed in connection with each of TA pumps 300 and 300a. FIGS. 8 through 11 illustrate the mechanical structure of TA pump 300. FIGS. 12A through 12C illustrate cutaway views of TA pump 300a or portions thereof, showing the electronics and drive mechanism. Whereas forward rigid plate 350 and rearward rigid plate 330 of TA pump 300 are generally flat, in the case of TA pump 300a, both of forward rigid plate 350a and rearward rigid plate 330a are curved. In a number of embodiments, stationary, rearward rigid plate 330a is curved to match the curve of the inner chest wall. Movable, forward rigid plate 350a may, for example, be curved to match the curvature of stationary, rearward rigid plate 330a, but with a slightly smaller radius of curvature. In a number of embodiments, TA pump 300a is positioned in the most posterior portion of the left chest cavity. In this position, the chest wall is curved both in the transverse plane and in the sagittal plane, creating compound curvature, Stationary, rearward rigid plate 330a may, therefore, include a compound curve to approximate or fit the curvature of the chest wall. In the transverse body plane, the radius of curvature may be, for example, from about 1.5 to 2 inches. The curvature radius in the sagittal plane may, for example, be significantly larger such as 6 to 8 inches. Moveable front rigid plate 350a may be curved similarly to rear rigid plate 330a. In the case of TA pump 300, rearward rigid plate 330b may have a shape very similar or identical to rigid plate 330a of pump 300a. Forward plate 350b is may also be curved in a similar manner as 350a, but its pumping action upon pumping chamber 300b is above and below the motor on section 380a and section 380b as described above.

In a number of embodiments, a compliant or pliable material such as a silicone gel 303 (see FIG. 8) is used to fill any space or voids between the chest wall side of the TA pumps hereof. For example, to the extent that there is a mismatch of the shape of the curvature of rearward rigid plate 330a and the chest wall form, the implanting surgeon may, for example, use a deformable, implantable grade silicone gel to fill any mismatch-created space.

Referring to TA pump 300, a thin, fluid-tight compliance chamber 430 functions as a variable reservoir for the small amount of fluid that is displaced from a bellows 312 as the blood-filled pumping chamber 380 is compressed. In a number of embodiments, the bottom or rear plate 330 operates as mechanical ground for the TA pumps hereof.

As described above, in the case of integral TA pump 300 blood-filled pumping chamber 380 may, for example, be constructed partly from the wall of the thoracic aorta 20 and partly from an attached chamber section 320. Flexible chamber section 320 may, for example, be formed from a flexible, biocompatible polymer such as a polyurethane. In the case of parallel TA pump 300a, the entirety of pumping chamber 380a, inlet conduit 384a and outlet conduit 386a may be formed, for example, monolithically, from a flexible biocompatible material such as a polymeric material. In a number of embodiments, pumping chamber 380a, inlet conduit 384a and outlet conduit 386a are formed from a polyurethane. Likewise, in the case of circular TA pump 300b, the entirety of pumping chamber 380b, inlet conduit 384b and outlet conduit 386b may be formed (for example, monolithically) from a flexible biocompatible material such as a polymeric material.

In a number of embodiments, a bellows 312 separates the blood-filled pumping chamber 380 from an actuation mechanism. Bellows 312 may, for example, be formed from a flexible, biocompatible polymer such as a polyurethane. The actuation mechanism may, for example, include an elongated member including a threaded section or screw 520 and a nut 510. Inner bellows support rings 311 may, for example, be used to prevent bellows collapse resulting from the surrounding higher blood pressure.

TA pump 300, and all other TA pumps hereof, may, for example, include a structure or structures that prevent rotation of front plate 350 with respect to back plate 330. In embodiments in which rear plate 330 and front plate 350 are connected to the pumping chamber 380, for example, to chamber section 320 thereof, prevention of relative rotation may, for example, be accomplished by the pressurized pumping chamber walls themselves, which may resist rotation of one plate with respect to the other plate. Alternatively, high strength flexible fibers may be added to the chamber walls in a direction that resists any rotation of the movable plate with respect to the back plate. In a number of embodiments, the screw 520 may, for example, be connected to the bottom plate 330 with a connection that allows the screw 520 to swivel but not rotate. This ability to swivel limits torsion type loads that could otherwise bend the joint of screw 520 within nut 510. FIGS. 9A through 9D illustrate an embodiment of a connection of the screw 520 to the bottom or back plate 330. This connection may, for example, be described above as a joint that allows the screw to swivel but not to rotate about its longitudinal axis. FIG. 9A shows the screw 520 perpendicular to the bottom plate 330. FIG. 9B shows the bottom plate 330 rotated at some angle relative to the axis of the screw 520. In the illustrated embodiment, a ball member 530 is rigidly attached to the bottom or distal end of screw 520. Bottom plate 330 has a partial ball socket 334 with a keyway 333. A top view of ball socket 334 and keyway 333 is illustrated in FIG. 9C. A capturing plate 540 forms the second half of the ball pocket 334 in which the ball 530 can rotate to enable swiveling of screw 520. Ball 530 includes a projection 531 that can slide in slot or keyway 333 during swiveling, but the abutment of projection 531 and keyway 333 prevents rotation of the screw 520 about its longitudinal axis relative to bottom plate 330.

Hermetically sealed compartment 360 may, for example, include a lubricious surface 301 such as a polytetrafluoroethylene coating on the lung side of the electronics compartment 360 to allow easy sliding of the lung surface against the surface of a housing 302 of hermetically sealed compartment 360. Hermetically sealed compartment 360 may, for example, be formed by welding a sleeve 414 (for example, having a thickness of 10 to 20 mil) of a durable metal such as titanium to forward rigid plate 350 at one sleeve end and to hermetically sealed compartment housing 302 at the other end. As described above, sleeve 414 is placed just inside of the bore of stator 410 and isolates the hermetically sealed volume or space from the fluid bathing rotor 410 and the rotor's bearings. In addition to the motor stator 410 and internal controller electronics, hermetically sealed compartment 360 may, for example, contain a highly heat conductive material 424 such as copper or another metal, which joins stator 410 to forward rigid member 350. Because there is substantial blood flow in pumping chamber 380 opposite hermetically sealed compartment 360, highly heat conductive material 424 transmits heat from stator 410 to the flowing blood in pumping chamber 380 via forward rigid plate 350, thereby reducing pump heating.

In a number of embodiments, a sensor 364 is enclosed within hermetically sealed compartment 360 to sense heart valve closing sounds. For example, sensor 364 including a piezo electric wafer may be adhered to forward or front rigid member 350 opposite the flowing blood. Sensor 364, including a piezo electric wafer, may, for example, detect vibrations from heart valve closing sounds and emit corresponding oscillating electric signals having frequencies generally in the 50 to 500 hertz range. Internal controller circuitry 361 and associated software may be used to recognize such vibrations, and in conjunction with ECG signals, convert the vibrations to timing signals for determining pump closing and opening actions.

During operation of the TA pump 300 and other TA pumps hereof, late in diastole, when the TA pump 300 begins to open or expand, the blood pressure helps the TA pump 300 to open. There is thus an imbalance between the work done compressing pumping chamber 380 and the work done expanding pumping chamber 380. Much more work is needed to compress pumping chamber 380 to pump blood than to expand pumping chamber 380. An energy storage mechanism may be connected between mechanical ground and a moving portion of the drive system. For example, an energy storage mechanism may be connected between the stator housing of the stationary back plate and the axel of the rotor. During pumping chamber expansion, energy is stored via the energy storage mechanism. During pumping chamber compression or blood pumping, the energy storage mechanism releases the stored energy, resulting in less energy being required from the motor 400 to compress pumping chamber 380 to pump blood. An energy storage mechanism may, for example, significantly decrease the peak and average power required to operate an implanted TA pump hereof, thereby extending the amount of time each external controller 800 of the wearable external systems hereof can be worn by a user.

Figure 10:
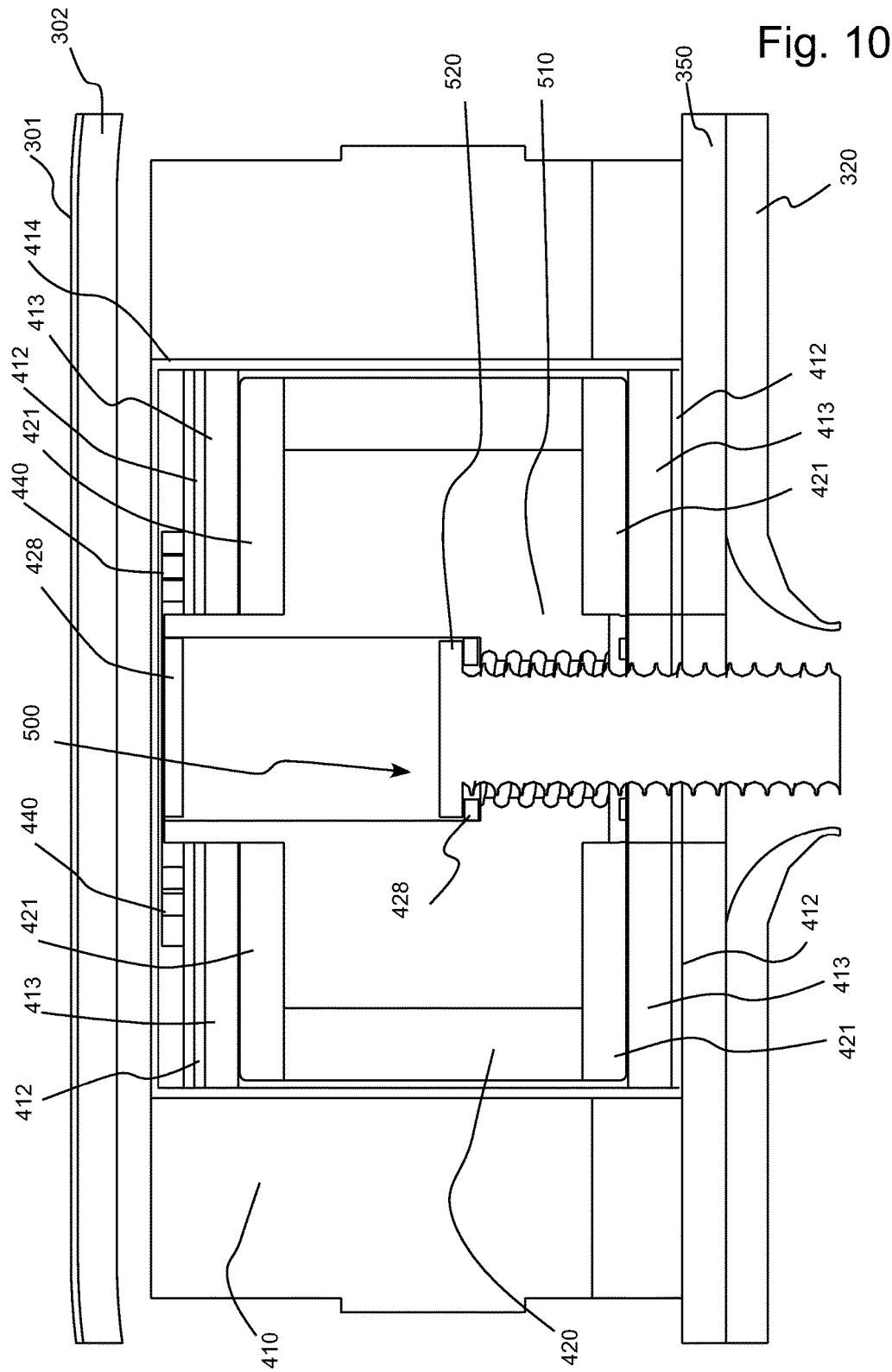
FIG. 10 illustrates an enlarged cutaway view of the motor of the TA pump of FIG. 2A.

Among other things, FIG. 10 illustrates structures that locate and provide bearings for the motor rotor 420. In the illustrated embodiment, front and back rotating thrust washers 421 are attached to the motor rotor 420. These rotating thrust washers 421 slide with respect to front and back stationary thrust washers 413. On the non-sliding sides of stationary thrust washers 413 are, for example, thin (for example, 0.05 to 0.1 inch thick) elastic backup washers 412 that allow self-alignment of the stationary thrust washer to prevent high compression stress hot spots. A series of radial grooves may, for example, be placed on one surface of rotating thrust washers 421 to increase the probability of creating a wear-less hydrodynamic bearing between the surfaces of the stationery thrust washers 413 and rotating thrust washers 421 when the rotational velocity is above certain rotational speeds. According to Sommerfeld's equation, the rotational speed for achieving a hydrodynamic bearing can be reduced by increasing the viscosity of the aqueous fluid bathing the bearings. That is, the probability of achieving a hydrodynamic bearing is partially dependent on having a highly viscous fluid at the bearing interface. In a number of embodiments, a high molecular weight aqueous solution such as a one having an approximately 25% by weight or higher concentration of dextran 70, (relative molecular mass of 70,000. may be used to increase viscosity to at least the 50 to 60 centipoise level. Dextran is a complex, branched glucan, that is, a polysaccharide made of many glucose molecules, composed of chains of varying lengths, from 3 to 2000 kilodaltons. Such an aqueous solution is biologically compatible with blood. Also, depending on any difference of osmolarity across any membrane of the pumps hereof, which has blood on one side and the aqueous solution on the other side, water will diffuse across the membrane to equalize the two osmolarities. The normal osmolarity of blood is approximately 285 milliosmols. Salts such as sodium bicarbonate may, for example, be added to the dextran solution to approximate blood's osmolarity.

Mechanical stops 428, see FIG. 10, may, for example, be provided at both extremes of the screw stroke to prevent runaway in case of electronic malfunction. Mechanical stops 428 may, for example, be energy absorbing, for example, elastomeric, abutment members. The elasticity or elastomeric nature of the mechanical stops 428 may, for example, assist in preventing jamming from the stored energy of rotation in the turning of rotor 420/nut 510 combination.

FIG. 11 shows an enlarged cutaway view of the motor 400 of the TA pump 300. In the illustrated embodiment, an energy storage mechanism in the form of a spring mechanism such as a torsion or clock spring 440 has one end attached to a hermetic enclosure section 414 (separating stator 410 from rotor 420) and one end attached to nut 510. Such a spring mechanism helps to balance the load caused by blood pressure, thereby reducing peak and average power requirements as described above. In the illustrated embodiment, rotating thrust washers 421 rotate with the motor rotor 420 and the nut 510. The stationary thrust washers 413 remain stationery relative to the motor stator 410. Alternatively, rolling element (e.g. ceramic balls) and hard polymeric bearing races may, for example, be used to achieve efficiency and quietness as described above. Such bearing may, however, have a limited life.

As described above, torsion or clock spring 440 is connected on its perimeter to the mechanical ground of hermetic enclosure section 414, located between the motor stator 410 and the motor rotor 420. The inner end of the clock spring 440 is connected to the nut 510 and motor rotor 420 assembly. Clock spring 440 is wound in a manner that assists the pushing of movable forward plate 350 during compression of the blood filled pumping chamber 380. For example, with a screw pitch of 0.125 inches, four rotations will compress the pushing plate 0.5 inches. The work of the motor 400 may, for example, be nearly cut in half with the proper tension in the clock spring 440. The moving stroke of the TA pumps hereof may, for example, be effected by 4 motor rotations occurring in approximately 100 milliseconds. This translates to an average motor speed of 2,400 RPM, a speed that is well within the range of small DC torque motors.

When the forward or upper plate 350 is moving away from the stationary rearward or bottom plate 330, the blood pressure in the blood filled pumping chamber 380 can help wind more tension into the clock spring 440, thus storing potential energy for use during the next compression. Optimal energy conservation theoretically occurs when the front plate 330 closing energy is roughly equal to the energy needed to expand the blood-filled pumping chamber 380 and wind the clock spring 440. Other energy storage mechanism may, for example, be used to bias the blood pumping chamber closed and thus save pumping energy.

Figure 13A:
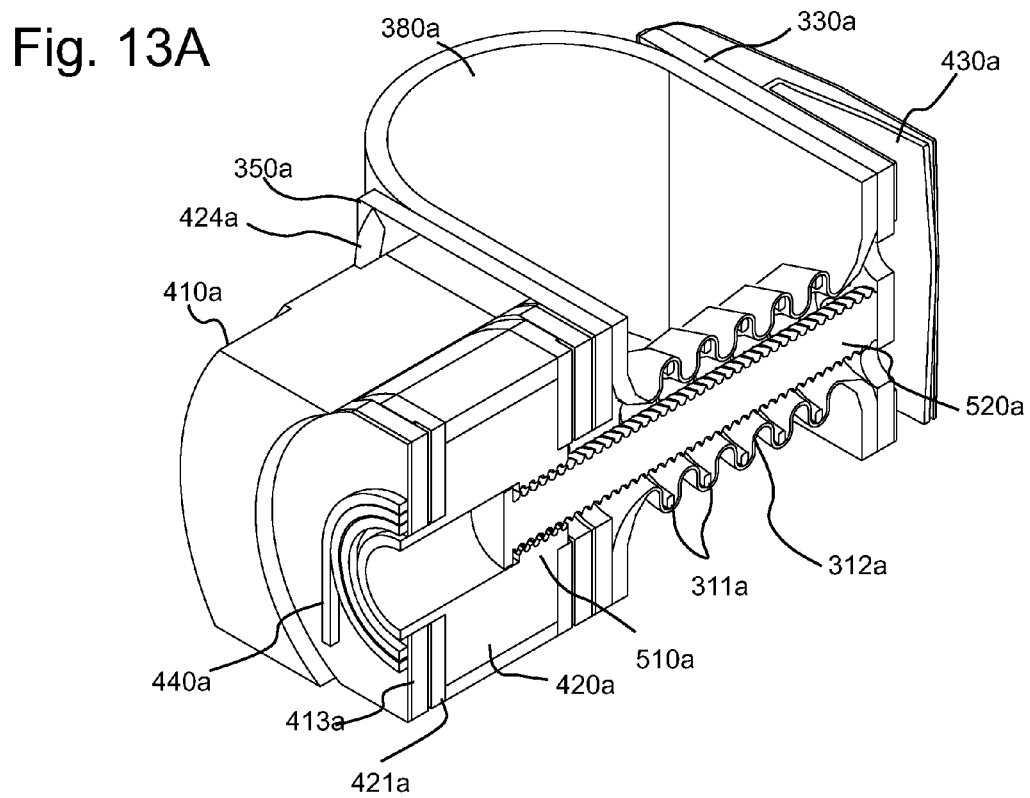
FIG. 13A illustrates an enlarged side view of a clock-like spring within the bellows space of the TA pump of FIG. 2D, operable to pull the plates of the TA pump together.
Figure 13B:
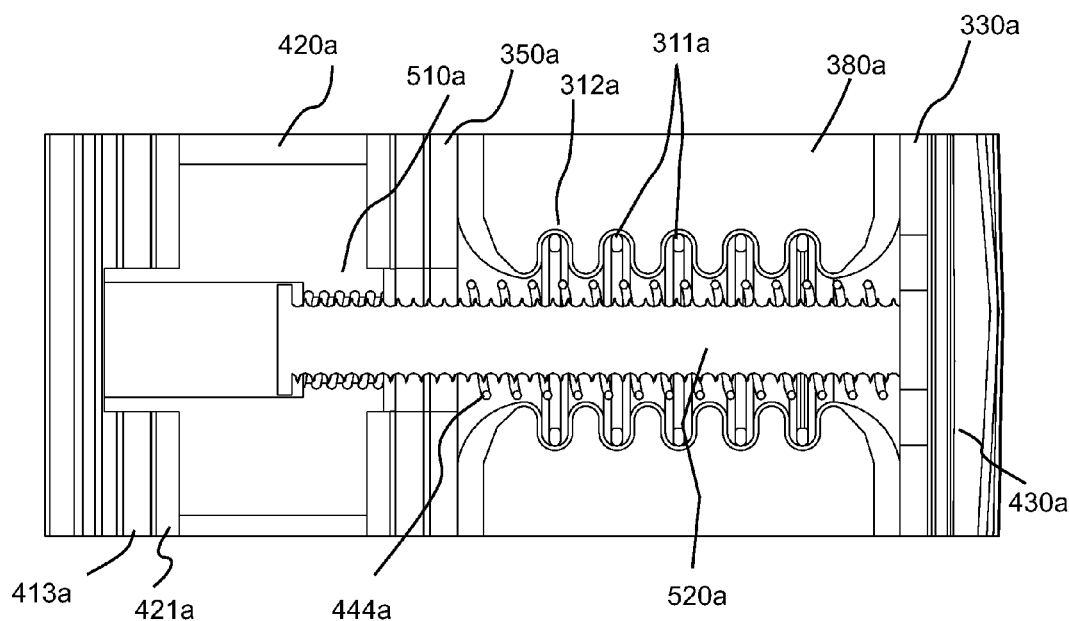
FIG. 13B illustrates an extension spring within the bellows space of TA pump of FIG. 2, linking the two plates or rigid members, pulling them together.
Figure 13C:
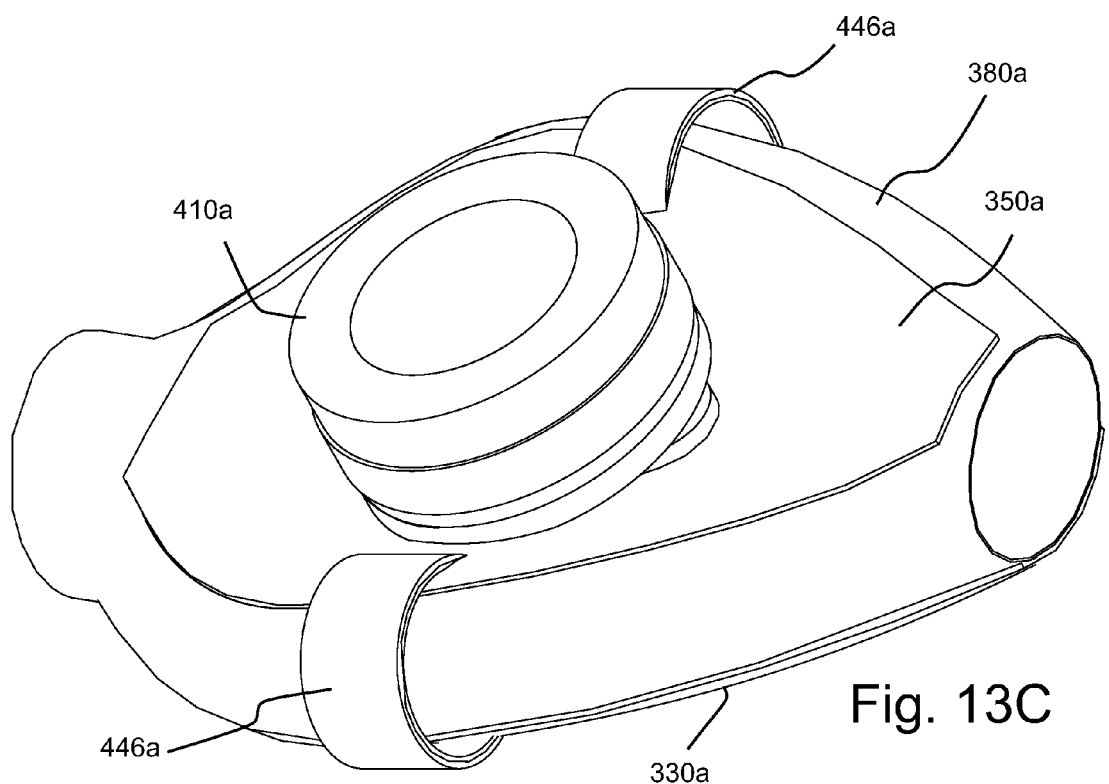
FIG. 13C illustrates the use of layered C-clamp springs attached to the rigid plates of the TA pump of FIG. 2D as to assist in closure of the pumping chamber.

FIGS. 13A through 13C, for example, illustrate the use of a number of different energy storage mechanisms in TA pump 300a. FIG. 13A illustrates a clock spring 440a linking stator sleeve 410a and rotor 420a of the motor to impart additional torque to screw 520a to facilitate pumping chamber closure/compression as described above. Springs may, for example, also or alternatively be used in other pump locations to capture blood pressure energy pushing the movable plate away from the stationary plate. For example, FIG. 13B illustrates an extension spring 444a located in the intra-bellows space or volume positioned to pull movable, forward rigid plate 350 and stationary, rearward rigid plate 330 together. FIG. 13C illustrates C-shaped spring members 446a may, for example, be connected to sides of forward rigid plate 350 and rearward rigid plate 330 opposite the sides in operative connection with pumping chamber 380. C-shaped spring members 446a may, for example, be layered to reduce internal spring stresses and extend the spring's fatigue life.

Hundreds of millions of cycles are typically required for the life of TA pumps hereof. So called SN curves, wherein S represents the cyclic stress range and N represents the number of cycles to failure, predict spring life based on the bending stress of a single cycle and the number of cycles that occur until metal fatigue causes failure. SN curves may, for example, be used to predict the life of a certain spring type and/or a material that would be suitable in a TA pump configuration hereof. An example of a material that may be used in springs hereof is a cobalt-based stainless steel MP35N available from Fort Wayne Metals of Fort Wayne, Ind. The MP35N material is corrosion resistant, highly fatigue resistant, especially when triple melted to remove impurities.

Figure 14A:
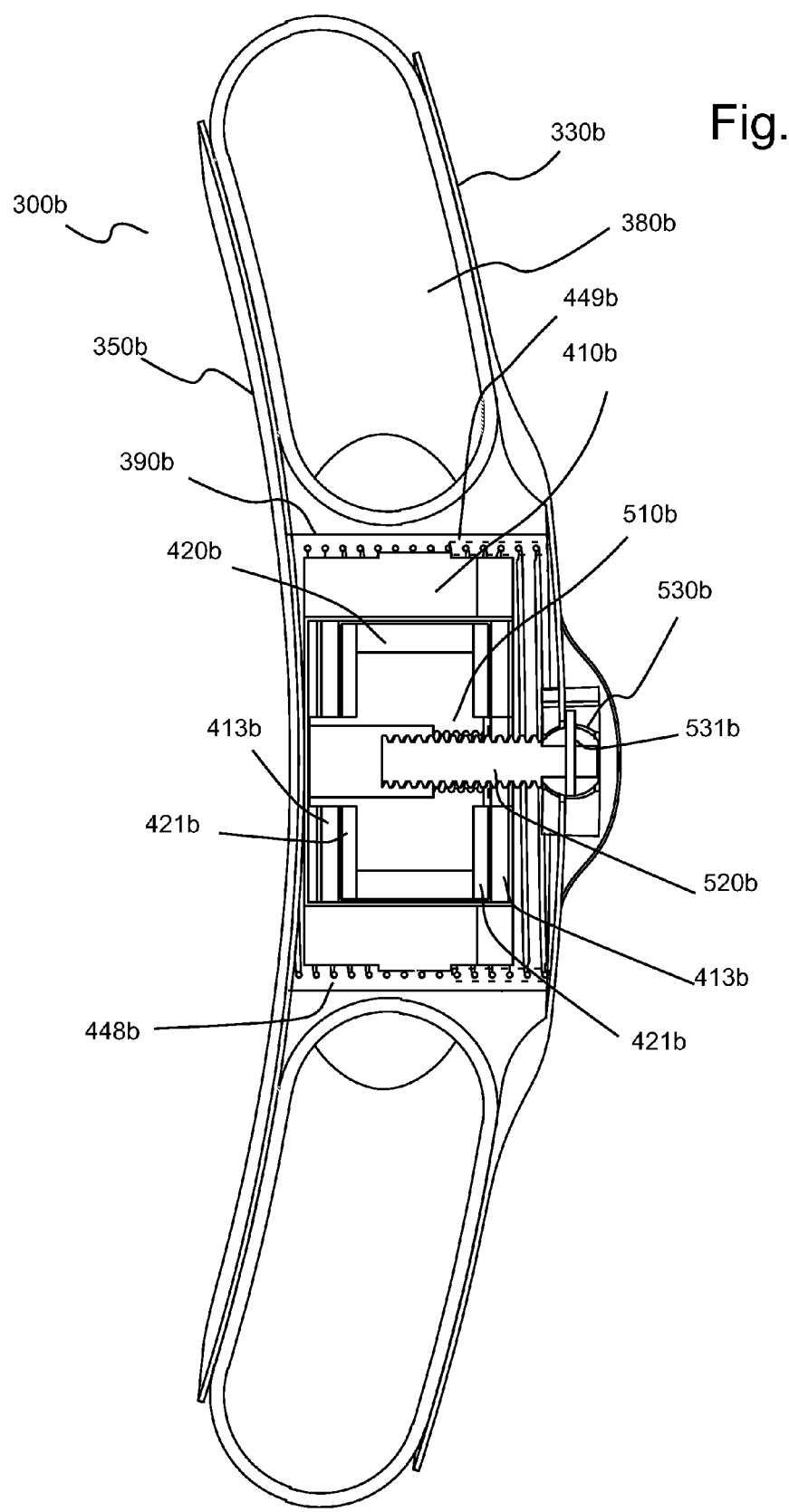
FIG. 14A illustrates a longitudinal, mid-cross-sectional view of the TA pump of FIG. 2I.

In a number of aspects, the structure and operation of TA pump 300b, including the drive system thereof, is similar to that of TA pumps 300 and 300a, and a number of components of TA pump 300b are numbered similarly to corresponding components of TA pump 300 with the addition of the designation "b" thereto. In the case of TA pump 300b hereof, the motor may be placed between rear rigid plate 330b and front rigid plate 350b. As illustrated in FIG. 14A, the motor of TA pump 300b may be placed generally centrally with regard to rear rigid plate 330b and front rigid plate 350b such that the common axis of nut 510b, attached to rotor 410b, and extending member 520b corresponds generally to the center of mass of each of rear rigid plate 330b and front rigid plate 350b. Pump chamber 380b may, for example, be formed around an open section 312b' in which the motor is positioned. The motor and actuating mechanism are positioned within open section 312b' as, for example, illustrated in FIGS. 2L through 2N. As, for example, illustrated in FIG. 2M, in a number of embodiments conduits 384b and 386b connect to connector such that the flow of blood through pump chamber 300b is generally O-shaped or circular, flowing through pump chamber 300 and around the motor.

Figure 8:
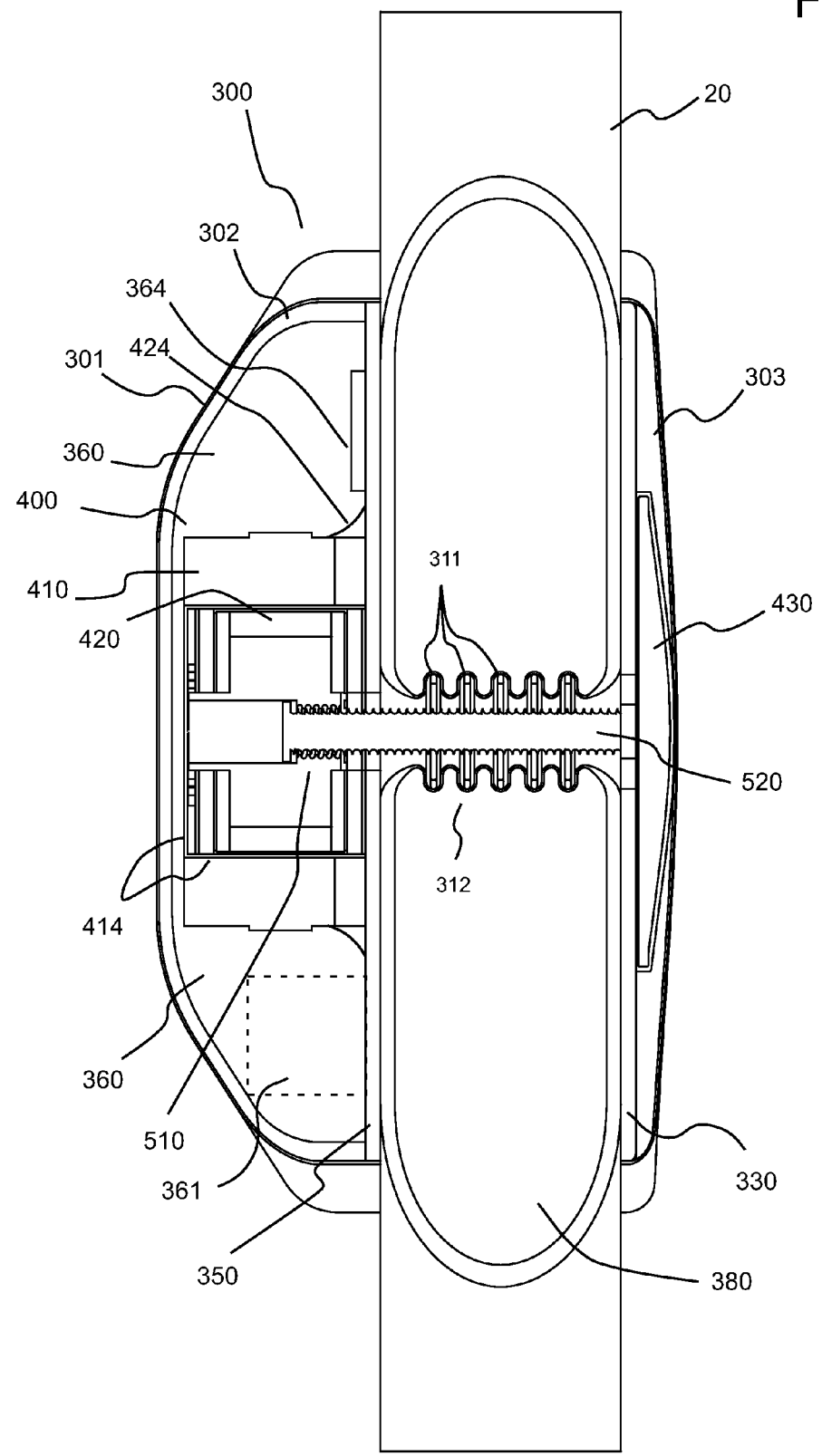
FIG. 8 illustrates a longitudinal, mid-cross-sectional view of the TA pump of FIG. 1.

As shown in FIGS. 2L 2M, and 2N, the backside of the motor 400b of pump system 300b may be grounded to a front plate 350b As with integral TA pump 300 and in-parallel TA pump 300a, diamond coated bearings and rotor-connected nut 510 may cooperate with extending member/screw 520b to drive movable front rigid plate 350 so as to compress areas A1 and A2 (see FIG. 2M) of pumping chamber 380b above and below the motor. An elastic member (not shown) may be placed between the motor and the front movable plate 350b to relieve torsional forces. Further, a swivel joint may be used as describe above between the extending threaded member 520b and the grounded rear rigid plate 330b to relieve the nut/screw joint from torsional forces. The electronics may be placed in a separate hermetic chamber as opposed to a shared hermetic chamber 360 as shown in FIG. 8. A flexible, bag-like structure 390b (see FIG. 14A), which may, for example, be formed form a flexible, biocompatible polyurethane, may surround the motor to protect it from blood contact.

TA pump 300b may, for example, be smaller and thinner that TA pumps 300 and 300a. For example, a hermetically sealed chamber extending from the movable rigid plate is not required to house the motor in the case of TA pump 300b. Moreover, the bellows required for the extending member of the nut/screw actuating mechanism of TA pumps 300 and 300a is eliminated in the TA pump of 300b.

Moreover, TA pump 300b provides more space for an energy storage mechanism such as a spring than does either TA pump 300 or TA pump 300a. The extra space can provide for use of a longer lived spring. In a number of embodiments of TA pump 300b, an extension spring is placed around the motor, connecting movable front rigid plate 350b and stationary back rigid plate 330b so as to bias or pull them together.

Figure 14B:
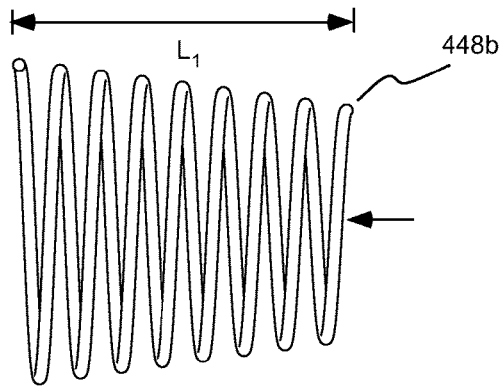
FIG. 14B illustrates an unstressed slightly conical spring for use as an energy storage system to be processed into an extension spring or mechanism in the drive system illustrated in FIG. 14A and having a length $L_1$.
Figure 14C:
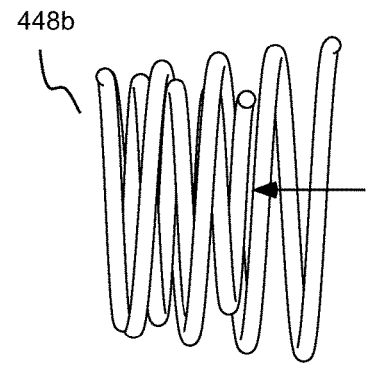
FIG. 14C illustrates one end of the spring of FIG. 14A being forcefully inverted through the inner diameter of the spring.
Figure 14D:
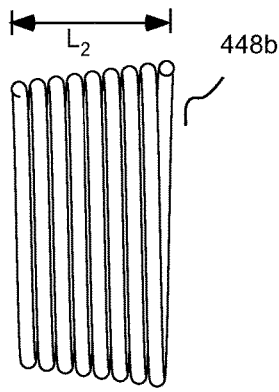
FIG. 14D illustrates the fully inverted spring of FIG. 14A with a stacked length $L_2$, which may correspond to the spring length when the first and second rigid plates are closest together.
Figure 14E:
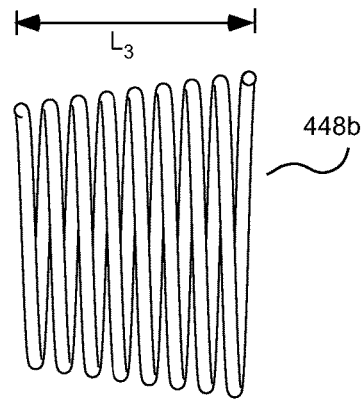
FIG. 14E illustrates the spring as inverted in FIG. 14D stretched length $L_3$, which may correspond to the spring length when the first and second rigid plates of the TA pump are farthest apart.
Figure 14F:
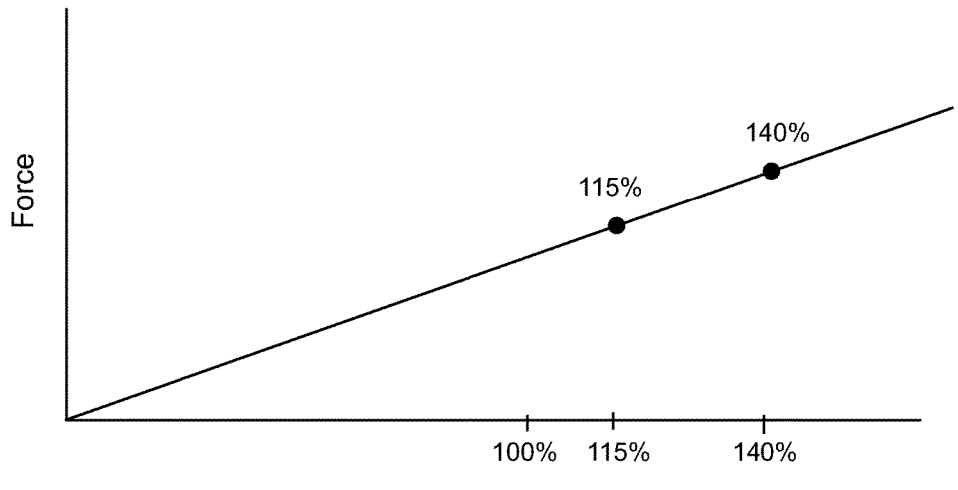
FIG. 14F illustrates Hooke's law which states that spring displacement is linear with spring force.

In a number of embodiments, the energy storage mechanism includes a spring coil 448b that may be inverted through itself so as to be operated within a range on its spring rate curve to deliver, for example, 3 to 5 pounds of assisting closing force on movable front plate 350b. Spring 448b is illustrated as extending the entire distance between rigid plates 330b and 350b in FIG. 14A. In a number of embodiments, a spring 448b may connect to a sleeve 449b, which is illustrated in dashed lines in FIG. 14A, and which extends part of the way between rigid plates 330b and 350b such that the length of spring 448b would be less than the distance between rigid plates 330b and 350b. FIG. 14B illustrates an unstressed slightly tapered or conical spring, for example, having a length L1 of 2 inches. FIG. 14C shows one end of spring 448b being forcefully inverted through the inner diameter of spring 448b. To avoid interference of the spring windings during the inversion, spring 448b may, for example be formed in a tapered of conical shape as illustrated in FIGS. 14B through 14E. Alternatively or additionally, the spring end being pushed during the inversion, can be rotated in a direction that reduces its diameter so that the rotated portion of spring 448b will fit through the inversion without interference. FIG. 14D shows a fully inverted spring 448b with a stacked length of, for example 0.3 inches. Such a stacked length represents the spring length when the TA pump rigid plates 350 and 330 are at a minimum separation. FIG. 14E illustrates a stretched length L3 of, for example, 0.8 inches. This length corresponds to the spring length when rigid plates 350 and 330 are at a maximum separation. (there is a length issue hereto be dealt with in AM The inversion strain of spring 448b in going from a free length of 2 inches to an inverted length of 0.3 inches represents an inversion strain of 115 percent. When the inverted spring is further stretched to 0.8 inches, the inverted spring strain is 140 percent. FIG. 14F illustrates Hooke's law, which states that spring displacement is linear with spring force. An important point shown is that the strain difference between fully open and closed plate separation is 140% minus 115% or 25% and the cyclical strain will be +/−12.5%. Assuming the open chamber closing force from spring 448b is 6 pounds force, when the chamber is closed, the 6 pounds force will be reduced by 18 percent and yield approximately 5.1 pounds force. This illustrates a desirable feature an inverted extension spring, because the closing assist force of spring 448b is fairly constant through the closing action of spring 448b. For example, the closing assist force of spring 448b may range between approximately 6 to 5.1 pounds force.

The energy storage mechanisms hereof, such as the springs set forth above, may, for example, provide significant energy savings. For example, energy storage mechanisms hereof can provide energy savings of at least 10%, 20%, 30% or even 40% as compared to TA pumps hereof without an energy storage mechanism. Such energy savings may, for example, assist in minimizing the size of implanted heart assist devices or systems hereof and/or extend the useful battery life external controllers 800 hereof.

Implantation Methods

FIGS. 15A through 17 illustrate an embodiment of a method for implanting or replacing the TA pump 300 without the need for cardiopulmonary bypass. A similar method of implanting or replacing TA pump 300a without the need for cardiopulmonary bypass is illustrated in FIGS. 18A through 18B. In a number of embodiments of a procedure for attachment of TA pump 300 hereof, thoracic aorta 20 is clamped in a manner to preserve a thoracic aortic lumen for continuing aortic blood flow during the implant operation. The continued thoracic aortic blood flow eliminates the need for placing the patient on cardiopulmonary bypass during pump implant. If a counter pulsation TA pump hereof could be implanted or replaced without the need for cardiopulmonary bypass, it would be much simpler and quicker than if bypass is required. Also, reducing surgical and anesthesia time would reduce postoperative complications.

As described further below, in a number of embodiments, TA pump 300, when unattached to thoracic aorta 20, includes open chamber section 320 with, for example, unattached or unzipped zipper halves or edges 140 located on the open edge of chamber section 320. Front moving plate 350 of the pump 400 and the back stationary plate 330 of the pump 400 cover much of the edges of open chamber 320 except at the very proximal and distal ends of the unzipped polyurethane zipper halves 140. Two front and back zippers halves 140 may, for example, be similar to ordinary clothes zippers in that they have a movable closing member, that when pulled or pushed, closes the mating halves of the zipper. Each of the two (front and back) zipper closing members may, for example, have an attached string for pulling the closing member to close and connect the two halves of the zippers. The zippers or other connection mechanism may, for example, be capable of sealing fluid up to a 5 PSI pressure level, well above that of the aortic blood pressure. Such zipper connections may facilitate pump replacement in the event of mechanical pump failure and eliminate the need for cardiopulmonary bypass during such replacement.

The recipient of TA pumps hereof will be given anesthesia and the thoracic aorta 20 exposed by, for example, a left lateral thoracotomy. A specially designed Satinsky clamp 900 may, for example, be used to clamp at least a 5 inch length of thoracic aorta 20. FIGS. 15A and 15B, for example, illustrate the placement of the Satinsky clamp 900 on the thoracic aorta 20. One can observe that the position of the Satinsky clamp 900 preserves a blood flow lumen 80 for continued blood flow to the body, thereby eliminating the need for bypass.

In a number of embodiments, on the thoracic aortic side of the intermediate connector section 150, a seating or mouth is created from two layers of biocompatible film. As described above, a removable connection may, for example, be formed between the intermediate connector section 150 and open chamber section 320. The thoracic aortic wall 20, two intermediate connector sections 150, and chamber section 320 combine to form the pumping chamber 380. The intermediate connector section(s) 150 are connected to the incised thoracic aorta lips 70 at a first end or edge thereof and include one or more releasable connectors or connector sections on a second end or edge thereof. Open chamber section 320 includes one or more releasable cooperating connectors or connector sections on or around the opening edge thereof to form a releasable connection with the cooperating connectors or connector sections of intermediate connector section(s) 150.

In a number of embodiments, intermediate connector section 150 is formed from biologically compatible or biologically inert vascular patch material such as ACUSEAL™ polymer available from Gore Medical of Newark, Del., which is an expanded polytetrafluoroethylene (ePTFE) with an equally biologically inert middle layer of elastomeric fluoropolymer. FIGS. 16A and 16B, for example, illustrates the sutured connection to the aortic lips 70 of the incised aorta 20 of one side of intermediate connector section straps 150 formed from such a polymer. Straps 150 include a cooperating connector or connector section in the form of a zipper half 130 on an opposite edge (the free edge). In that regard, straps 150 include one half, a zipper half 130, of an unzipped zipper 120 on their free side or edge. On the edge of straps 150 to be connected with the aortic lips 70, two layers of ACUSEAL form a mouth or seating as described above, which may be applied to the inside and outside surfaces of the incised aortic lip 70. The sutures 160 may be used to pull the aortic lip 70 into the mouth or the seating of the intermediate connector section straps 150 produced by the two layers of ACUSEAL. A surgical stapler may, for example, then apply a series of staples 170, see, for example, FIG. 16D, to connect the aortic lips 70 within seating 150 as shown in FIG. 16B. When the two front and back intermediate connector section straps 150 are securely stapled to the front and back lips 70 of the incised thoracic aorta 20, the opening of the thoracic aorta now has an unzipped zipper around the perimeter of the opened thoracic aorta (see, for example, action (c) of FIG. 16B).

The next stage or action is shown in (d) of FIG. 16B wherein the TA pump 300, only the open chamber section 320 of which is illustrated in action (d) of FIG. 136, is positioned for connection of the zipper half 140 of open chamber section 320 to zipper half 130 of intermediate connector section straps 150 at the proximal location adjacent the thoracic aorta 20. The zipper halves 130 and 140 closest to the chest wall are the first to be zipped together to form rear zipper connection 120. On the blood side of the zipper, there may, for example, be positioned two elastomeric beads that mate and seal to hold at least 5 PSI fluid pressure. Blood pressure is typically 0.5 to 1.5 PSI. Subsequently, the front zipper halves 130 and 140 are zipped together to form front zipper connection 120. Because the top plate 350 and the bottom plate 330 of the TA pump 300 will be in the way of a typical zipper closing action, the zipper closure mechanism may, for example, be connected to a pulling rod or string (as described above) to close the zipper connections 120 as illustrated in FIG. 16C. Access to the beginning and ending locations of the zipper connections 120 is available because the beginning and ending of the zipper connections 120 are above and below the location of the top plate 350 and bottom plate 330.

FIG. 16D illustrates a cutaway view of chamber section 320 connected to intermediate section 150 to form pumping chamber 380. As described above, pumping chamber 380 is formed by the thoracic aorta 20 connected to the chamber section 320 using the intermediate connector sections or straps 320. The two layers of, for example, ACUSEAL extending from the side of the strap cover both sides of the incised thoracic aortic lip. Staples 170 secure the ACUSEAL layers to the thoracic aortic lip. The blood pumping chamber 380 is thus formed by the perimeter of the aortic incision being secured to the two intermediate connector section straps 150 (only one intermediate connector section strap 150 is shown in FIG. 16D) on one side of the strap and by zipping the zipper 120 on the opposite side of the strap to the perimeter of chamber section 320.

As described above, pumping chamber 380 is finally assembled and constructed by inserting the back zipper top end into the closing member of the back zipper at its most proximal location. The string is then pulled downward until the back zipper is completely connected. The same procedure is then used to connect the front zipper. Any leakage paths located at the zipper ends may, for example, be closed by the surgeon with suturing. Once the pumping chamber has been constructed, any remaining trapped air in the chamber may, for example, be replaced with heparinized saline through a port attached to the chamber. FIG. 13E illustrates the use of a sealable port 210 connected to the empty bag 200 for alternatively removing air and inserting heparinized saline until no air remains. At this point, the Satinsky clamp 900 may be removed and the TA pump 300 will take it's natural location in the chest. FIG. 13F illustrates how TA pump 300 is connected to a rib 40 above and a rib 40 below the TA pump 300 by, for example, two bone screws 332 passing through extending connective members 331.

In a number of embodiments, the rigid members or plates 330 and 350 hereof (and other rigid member hereof) used in connection with pumping chamber 380 hereof (and other pumping chambers hereof) move together and apart in a direction that is generally perpendicular to a radial line R (see FIG. 17) extending from the longitudinal axis of the native aorta 20 (for example, at the midpoint of the length of the incised aorta 20 to which the chamber section 320 is connected to the aorta 20). In other words, there need not be any significant radial component to the direction of motion. Such a pumping motion may, for example, provide for an increased volume of the pumping chamber as compared to pumps that radially compress the aorta or a volume in fluid connection with the aorta. In a number of embodiments as described herein, the constructed pumping chamber extends, for example, laterally and backwardly from the aorta with a stationary rigid member of the pump system being next to the chest wall, and a movable rigid member of the pump system being next to the lung surface. This positioning/conformation creates a substantially larger pumping surface than would exist if the aorta alone were used. The human anatomy provides the space for this pumping chamber against the chest wall by displacing a small volume of lung, which will have little effect on lung function. In attachment of the pump system to the descending thoracic aorta, it is very desirable to leave any portion of the aortic wall undisturbed that is the origin of inter-costal arteries leaving the thoracic aorta, because these arteries provide the blood supply for the spinal cord. In other positions of the aorta wherein arteries leaving the aorta are not present, a pumping chamber that completely replaces a length or section of the aorta may, for example, be used.

With reference to FIGS. 18A through 18G, connecting an in-parallel form of the thoracic aorta heart assist device or TA pump such as TA pump 300a may, for example, include use of a template 1100 to mark, using a marker 1200, the positions and lengths of incisions to be made in thoracic aorta 20 for attachment of connecting conduits 150a, see FIG. 18A. A similar template may be used to mark the position and length of the incision for TA pump 300 as described above. After marking, the surgeon clamps the aorta in two locations with two Satinsky clamps 900a where marked using template 1100 as illustrated in FIG. 18B. The Satinsky clamps are used to clamp at least a length of thoracic aorta 20 sufficient to attached connective conduits 150a. The positioning of Satinsky clamps 900a preserves a blood flow lumen in thoracic aorta 20 for continued blood flow to the body, thereby eliminating the need for bypass. The clamped aortic wall sections are then incised as illustrates in FIG. 18C and connective conduits 150a are sutured to the incised lips of the aorta as illustrated in FIG. 18D. A quick connect or coupling method may, for example, be used for connecting the free ends of grafted connective conduits 150a to the open ends of inlet conduit 384a and outlet conduit 386a via quick couplings or connectors 140a as illustrated in FIG. 18E.

In general, implantation of an in-parallel TA pump such as TA pump 300a is simpler than implantation of an integral TA pump such as TA pump 300. In a number of embodiments, standard Satinsky clamps may be used to seal thoracic aorta 20. Quick connectors 140a may be used to reduce implant time. A representative embodiment of connector 140a is shown, for example, in FIGS. 19A through 19D. In the illustrated embodiment, connective conduit 150a includes a radially outward extending flanged end 152a that seats within a resilient ring 142a of connector 140a in cooperation with a radially inward extending flange or seating 144a (see, for example, FIG. 19D).

Resilient ring 142a is made from a biocompatible, resilient material such a MP35N cobalt steel, and includes an opening 146a. A ring spreading device (not shown), which may be readily customized for use herein, may be used to open the ring 142a. In a number of embodiments, flange 152a and/or cooperating flange 144a may be dimensioned so that it is difficult or not possible to spread ring 142a sufficiently to remove ring 142a from connection with flange 152a of connective conduit 150a. In FIG. 19A ring 142a, with flange 152a of connective conduit 150a seated therein, has been spread to an extended or opened state to allow seating of, for example, a radially outward extending flange 384aa formed on the end of inlet conduit 384a of pumping chamber 380a (or on an conduit section attached to an end of inlet conduit 384a). Upon seating of flange 384aa to abut flange 152a as illustrated in FIG. 19B, ring 142a is returned to its relaxed or closed state as illustrated in FIG. 19C. Flanges 144a and 148a of ring 142a cooperate with flanges 152a and 384aa to compress flanges 152a and 384aa, respectively, together to form a sealed engagement. Flanges 144a and 148a may, for example, form a generally U-shaped or V-shaped seating to cooperate with flanges 152a and 384aa, which may be beveled. As illustrated in FIG. 19D flanges 144a and 148a may be angled to provide compressive force. The distal end of flanges 152a and 384aa may, for example, be coated with a biocompatible elastomeric material, represented as layers 152a' and 384aa' respectively in FIG. 19D, such as a polyurethane to assist in maintaining a sealed connection. Unlike integral TA pump 300, in-parallel TA pump 300a does not require reconstruction of thoracic aorta 20. In-parallel TA pumps such as TA pump 300a thus may reduce, minimize or eliminate the risk of damaging inter-costal arteries that emanate from thoracic aorta 20 and provide the blood supply to the spinal cord. Interruption of this blood supply can damage the spinal cord, leading to paralysis.

Figure 21:
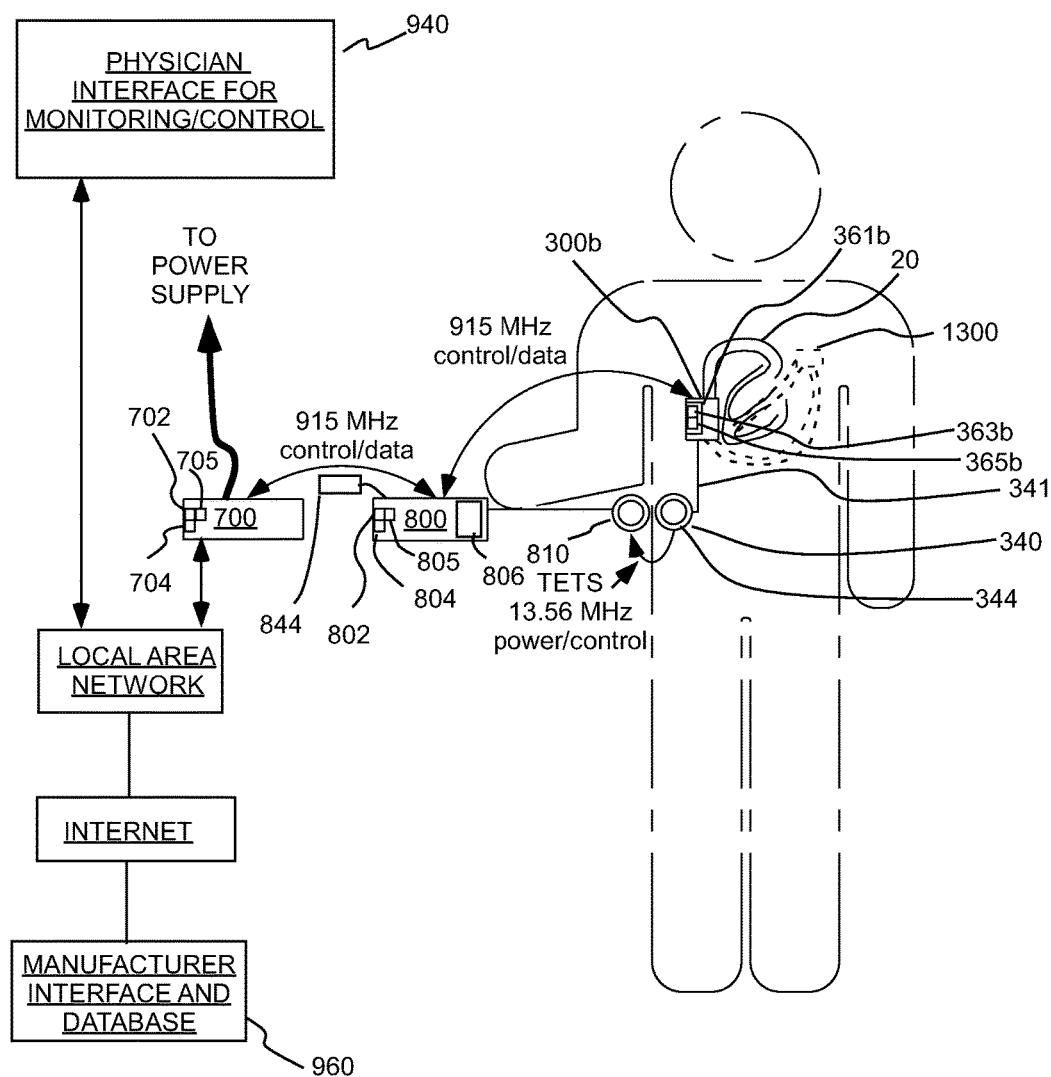
FIG. 21 illustrates schematically an embodiment of a VAD system including a TA pump hereof.

Similar to TA pump 300, rearward, stationary rigid plate 330a and forward rigid plate 350a of TA pump 300a, including connected hermetically sealed compartment 360a, are attached to pumping chamber 380a, via a passage or open section 312a' (FIG. 18E) formed by bellows 312a to complete construction of TA pump 300a as illustrated in FIG. 18F. Each of rearward rigid plate 350a and the assembly of forward, moveable plate 330a and hermetically sealed compartment 360a are, for example, illustrated in FIG. 12A. Lead 341 is connected between TA pump 300a and internal TETS coil 340. A standard bipolar epicardial pacemaker lead 1301 may, for example, be connected between TA pump 300a and, and the surface of the left ventricle, as illustrated in FIG. 18G. In other embodiment, a pacemaker 1300, as illustrated in FIG. 21, may send signals of heart function to a TA pump hereof as well as control hear function in connection with the TA pump as, for example, described in US Patent Application Publication No. 2013/0041204. FIG. 3A illustrates how TA pump 300a may be connected to the patient's ribs by two bone screws 332a passing through extending connective members 331a.

Figure 20A:
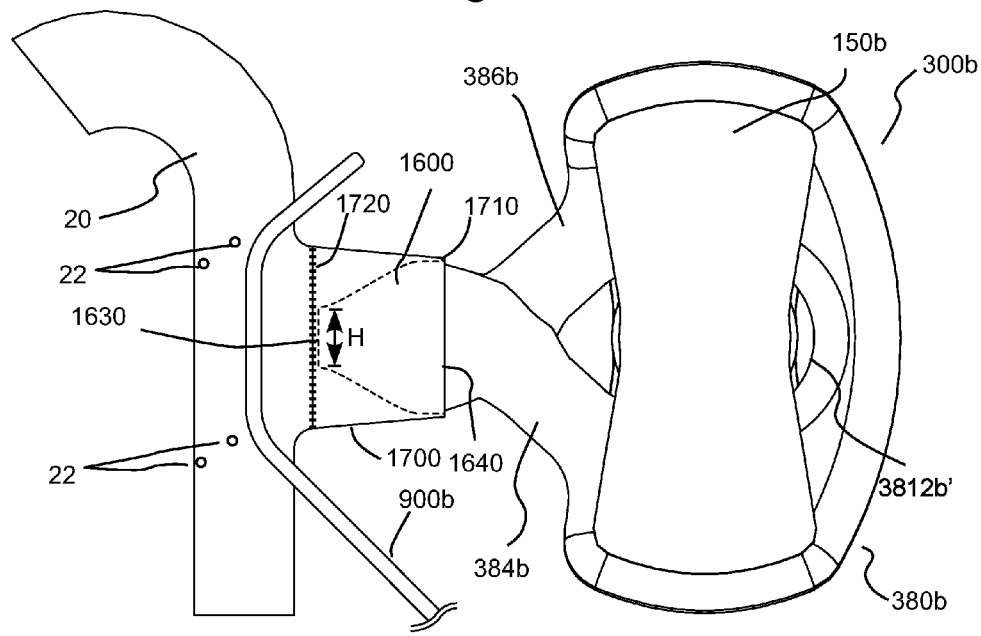
FIG. 20A illustrates a method of implanting the TA pump of FIG. 2I.

In attaching connector 1600 for use in connection with, for example, TA pump 300b, an enclosure of skirt 1700 of flexible but fluid-impervious material may, for example, surround the connector 1600 as illustrated in FIG. 20A. In that regard, a first peripheral end 1710 of skirt 1700 may be attached to the periphery of a joint area between front face 1640 of connector 1700, in which ports 1612 and 1622 are formed, and TA pump 300b. In a number of embodiments, a DACRON graft may be used in forming a sealed connection. During implantation, the other, open end of skirt 1700 would face thoracic aorta 20. Thoracic aorta 20 may be carefully clamped via a Satinsky clamp 900b to avoid any inter-costal arteries and to preserve a blood flow path in thoracic aorta 20. The surgeon would then incise a portion of the clamped aorta to produce a purse lipped aortic incision. The perimeter of the pursed lip aortic incision would allow connector 1600 to enter the lumen of thoracic aorta 20. With the clamp still in place, the surgeon would carefully suture second end 1720 of skirt 1700 to the free edge of the incised aorta, creating a fluid tight chamber containing the space within the skirt as well as the connector 1600 and TA pump 300b itself.

Figure 20B:
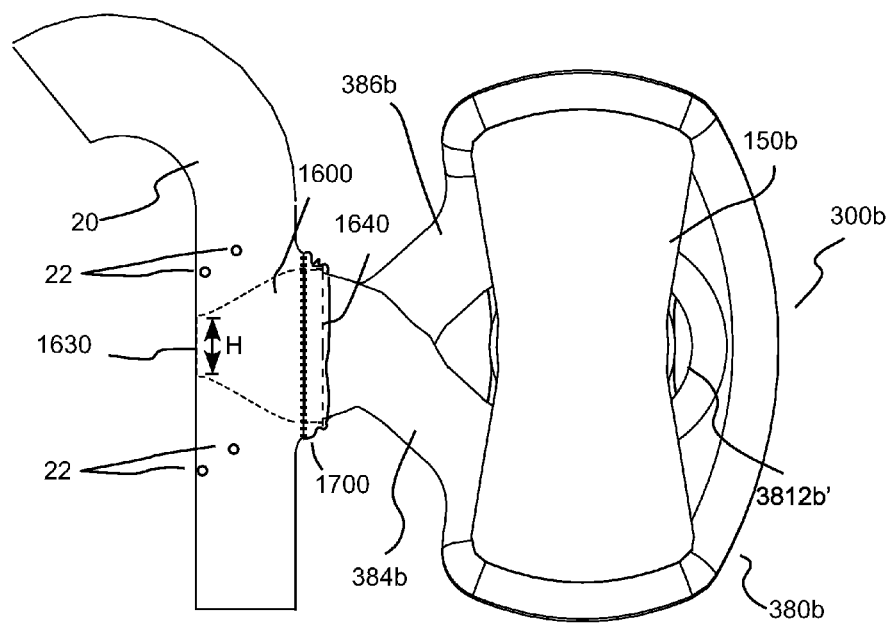
FIG. 20B further illustrates the method of FIG. 20A wherein a connector for the TA pump of FIG. 2I is inserted into fluid connection with a lumen of the thoracic aorta.

Using, for example, a hypodermic syringe and needle, the surgeon may then replace any air within skirt 1700 and in any blood flow channels of pump 300b and connector 1600 with, for example, a clot-resisting heparinized saline solution. The clamp would then be released and rearward end of side 1640 of connector 1600 would be inserted into thoracic aorta 20 and, for example, nested against the back inside wall of thoracic aorta 20 as illustrated in FIG. 20B. The excess material of skirt 1700 folds onto itself as illustrated in FIG. 20B. A soft DACRON strap (not shown) may, for example, then be slid behind thoracic aorta 20. The free ends of the strap would be then connected to pump 300b on opposite sides of pump 300b to hold pump 300b firmly into thoracic aorta 20. A tie strap with, for example, soft DACRON would be placed around the waist or first end 1710 of skirt 1700 and connector 1600. Connector 1600 may be securely in place in the aorta and the blood flow channels between the aorta and pump 300b will be open and operative. If pump 300b needed to be replaced, skirt 1700 could be used again during such replacement.

Connector 1600 may, for example, be formed to have generally the shape of thoracic aorta over the portion thereof that is inserted into thoracic aorta 20. In a number of embodiments, inlet 1610 of connector 1600 and outlet 1620 of connector 1600 (see FIGS. 3A-3C) are formed in connector 1600 to be positioned such that connector 1600 is adapted to be slid into a lumen of the thoracic between two adjacent sets of inter-costal arteries so that the inlet of the connector and the outlet of the connector occupy a volume occupied by the thoracic aorta before placing the connector in fluid connection with the thoracic aorta. In a number of embodiments, rearward side 1640 of connector 1600 which is adapted to face a rearward side of the thoracic aorta upon placing the connector in fluid connection with the thoracic aorta is no greater than approximately 0.0191 meters, or not greater than approximately 0.0127 meters in height to enable placement between adjacent sets of inter-costal arteries 22 without blockage thereof. As illustrated, for example, in FIGS. 20A and 20B, connector 1600 may gradually increase in profile or height across the depth thereof, between rearward side 1640 and forward side 1630.

Control

FIG. 21 illustrates a representative embodiment of a VAD system hereof including TA pump 300b as a representative example of a TA pump hereof, which shows the TA pump 300b attached to the thoracic aorta 20. Any TA pump hereof can be used in connection with the VAD system illustrated in FIG. 21. As described above, internal TETS coil 340 may have a direct wired connection to TA pump 300b via lead 341, see FIG. 18G. External TETS coil 810 is placed over and aligned with the internal TETS coil 340 by the elastic vest 600 as described above.

External controller 800 includes battery system or pack 806 and electronics to provide power, communications and control for any implanted pump. In that regard, external controller includes control system 802 which may, for example, include one or more processors/microprocessors. External controller also includes communication system 804 which may provide for wired and/or wireless communication. As described above, external controller 800 may be supported upon the patient, for example, on the patient's back by elastic vest 600 as illustrated FIG. 5A. A cell phone 840 may, for example, optionally be used to provide two way control and data communication via, for example, Bluetooth wireless protocol with the external controller 800. In a number of embodiments, patient interface 844, which may be operatively connected to external controller 800 via a tethered connection, may, for example, provide information for the patient to properly manage the implanted TA pump 300b, for example, to effect actions such as changing out external controller/battery packs on a timely basis. Electronic 361b of TA pump 300b and other pumps hereof include a control system 363b, including, for example, one or more processors/microprocessors, and a communications system 365b for wireless communication with, for example, external controller 800. Wireless communication between external controller 800 and implanted pump 300b may, for example, be effected via a two-way 915 megahertz (MHz), communication protocol as known in the wireless communications arts. Control of pumps and communication between implanted pumps and external controllers is, for example, discussed in U.S. Patent Application Publication Nos. 2013/0041204 and 2013/0289334, the disclosures of which are incorporated herein by reference. As described above, operational and control methodologies for TETS suitable for use herein are described in U.S. Patent Application Publication No. 2013/0289334.

Patient base station 700 includes a control system 702 including one or more processors/microprocessors, a memory system 705 in operative connection with control system 702, and a communication system 704 in operative connection with control systems 702 and adapted for wireless and/or wired communication. Patient base station 700 may, for example, have the function of communication with external controller 800, with a manufacturer database/interface 960 and/or with a physician interface 940 via wired or wireless communication either directly or via a network such as the internet or a local area network or LAN. This communication may, for example, be accomplished through a two-way ethernet communication connection to send and receive control signals and data. In a number of embodiments, patient base station 700 is capable of two-way 915 megahertz communication with both external controller 800 and implanted electronics such as electronics 361. Patient base station 700 may, for example, be operable for internet communication with manufacturer database and/or interface 960. Patient base station 700 may also communicate with a physician interface, for example, a browser-based interface, through which the physician may, for example, monitor and set control parameters for the implanted TA pump. Patient base station 700 may also store data such as historical data of the operation of the implanted TA pump and/or the external systems in a memory system operatively connected to control system 702 which can be accessed by a physician or the manufacturer. Communication may, for example, occur through a LAN in the physician's office. The LAN, in turn, may send one-way or two-way data through the internet to the manufacturers interface and/or database 960.

Figure 22:
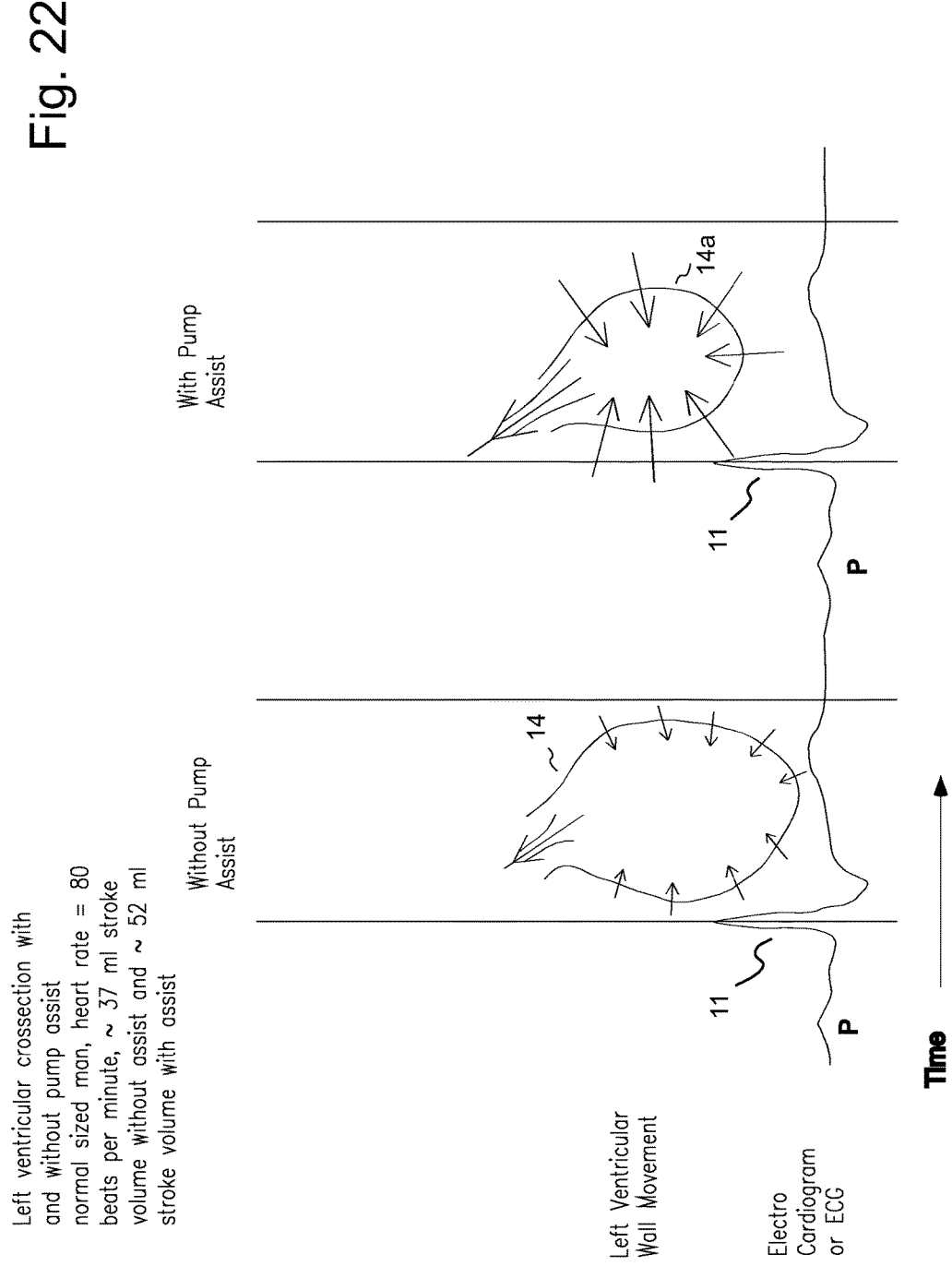
FIG. 22 illustrates the contraction of a failing left ventricle and the contraction of an assisted left ventricle.
Figure 23:
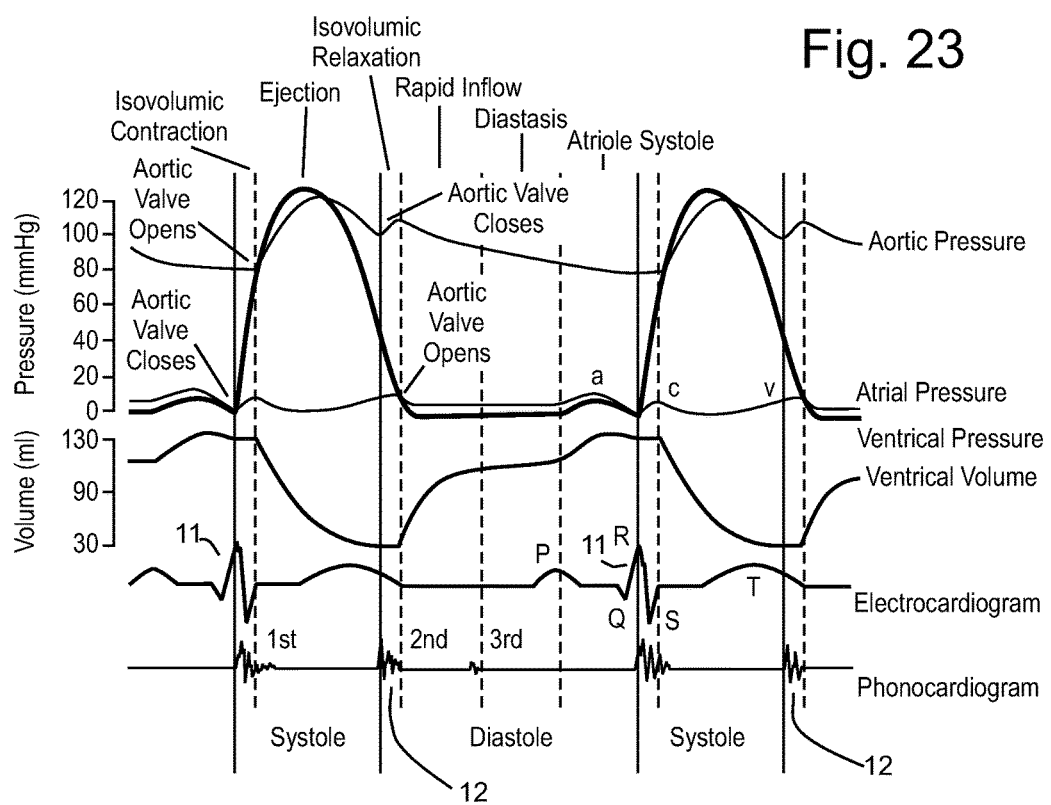
FIG. 23 illustrates the relationship between mechanical activity and electrical activity in the heart, including the R wave.
Figure 24:
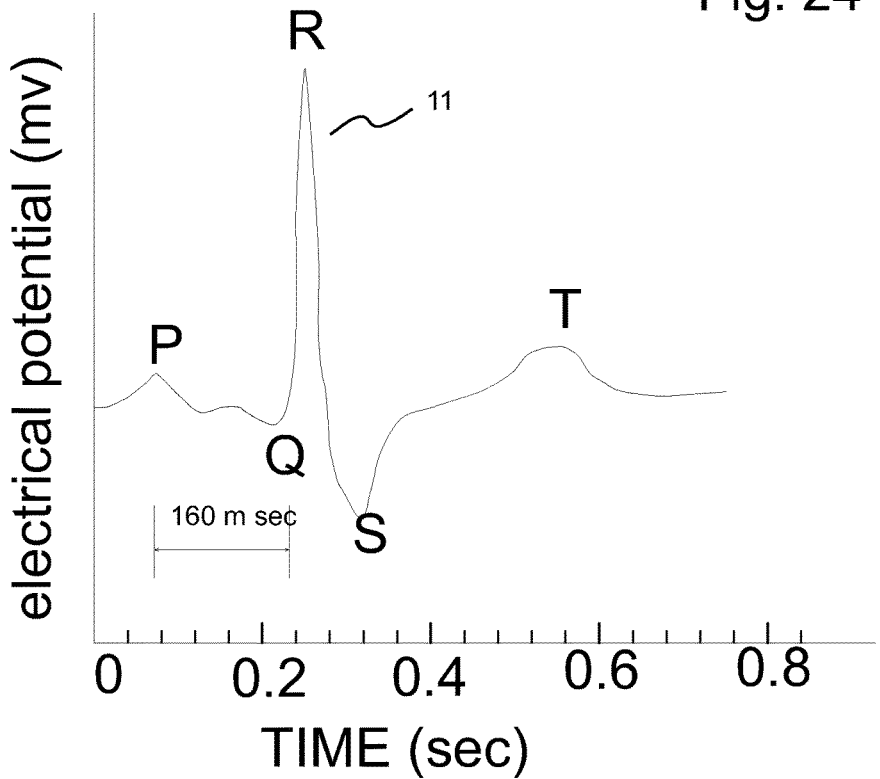
FIG. 24 illustrates an expanded view of a normal ECG, with the P wave preceding the start of the QRS complex by approximately 160 milliseconds (ms).

FIG. 22 illustrates a contracting failing left ventricle and a contracting assisted left ventricle. In each illustrated case, the ventricular contraction is immediately preceded by the R wave 11 of the electrocardiogram or ECG signal (see FIGS. 22 and 23). Detection of the R wave using sensing pacing lead 1301, directly connected to the left ventricle may, for example, be used with proper amplification and amplitude threshold detection to time the beginning of the expansion of the blood pumping chamber. The internal controller, 363b may, for example, be used in sensing heart function via a lead 1301. FIG. 23 illustrates the relationship between mechanical activity and electrical activity in the heart including the R wave 11 of the ECG as well as the second heart sound 12 of the phonocardiogram. The heart sounds may be sensed by a piezoelectric sensor/microphone attached to, for example, the surface a rigid or member plate of the TA pumps hereof as described in connection with sensor 364a illustrated, for example, in FIG. 8 and using proper amplification and logical sequencing compared with the timing of the R wave of the ECG. Detection of the second heart sound may, for example, be used to time the beginning of compression of the blood pumping chamber. FIG. 23 illustrates an expanded view of a normal ECG with the P wave preceding the start of the QRS complex by approximately 160 milliseconds (ms). The P wave represents the electrical activity of the heart's atria or entrance chambers.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:
1. An implantable heart assist system, comprising:
    a compressible pumping chamber comprising an inlet conduit configured to be placed in fluid connection with the descending thoracic aorta and an outlet conduit configured to be placed in fluid connection with the thoracic aorta; and
    a pump system comprising a first rigid member, a second rigid member spaced from the first rigid member so that at least a portion of the pumping chamber may be positioned between the first rigid member and the second rigid member, a drive system comprising a motor and an actuator mechanism to convert rotary motion of the motor to linear motion to cause the second rigid member to move toward the first rigid member or away from the first rigid member, and a controller in operative connection with the drive system and controlling the motor, movement of the second rigid member toward the first rigid member causing compression of the pumping chamber and movement of the second rigid member away from the first rigid member causing expansion of the pumping chamber, the first rigid member being configured to be positioned adjacent the chest wall posterior to the thoracic aorta and the second rigid member being configured to be positioned adjacent the surface of the left lung.

2. The heart assist system of claim 1 further comprising at least one heart function sensor in operative connection with the controller.

3. The heart assist system of claim 1 wherein the second rigid member configured to displace a portion of a volume normally occupied by the left lung.

4. The heart assist system of claim 1 wherein the heart assist system further comprises a fluid connector configured to be placed in fluid connection with the descending thoracic aorta to divert all blood flow from the descending thoracic aorta to the pumping chamber via the inlet conduit and to return the blood flow to the thoracic aorta via the outlet conduit.

5. The heart assist system of claim 1 wherein the drive system is positioned between the first rigid member and the second rigid member within an open area formed in the compressible pumping chamber.

6. The heart assist system of claim 5 wherein the heart assist system further comprises a connector configured to be placed in fluid connection with the thoracic aorta, the connector comprising an inlet configured to be placed in fluid connection with the descending thoracic aorta, a first port in fluid connection with the inlet of the connector via a first curved conduit, an outlet configured to be placed in fluid connection with the descending thoracic aorta, and a second port in fluid connection with the outlet of the connector via a second curved conduit, the first port being configured to be placed in fluid connection with the inlet conduit of the compressible pumping chamber and the second port being configured to be placed in fluid connection with the outlet conduit of the compressible pumping chamber.

7. The heart assist system of claim 6 wherein the inlet of the connector and the outlet of the connector are positioned such that the connector is configured to be slid into a lumen of the thoracic aorta between two adjacent sets of intercostal arteries so that the inlet of the connector and the outlet of the connector occupy a volume occupied by the thoracic aorta before placing the connector in fluid connection with the thoracic aorta.

8. The heart assist system of claim 6 wherein a rearward side of the connector, which is configured to face a rearward side of the thoracic aorta upon placing the connector in fluid connection with the thoracic aorta, is no greater than 0.0191 meters in height.

9. The heart assist system of claim 8 wherein the inlet of the connector and the outlet of the connector are placed in fluid connection only via the compressible pumping chamber upon fluid connection of the first port and the inlet conduit and fluid connection of the second port and the outlet conduit.

10. The heart assist system of claim 1 further comprising a biocompatible gel material to be interposed between the first rigid member and the chest wall such that deformation of the biocompatible gel material accommodates surface form differences between the pump system and the chest wall.

11. The heart assist system of claim 1 wherein an outer surface of the second rigid member comprises a lubricious coating disposed thereon.

12. The heart assist system of claim 11 wherein the lubricious coating comprises a fluoropolymer.

13. The heart assist system of claim 1 wherein a stroke volume of the pump system can be varied by the controller by controlling the number of rotations of a rotor of the motor.

14. The heart assist system of claim 13 wherein a full range of motion of the second rigid member toward the first rigid member and a full range of motion of the second rigid member away from the first rigid member are each effected by 2 to 6 rotations of a rotor of the motor.

15. The heart assist system of claim 1 further comprising a first mechanical stop mechanism to limit the motion of the second rigid member toward the first rigid member and a second mechanical stop mechanism to limit motion of the second rigid member away from the first rigid member, the first mechanical stop mechanism and the second mechanical stop mechanism comprising an elastomeric material to absorb energy.

16. The heart assist system of claim 1 wherein the compressible pumping chamber is adapted to be attached to the thoracic aorta.

17. The heart assist system of claim 16 wherein the compressible pumping chamber comprises a chamber section adapted to be attached to the thoracic aorta which extends radially outward beyond a radial position of a native thoracic aorta wall to which it is attached.

18. The heart assist system of claim 1 wherein the inlet conduit is configured to be placed in fluid connection with the descending thoracic aorta at a first position and the outlet conduit is configured to be placed in fluid connection with the descending thoracic aorta at a second position which is below the first position.

19. The heart assist system of claim 1 wherein movement of the second rigid member relative to the first rigid member is controlled such that the volume within the compressible pumping chamber is decreased early in diastole and the volume within the compressible pumping chamber is increased in at least one of late in diastole or early in systole.

20. The heart assist system of claim 1 wherein the compressible pumping chamber is attached to the first rigid member on a first side of the compressible pumping chamber and the compressible pumping chamber is attached to the second rigid member on a second side of the compressible pumping chamber.

21. The heart assist system of claim 1 wherein the compressible pumping chamber comprises a biocompatible, flexible polymer.

22. A method of assisting a patient's heart, comprising:
implanting a heart assist system by placing a compressible pumping chamber in fluid connection with the descending thoracic aorta via an inlet conduit of the compressible pumping chamber and an outlet conduit of the compressible pumping chamber; the heart assist system further comprising a pump system comprising a first rigid member, a second rigid member spaced from the first rigid member so that at least a portion of the compressible pumping chamber may be positioned between the first rigid member and the second rigid member, the first rigid member being positioned adjacent the chest wall posterior to the descending thoracic aorta and the second rigid member being positioned adjacent the surface of the left lung, a drive system comprising a motor and an actuator mechanism to convert rotary motion of the motor to linear motion to cause the second rigid member to move toward the first rigid member or away from the first rigid member, and a controller in operative connection of the drive system and controlling the motor, wherein movement of the second rigid member toward the first rigid member results in compression of the compressible pumping chamber and movement of the second rigid member away from the first rigid member causes expansion of the compressible pumping chamber; and controlling the motor via the controller to move the second rigid member toward and away from the first rigid member.

* * * * *

UNITED STATES PATENT AND TRADEMARK OFFICE
CERTIFICATE OF CORRECTION

PATENT NO. : 9,707,327 B2  
APPLICATION NO. : 14/776927  
DATED : July 18, 2017  
INVENTOR(S) : Marlin S. Heilman et al.

Page 1 of 1

It is certified that error appears in the above-identified patent and that said Letters Patent is hereby corrected as shown below:

Column 25, Line 18, delete "FIGS. 3I through 3L" and insert --FIGS. 2I through 2L--  
Column 39, Line 24, delete "FIG. 13E" and insert --FIG. 14E--  
Column 39, Line 29, delete "FIG. 13F" and insert --FIG. 14F--

Signed and Sealed this  
Tenth Day of July, 2018

Andrei Iancu  
*Director of the United States Patent and Trademark Office*